(12) United States Patent
Rajwa et al.

(10) Patent No.: US 11,867,690 B2
(45) Date of Patent: *Jan. 9, 2024

(54) IDENTIFICATION OF FUNCTIONAL CELL STATES

(71) Applicant: ASEDASCIENCES AG, Schindellegi Switzer (CH)

(72) Inventors: Bartlomiej Rajwa, West Lafayette, IN (US); Vincent T Shankey, Miami, FL (US)

(73) Assignee: ASEDASCIENCES AG, Schindellegi Switzer (CH)

( * ) Notice: Subject to any disclaimer, the term of this patent is extended or adjusted under 35 U.S.C. 154(b) by 73 days.

This patent is subject to a terminal disclaimer.

(21) Appl. No.: 17/394,521

(22) Filed: Aug. 5, 2021

(65) Prior Publication Data

US 2021/0364499 A1 Nov. 25, 2021

Related U.S. Application Data

(63) Continuation of application No. 15/111,339, filed as application No. PCT/US2015/011441 on Jan. 14, 2015, now Pat. No. 11,137,388.

(60) Provisional application No. 61/927,247, filed on Jan. 14, 2014.

(51) Int. Cl.
| | | |
|---|---|---|
| G01N 33/48 | (2006.01) | |
| G01N 33/50 | (2006.01) | |
| G16C 20/30 | (2019.01) | |
| G16C 20/40 | (2019.01) | |
| G16C 99/00 | (2019.01) | |

(52) U.S. Cl.
CPC ....... *G01N 33/5041* (2013.01); *G01N 33/502* (2013.01); *G01N 33/5008* (2013.01); *G01N 33/5026* (2013.01); *G16C 20/30* (2019.02); *G16C 20/40* (2019.02); *G16C 99/00* (2019.02)

(58) Field of Classification Search
CPC ............. G01N 33/5041; G01N 33/502; G01N 33/5026
See application file for complete search history.

(56) References Cited

U.S. PATENT DOCUMENTS

| | | |
|---|---|---|
| 5,544,650 A | 8/1996 | Boon et al. |
| 6,656,695 B2 | 12/2003 | Berg et al. |
| 6,801,859 B1 | 10/2004 | Friend et al. |
| 6,834,237 B2 | 12/2004 | Noergaard et al. |
| 6,998,249 B1 | 2/2006 | McKim et al. |
| 7,146,349 B2 | 12/2006 | Benitez-Jimenez et al. |
| 7,912,651 B2 | 3/2011 | Berg et al. |
| 7,989,218 B2 | 8/2011 | Michnick et al. |
| 8,101,364 B2 | 1/2012 | Michnick et al. |
| 8,467,970 B2 | 6/2013 | Berg et al. |
| 8,831,889 B2 | 9/2014 | Rajwa et al. |
| 11,137,388 B2 * | 10/2021 | Rajwa ............... G01N 33/502 |
| 2002/0107827 A1 | 8/2002 | Benitez-Jimenez et al. |
| 2003/0113807 A1 | 6/2003 | Berg et al. |
| 2003/0162301 A1 | 8/2003 | Noergaard et al. |
| 2004/0063088 A1 | 4/2004 | Berg et al. |
| 2004/0157269 A1 | 8/2004 | Berg et al. |
| 2007/0087344 A1 | 4/2007 | Plavec et al. |
| 2007/0135997 A1 | 6/2007 | Hytopoulos |
| 2008/0064056 A1 | 3/2008 | Berg et al. |
| 2008/0070271 A1 | 3/2008 | Berg et al. |
| 2010/0197006 A1 | 8/2010 | Benenson et al. |
| 2013/0226469 A1 | 8/2013 | Robinson et al. |
| 2013/0266967 A1 | 10/2013 | Berg et al. |

FOREIGN PATENT DOCUMENTS

| | | |
|---|---|---|
| JP | 08-510051 A | 10/1996 |
| JP | 2003510093 A | 3/2003 |
| JP | 2003520567 A | 7/2003 |
| JP | 2003527110 A | 9/2003 |
| JP | 2003535330 A | 11/2003 |
| JP | 2007532132 A | 11/2007 |
| WO | 9416314 A1 | 7/1994 |
| WO | 09146036 A2 | 12/2009 |

OTHER PUBLICATIONS

International Search Report dated Apr. 22, 2015, issued in the International Application PCT/US2015/011441 of which this application is the US National Phase application, 6 pages.

Hammer, M. et al., "WebFlow: A Software Package for High-Throughput Analysis of Flow Cytometry Data", Assay and Drug Development Technologies, vol. 7, No. 1, XP055182109, Feb. 1, 2009, pp. 44-55.

Feng, Y. et al, "Multi-parameter phenotypic profiling: using cellular effects to characterize small-molecule compounds", Nature Reviews Drug Discovery, vol. 8, No. 7, XP055182112, Jul. 1, 2009, pp. 567-578.

(Continued)

*Primary Examiner* — Russell S Negin
(74) *Attorney, Agent, or Firm* — MILLEN WHITE ZELANO AND BRANIGAN, PC; Larry S. Millstein

(57) ABSTRACT

Embodiments herein described provide methods for determining phenotypic parameters of cell populations and expressing them in terms of tensors that can be compared with one another. Embodiments provide methods for determining phenotypic parameters of cell populations in response to an agent. Embodiments provide methods for comparing effects of an agent on phenotypic parameters to effects of reference standards whose in vivo effects are known. Embodiments provide methods for predicting the effect of an agent by the comparison with the known effects of reference standards. Embodiments provide methods for classifying agents by their effects on phenotypic parameters. Embodiments provide software and computer systems for calculating multiparametric tensors, compressing their complexity and comparing them after compression.

19 Claims, 30 Drawing Sheets

(56) References Cited

OTHER PUBLICATIONS

Kolecki, J., "An Introduction to Tensors for Students of Physics and Engineering", URL: http://ntrs.nasa.gov/search.jsp?R=20020083040, XP055182113, Sep. 1, 2002, 29 pages.

International Preliminary Report on Patentability dated Apr. 28, 2016, issue in the International Application PCT/US2015/011441, of which this application is the US National Phase application, 14 pages.

Written Opinion dated Apr. 22, 2015, issued in the International Application PCT/US2015/011441 of which this application is the US National Phase application, 9 pages.

Written Opinion dated Jan. 28, 2016 issued in the International Application PCT/US2015/011441, of which this application is the US National Phase application, 6 pages.

Article 34 filed Nov. 13, 2015 in the International Application PCT/US2015/011441, of which this application is the US National Phase application, 10 pages.

Article 34 filed Mar. 25, 2016 in the International Application PCT/US2015/011441, of which this application is the US National Phase application, 4 pages.

M. H. Woehrmann et al., "Large-scale cytological profiling for functional analysis of bioactive compounds", Mol. BioSyst., 9:2604-2617 (2013).

Sklar et al., "Flow Cytometry for Drug Discovery, Receptor Pharmacology and High Throughput Screening", Curr. Opin. Pharmacol., 7(5):527-534 (Oct. 2007).

Office Acton corresponding KR Patent Application No. 10-2016-7022058 dated Jun. 25, 2021 (pp. 1-10).

Song:"A Case Report . . . "; Cytometry Part B {Clinical Cytometry} (2011) vol. 8OB, pp. 126-129,[A].

Davies et al. Nuclear topoisomerase II levels correlate with the sensitivity of mammalian cells to intercalating agents and epipodophyllotoxins. The Journal of Biological Chemistry, vol. 263, pp. 17724-17729. (Year: 1988).

Laerum et al. Clinical applications of flow cytometry: a review. vol. 1, pp. 1-13. (Year: 1981).

English translation of Office Action in corresponding Japan Patent Application No. 2016-263912 dated Nov. 30, 2018 {pp. 1-2).

Bernas et al: Cytometry Part A (73A: 715-7) (2008).

Jacob et al: Cytometry 12:550-568 (1991).

\* cited by examiner

Axis 1: Cell morphology
Axis 2: Functional fluorescence label
Axis 3: Perturbant concentration

IDENTIFICATION OF FUNCTIONAL CELL STATES

RELATED APPLICATIONS

This application is a continuation of U.S. Ser. No. 15/111,339 filed 13 Jul. 2016, which claims priority of and incorporates herein in its entirety Provisional Application number 61/927,247 filed 14 Jan. 2014 (now expired), and which is the US National Phase of International Application Number PCT/2015/011441 filed 14 Jan. 2014 (now expired) the entirety of which is herein incorporated by reference in its entirety including the claims and the abstract.

FIELD OF THE INVENTION

Embodiments relate to fields of cell assays, physiology, and drug development. Embodiments additionally relate to cytometry and to semi-automated and automated analysis of multi-parametric data, such as cytometry data.

GOVERNMENT FUNDING

No government funds were used in making the invention herein disclosed and claimed.

I

Phenotypic compound screening is an emerging technology for rapid assessment of pharmaceutical compounds. In recent years, a number of techniques have been developed to characterize phenotypic responses of cells to perturbants such as small molecules or biologics. The vast majority of reported work has used traditional bulk biochemical assays or single-cell techniques based on high-content screening (automated microscopy). For instance, see Abraham et al. ("High content screening applied to large-scale cell biology." Trends Biotechnol. 22, 15-22, 2004) and Giuliano et al. ("Advances in High Content Screening for Drug Discovery." ASSAY Drug Dev. Technol. 1, 565-577, 2003), which are incorporated by reference herein in parts pertinent thereto.

More recently, novel statistical methods have been implemented in the analysis of complex screening datasets. These methods can provide a means to determine correlations between datasets. Simple pathway-driven models for screening are described in Cong et al. ("Method for using division arrested cells in screening assays," EP 1581645), which is incorporated by reference herein in parts pertinent thereto. Cong proposes studying signal transduction in growth-arrested cells and using such systems to screen for agents that modulate the activity of cell surface receptors such as the β2 adrenergic receptors (β2AR), a type of G-protein coupled receptor. Cong demonstrates that even in such growth-arrested cells, treatment with isoproterenol (100 μM) increases secreted alkaline phosphatase (SEAP) activity, which in turn establishes that growth arrested cells still have intact signal transduction pathways down to the transcriptional response, and enzyme reporter assays can be carried out using such systems.

A similar technique is provided by Hytopoulos et al. ("Methods for analysis of biological dataset profiles." US patent app. pub. No. 2007-0135997), which is incorporated by reference herein in parts pertinent thereto. Hytopoulos discloses methods for evaluating biological dataset profiles. The datasets comprising information for multiple cellular parameters are compared and identified. A typical dataset comprises readouts from multiple cellular parameters resulting from exposure of cells to biological factors in the absence or presence of a candidate agent. For analysis of multiple context-defined systems, the output data from multiple systems are concatenated. However, Hytopoulos does not outline precise method steps for creating and forming the response profiles. Additionally, Hytopoulos does not provide any working embodiments for practicing the methodology with a biological specimen.

Berg et al. ("Function homology screening." U.S. Pat. No. 8,467,970), which is incorporated by reference herein in parts pertinent thereto, discloses methods for assessing functional homology between drugs. The methods involve exposing cells to drugs and assessing the effect of altering the cellular environment by monitoring multiple output parameters. Two different environments, such as those with different compounds present in the environment, can be directly compared to determine similarities and differences. Based on these comparisons, the compounds can be characterized at a functional level, allowing identification of the pathways and prediction of side effects of the compounds. Berg also discloses a representation of the measured data in the form of a "biomap," which is a very simplified heatmap showing graphically all the measured cellular parameters. Berg is related to measuring biological signaling pathways, rather than physiological responses to stress.

Friend et al. ("Methods of characterizing drug activities using consensus profiles." U.S. Pat. No. 6,801,859), which is incorporated by reference herein in parts pertinent thereto, disclose a method for measuring biological response patterns, such as gene expression patterns, in response to different drug treatments. The response profiles (curves), which are created by exposing biological system to varying concentration of drugs, may describe the biological response of cells to a particular group or class of drugs. The response curves are approximated using models. The resultant data vectors forming curves or profiles, or their parametrical models, can be compared using various measures of similarity. This comparison forms a distance matrix which can be subsequently used in a hierarchical clustering algorithm to build a tree representing the similarity of the profiles. However, the profiles developed by Friend et al. are limited to simple vector-type and parametric mathematical models.

Moreover, profiling methods of the aforementioned applications to Berg et al. and Friend et al. publications are limited and, in particular, do not provide for using distributions for developing profiles of unknown candidate drugs.

Relatively little work in this area has been performed using flow cytometry, which allows for single-cell analysis of cell states on large populations of cells. See, for instance, Edwards et al. ("Flow cytometry for high-throughput, high-content screening." Curr. Opin. Chem. Biol. 8, 392-398, 2004, 2004); Oprea et al. ("Associating Drugs, Targets and Clinical Outcomes into an Integrated Network Affords a New Platform for Computer-Aided Drug Repurposing." Mol. Inform. 30, 100-111, 2011); Robinson et al. ("High-throughput secondary screening at the single-cell level." J. Lab. Autom. 18, 85-98, 2013) and Sklar et al. ("Flow cytometry for drug discovery, receptor pharmacology and high throughput screening." Curr. Opin. Pharmacol. 7, 527-534, 2007), which are incorporated by reference herein in parts pertinent thereto.

However, the recent availability of high-throughput fluidic handling systems for cytometry has made it feasible to process an entire 96- or 384-well plate within few minutes, sampling several thousand cells per well, making cytometry increasingly attractive for high-throughput cell assays. The reports describing the use of high-throughput flow cytometry typically focus on relatively simple assays acquiring from 1 to 5 different variables describing cellular physiology for the analyzed cells. From a mathematical perspective, the data collected in these assays can be described as an array in which the rows store information about individual cells, and the columns describe the measured quantity (e.g. light-scatter characteristics, fluorescence intensity signals, etc.). The measured features can be summarized by a variety of statistics. Most commonly, mean fluorescence intensity in a region of interest is used. After data reduction, the results of an experiment are represented by a vector with elements being the values of the chosen summary statistics. If an experiment involves testing a number of different concentrations of a drug, the final outcome is a 2-D array, with individual columns describing the response curves. Additional parameters (e.g. different times of drug incubation) may be used to add additional dimensions to the array.

Traditionally, drug response curves are approximated by an *a. priori* mathematical model (such as a sigmoidal log-normal curve, log-logistic curve, Gompertz curve, Weibull, etc.) and the measured drug response information is reduced to a few parameters (or even a single parameter) that describe the curves. The entire process produces a heavily abbreviated compound response summary: typically a "signature" comprising a number of EC50 values, that is, values representing a concentration of a compound which induces a response halfway between the baseline and maximum after a specified exposure time.

Such approaches are subject to important inherent limitations that cannot be alleviated easily, if at all. First, they assume the prior existence of a known proper mathematical model with an appropriate parameterization describing the response of all the tested compounds. Second, they presume that a single parameter ($EC_{50}$) derived from a sigmoidal curve carries all the necessary information about the compound response pattern. And third, they analyze the responses manifested by the measured parameters separately, i.e., in a one-dimensional manner. The data analysis and feature extraction leading to formation of the response curves is also problematic.

Furthermore, traditional and well-established cytometric data processing relies on a so-called gating process, which involves manual separation of the populations of interest in order to compute simple statistical features of these populations (mean, median, coefficient of variance, etc.). This gating can be highly subjective, and it is difficult to reproduce in an automated setting. Additionally, the computed features are not scaled or standardized to reflect the range of possible biological responses or the precision of the cytometry measurements.

Embodiments herein described provide methods for overcoming the significant shortcomings of current phenotypic screening methods, in some embodiments, by employing a new methodology for quantifying compound responses. Embodiments described herein provide a number of innovative data acquisition and data processing techniques, which allow meaningful comparisons of multidimensional compound fingerprints without compromising information quality, and without a priori assumptions about responses.

II

A few of the many embodiments encompassed by the present description are summarized in the following numbered paragraphs. The numbered paragraphs are self-referential. In particular, the phase "in accordance with any of the foregoing or the following" used in these paragraphs refers to the other paragraphs. The phrase means, in the following paragraphs, embodiments herein disclosed include both the subject matter described in the individual paragraphs taken alone and the subject matter described by the paragraphs taken in combination. In this regard, it is explicitly applicant's purpose in setting forth the following paragraphs to describe various aspects and embodiments particularly by the paragraphs taken alone or in any combination. That is, the paragraphs are a compact way of setting out and providing explicit written description of all the embodiments encompassed by them individually and in any combination with one another. Applicant specifically reserves the right at any time to claim any subject matter set out in any of the following paragraphs, alone or together with any other subject matter of any one or more of the other paragraphs, including any combination of any values therein set forth, taken alone or in any combination with any other value therein set forth. Should it be required, applicant specifically reserves the right to set forth all of the combinations herein set forth in full in this application or in any successor applications having benefit of this application.

Methods and Analysis

A1. A method for characterizing one or more cellular responses to an agent, comprising:

exposing cell populations to a plurality of concentrations, c, of an agent;

measuring by cytometry a plurality of physiological parameters p, of cells in the population at each concentration;

calculating a set of distances between populations and controls for each parameter for the cell population at each concentration; and compiling one or more tensors for each compound from the calculated distances; and compressing the tensors by tensor decomposition to yield an abbreviated compound fingerprint in the form of a vector.

A2. A method for comparing one or more cellular responses to an agent, comprising:

(A) exposing first cell populations to a plurality of concentrations of a first agent; measuring by cytometry a plurality of physiological parameters, p, of cells in the population at each concentration of said first agent;

compiling one or more tensors from the measurements, thereby describing said first agent;

compressing the tensors(s) via decomposition to obtain an abbreviated compound fingerprint in the form of a vector;

(B) exposing second populations of the cells to a second plurality of concentrations of a second agent;

measuring by cytometry the plurality of physiological parameters of cells in the population at each concentration of said second agent;

compiling one or more tensors from the measurements, thereby describing said second agent;

compressing the tensor(s) via decomposition to obtain abbreviated compound fingerprint(s) in a form of a vector, and (C) calculating a dissimilarity between the first and the second abbreviated fingerprint to determine the difference between the response of the cells to the first and second agents.

A3. A method for determining one or more responses of cells to an agent, comprising:
measuring two or more cell physiology responses for one or more negative, one or more positive controls and for one or more concentrations of a compound;
selecting subpopulations of cells for the controls and the concentration series by mathematical restriction thereby gating the cells in a particular cell cycle compartment and a particular morphological class;
calculating a dissimilarity between the distributions of cellular measurements for each positive and negative control and each of the concentrations;
characterizing the response of the cells to the compound by the calculated dissimilarity.

A4. A method according to any of the foregoing or the following, wherein the responses are calculated using a mathematical metric operating on distributions.

A5. A method in accordance with any of the foregoing or the following, wherein the measurements form a multi-dimensional data point cloud.

A6. A method in accordance with any of the foregoing or the following, wherein changes in multidimensional data point-clouds are calculated as distances by any one or more of a Wasserstein metric, a metric defined as a solution to the Kantorovich-Rubinstein transportation problem, a quadratic-form distance, a quadratic chi-distance, Kullback-Leibler divergence, a Jensen-Shannon divergence, Kolmogorov metric, a Csiszär φ-divergence, a Burbea and Rao divergence, and Bregman divergence.

A7. A method according to any of the foregoing or the following, wherein the value at 95-percentile of the pairwise distances within a group of controls is chosen as the limit of measurement precision (limit of statistical significance).

A8. A method according to any of the foregoing or the following, wherein a robust measure of dissimilarity between group of positive controls and a group of negative controls defines a unit of dissimilarity between the responses.

A9. A method in accordance with any of the foregoing or the following, comprising quantitating the changes in distribution of the measured multidimensional data point-clouds at a plurality of different concentrations of the compound.

A10. A method in accordance with any of the foregoing or the following, further employing dimensionality reduction by summarizing features from a plurality of response tables wherein every response vector is summarized by a number of derived quantities smaller than the number of concentrations of said compound.

A11. A method in accordance with any of the foregoing or the following, further representing a response to an agent by a multiway tensor comprising summarizing features.

A12. A method in accordance with any of the foregoing or the following, wherein tensors calculated for different agents are compared to each other by computing a dissimilarity measure.

A13. A method in accordance with any of the foregoing or the following, wherein tensors are decomposed using one or more of Tucker decomposition, CANDECOMP, PARAFAC, PARAFAC2, INDSCAL, CANDELINC, DEDICOM or PARATUCK2 decompositions.

Tensors and State Tensors

TSt1. A cellular response tensor in accordance with any of the foregoing or the following, wherein the response tensor is generated from a dataset of measured values of a plurality of two or more cell physiology parameters, wherein the response tensor quantifies a multiparametric and multifactorial cellular phenotype.

TSt2. A cellular response tensor in accordance with any of the foregoing or the following encoded in a tangible form so that it can be accessed, copied, used and/or retrieved in whole or in part by a user.

TSt3. A cellular response tensor in accordance with any of the foregoing or the following, wherein a response tensor for a control dataset provides the basis for determining whether a test dataset is different from a control or a profile dataset.

Controls

Ctr1. A method according to any of the foregoing or the following, where positive control cells are treated with one or more known compounds that trigger a maximal measurable effect on one or more of the measured cell physiology responses.

Ctr2. A method according to any of the foregoing or the following, wherein the negative controls are untreated cells, cells treated with buffer, cells treated with media, or cells treated with a sham compound Cell Cycle Ccy1. A method in accordance with any of the foregoing or the following, wherein the cell state is a measurement of growth phase of the cells, preferably, a measurement of cell division.

Ccy2. The method in accordance with any of the foregoing or the following, wherein the cell state or cell cycle stage is detected via flow cytometry at single-cell level.

Ccy3. A method according to any of the foregoing or the following, where one of the physiological parameters is the cell cycle.

Ccy4. A method according to any of the foregoing or the following, wherein one of the physiological parameter is cells cycle compartment G1, S, G2 and M.

Ccy5. A method according to any of the foregoing or the following, wherein one of the cell cycle compartments is G1, S, and G2/M.

Ccy6. A method according to any of the foregoing or the following, wherein all of the physiological responses are measured as a function of cell cycle compartment.

Ccy7. A method in accordance with any of the foregoing or the following, wherein cell cycle phases are measured using fluorescence labels.

Ccy8. A method in accordance with any of the foregoing or the following, wherein cell cycle phases are measured using one or more fluorescent DNA intercalating dyes.

Ccy9. A method in accordance with any of the foregoing or the following, wherein cell cycle phases are measured using one or more of the fluorescent intercalating dyes HOECHST 33342(2'-(4-Ethoxyphenyl)-6-(4-methyl-1-piperazinyl)-1H,3'H-2,5'-bibenzimidazole), DRAQ5™ (1,5-bis{[2-(di-methylamino) ethyl]amino}-4, 8-dihydroxyanthracene-9,10-dione), YO—PRO-1 IODIDE (Quinolinium, 4-((3-methyl-2(3H)-benzoxazolylidene)methyl)-1-(3-(trimethylammonio) propyl)-, diIODIDE), DAPI (4', 6-diamidino-2-phenylindole) and CYTRAK ORANGE (derivative of 1,5-bis{[2-(di-methylamino) ethyl]amino}-4, 8-dihydroxyanthracene-9,10-dione).

Ccy10. A method in accordance with any of the foregoing or the following, wherein cells cycle phases are measured by immunolabelling of cell cycle-dependent proteins.

Ccy11. A method in accordance with any of the foregoing or the following, wherein cell cycle phases are measured by immunolabelling one or more of cyclins A, cyclin B and cyclin E.

Ccy12. A method in accordance with any of the foregoing or the following, wherein cell cycle phases are measured by immunolabelling one or more phosphorylated histone proteins.

Ccy13. A method in accordance with any of the foregoing or the following, wherein cell cycle phases are using genetically encoded cell-cycle dependent fluorochromes, e.g., hyper-phosphorylated Rb protein and cell cycle can be measured by flow cytometry (see Juan et al. "Phosphorylation of retinoblastoma susceptibility gene protein assayed in individual lymphocytes during their mitogenic stimulation," *Experimental Cell Res* 239: 104-110, 1998, which is incorporated by reference herein in parts pertinent thereto) and cyclin protein expression (or their phosphorylation status) can be monitored using flow cytometry (see Darzynkiewicz et al. "Cytometry of cell cycle regulatory proteins." Chapter in: *Progress in Cell Cycle Research* 5;533-542, 2003, which is incorporated by reference herein in parts pertinent thereto).

Ccy14. A method in accordance with any of the foregoing or the following, wherein cell cycle phases are measured by expression of a genetically encoded fusion protein comprising a naturally expressed oscillating protein linked to a fluorescent protein moiety, e.g., cell cycle arrest at G2/M (Cheng et al., "Cell-cycle arrest at G2/M and proliferation inhibition by adenovirus-expressed mitofusin-2 gene in human colorectal cancer cell lines," Neoplasma 60; 620-626, 2013); regulation of S-phase entry (McGowan et al., "Platelet-derived growth factor-A regulates lung fibroblast S-phase entry through p27kip1 and FoxO3a," *Respiratory Research*, 14;68-81, 2013); or identification of live proliferating cells using a cyclinB1-GFP fusion reporter (see Klochendler et al., "A transgenic mouse marking live replicating cells reveals in vivo transcriptional program of proliferation," *Developmental Cell*, 16;681-690, 2012). The disclosures in these publications are incorporated by reference herein in parts pertinent thereto.

Ccy15. A method in accordance with any of the foregoing or the following, wherein the cell cycle is altered by an agent Ccy16. A method in accordance with any of the foregoing or the following, wherein the cell cycle is altered by a variation in cell culturing method.

Ccy17. A method in accordance with any of the foregoing or the following, wherein the cell cycle is altered by changes in the levels of one or more of the following in the culture medium: glucose, essential and non-essential amino acids, $O_2$ concentration, pH, galastose and/or glutamine/glutamate.

Ccy18. The method in accordance with any of the foregoing or the following, further comprising detecting the cell state or cell cycle stage in a control population of cells exposed to a plurality of chemicals or agents which are known to perturb the state of the cell cycle.

Cells

Cls1. A method in accordance with any of the foregoing or the following, wherein the cells are in vitro cultured cells.

A method in accordance with any of the foregoing or the following, wherein the cells are biopsy cells.

Cls2. A method in accordance with any of the foregoing or the following, wherein the cells are live cells.

Cls3. A method in accordance with any of the foregoing or the following, wherein the cells are fixed cells.

Cls4. A method in accordance with any of the foregoing or the following, wherein the cells are a cell line.

Cls5. A method in accordance with any of the foregoing or the following, wherein the cells characteristic of a naturally occurring healthy cell type.

Cls6. A method in accordance with any of the foregoing or the following, wherein the cells are characteristic of a disease.

Cls7. A method in accordance with any of the foregoing or the following, wherein the cells are characteristic of an inborn genetic disorder.

Cls8. A method in accordance with any of the foregoing or the following, wherein the cells are characteristic of a cancer.

Cls9. A method according to any of the foregoing or the following, wherein the cells are characteristic of a metabolic disorder.

Cls10. A method in accordance with any of the foregoing or the following, wherein the cells are animal cells.

Cls11. A method in accordance with any of the foregoing or the following, wherein the cells are mammalian cells.

Cls12. A method in accordance with any of the foregoing or the following, wherein the cells are human cells.

Cls13. A method according to any of the foregoing or the following, wherein the cells are germ cells or stem cells, including, pluripotent stem cells.

Cls14. A method in accordance with any of the foregoing or the following, wherein the cells are somatic cells.

Cls15. A method in accordance with any of the foregoing or the following, wherein the cells are stem cells.

Cls16. A method in accordance with any of the foregoing or the following, wherein the cells are embryonic stem cells.

Cls17. A method in accordance with any of the foregoing or the following, wherein the cells are pluripotent stem cells.

Cls18. A method in accordance with any of the foregoing or the following, wherein the cells are induced pluripotent stem cells.

Cls19. A method in accordance with any of the foregoing or the following, wherein the cells are blast cells.

Cls20. A method in accordance with any of the foregoing or the following, wherein the cells are differentiated cells.

Cls21 A method in accordance with any of the foregoing or the following, wherein the cells are terminally differentiated somatic cells.

Cls22. A method in accordance with any of the foregoing or the following, wherein the cells are cardiomyocytes, hepatocytes, neurons or a combination thereof.

Cls23 A method in accordance with any of the foregoing or the following, wherein the cells are one or more of the following cells: primary cells, transformed cells, stem cells, insect cells, yeast cells, preferably anchorage independent cells, such as, for example, human hematopoietic cell lines (including, but not limited to, HL-60, K562, CCRF-CEM, Jurkat, THP-1, etc.); or anchorage-dependent cell lines (including, but not limited to HT-29 (colon), T-24 (bladder), SKBR (breast), PC-3 (prostate), etc.).

Duration

Dur1. A method in accordance with any of the foregoing or the following, wherein cells are exposed to an agent for a plurality of durations or various times, e.g., measuring time course (kinetics) for activation of signaling pathways in cells (see, e.g., Woost et al., "High-resolution kinetics of cytokine signaling in human CD34/CD117-positive cells in unfractionated bone marrow," Blood, 117; 131-141, 2011, which is incorporated by reference herein in parts pertinent thereto). Embodiments involving analysis of kinetics is preferred over embodiments which do not require such analysis (see Kornblau et al. "Dynamic single-cell network profiles in acute myelogenous leukemia are associated with patient response to standard induction therapy," *Clin Cancer Res,* 16;3721-3733, 2010, which does not teach kinetic analysis).

Dur2. A method in accordance with any of the foregoing or the following, wherein the cells are exposed to an agent for 0.1, 0.2, 0.3, 0.4, 0.5, 0.6, 0.7, 0.8, 0.9, 1, 2, 3, 4, 5, 6, 7, 8, 9, 10, 12, 14, 15, 16, 18, 20, 22, 24, 26, 28, 30, 35, 40, 44, 48, 52, 56, 60, 66, 72, 78 or more hours or any combination thereof.

Concentration

Cnc1. A method in accordance with any of the foregoing or the following, wherein a plurality of two or more concentration series of an agent Plurality (Number) of Samples Plr1. A method in accordance with any of the foregoing or the following, comprising wherein a plurality of samples are measured.

Plr2. A method according to any of the foregoing or the following, comprising measuring a plurality of samples disposed in wells of a multiwell plate.

Plr3. A method according to any of the foregoing or the following, comprising measuring a plurality of samples disposed in wells of 96, 384, or 1536-well plate.

Basic Instrumentation/Methods

Ins1. A method in accordance with any of the foregoing or the following, wherein the responses are measured by cytometry.

Ins2. A method in accordance with any of the foregoing or the following, wherein the responses are measured by flow cytometry.

Ins3. A method in accordance with any of the foregoing or the following, wherein responses are measured by flow cytometry of live cells.

Ins4. A method in accordance with any of the foregoing or the following, wherein responses are measured by flow cytometry of fixed cells.

Ins5. A method in accordance with any of the foregoing or the following, wherein responses are measured by imaging of immobilized cells.

Ins6. A method in accordance with any of the foregoing or the following, wherein responses are measured by fluorimetry.

Ins7. A method in accordance with any of the foregoing or the following, wherein a plurality of two or more response parameters is measured by a multichannel sensor array.

Signal Processing

Sig1. A method in accordance with any of the foregoing or the following, comprising decorrelating fluorescence signals via linear unmixing of the acquired signals by multiplying the vector of measured values by an inverse of the matrix containing in its columns the spectra of the employed fluorescent species; the said matrix being normalized per column to 1

Sig2. A method in accordance with any of the foregoing or the following, comprising decorrelating fluorescence signals via linear unmixing of the acquired signals by multiplying the vector of measured values by an inverse of the matrix containing in its columns the spectra of the employed fluorescent species; the said matrix being normalized per diagonal to 1

Agents

Agt1. A method in accordance with any of the foregoing or the following, wherein the cells are exposed to a single compound.

Agt2. A method in accordance with any of the foregoing or the following wherein the cells are exposed to two or more compounds.

Agt3. A method in accordance with any of the foregoing or the following wherein one or more of the compounds stimulate a physiological response.

Agt4. A method in accordance with any of the foregoing or the following, wherein the agent may be a genetic agent, e.g. expressed coding sequence; or a chemical agent, e.g. drug candidate.

Physiological Parameters

MMP

MMP1. A method in accordance with any of the foregoing or the following, wherein mitochondrial toxicity is measured.

MMP2. A method in accordance with any of the foregoing or the following, wherein the loss of mitochondrial membrane potential or integrity is measured.

MMP3. A method in accordance with any of the foregoing or the following, wherein loss of mitochondrial membrane potential or integrity is measured using a fluorescent dye.

MMP4. A method in accordance with any of the foregoing or the following, wherein loss of mitochondrial membrane potential or integrity is measured using one or more of JC-1 (5,5',6,6'-tetrachloro-1,1',3,3'-tetraethyl-benzimi-dazolylcarbocyanine IODIDE), JC-9 ((3,3'-dimethyl-β-naphthoxazolium IODIDE, MITO-PROBE™, Molecular Probes), JC-10 (e.g., derivative of JC-1), DiOC2(3) ((3,3'-diethyloxacarbocyanine IODIDE; MITOPROBE™, Molecular Probes), DiIC1 (5) ((1,1',3,3,3',3'-hexamethylindodicarbo—cyanine IODIDE; MITOPROBE™, Molecular Probes), MITOTRACKER™ (Molecular Probes), ORANGE CMTMROS (chloromethyl-dichlorodihydrofluorescein diacetate, MITOTRACKER™ ORANGE, Molecular Probes) and CMXROS (1H,5H,11H,15H-Xantheno[2,3,4-ij:5,6,7-i'j']diquinolizin-18-ium, 9-[4-(chloromethyl)phenyl]-2,3,6,7,12,13,16,17-octa-hydro-, chloride, MITOTRACKER™ RED, Molecular Probes).

Light Scattering

LSg1. A method in accordance with any of the foregoing or the following, wherein a physiological parameter of cell state is measured by light-scattering.

LSg2. A method in accordance with any of the foregoing or the following, wherein a physiological parameter of cell state is measured by laser light-scattering.

LSg3. A method in accordance with any of the foregoing or the following, wherein a physiological parameter of cell state is measured by quantifying the amount of laser light scattered from individual cell at two or more angles.

LSg4. A method in accordance with any of the foregoing or the following, wherein a physiological parameter of cell state is measured by laser light-scattering.

LSg5. A method in accordance with any of the foregoing or the following, wherein a physiological parameter of cell state is measured by laser light-scattering, wherein the wavelength of light emitted by the laser is within the range of any one or more of 403-408 nm, 483-493 nm, 525-535 nm, 635-635 nm and 640-650 nm.

Cell Viability

Via1. A method in accordance with any of the foregoing or the following, wherein cell viability is measured.

Via2. A method in accordance with any of the foregoing or the following, wherein cell membrane integrity is measured.

Via3. A method in accordance with any of the foregoing or the following, wherein cell viability is determined my measuring membrane integrity.

Via4. A method in accordance with any of the foregoing or the following, wherein loss of membrane integrity is detected using a dye.

Via5. A method in accordance with any of the foregoing or the following, wherein loss of membrane integrity is detected using a dye that enters cells with damaged membranes characteristic of dying or dead cells but does not enter cells with intact membranes characteristic of live cells.

Via6. A method in accordance with any of the foregoing or the following, wherein loss of membrane integrity is detected using a dye that enters cells with damaged membranes characteristic of dying or dead cells but does not enter cells with intact membranes characteristic of live cells, wherein the dye fluoresces on binding to DNA.

Via7. A method in accordance with any of the foregoing or the following, wherein loss of membrane integrity is detected using one or more of the following dyes: PROPIDIUM IODIDE, DAPI and 7-aminoactinomycin D.

Via8. A method in accordance with any of the foregoing or the following, wherein membrane integrity is measured using one or more dyes that cross intact cell membranes and fluorescence upon interacting with intracellular enzymes and remain in the cytoplasm of live cells but diffuse out of lacking an intact cytoplasmic membranes.

Via9. A method in accordance with any of the foregoing or the following, wherein membrane integrity is measured using one or more dyes that cross intact cell membranes and fluorescence upon interacting with intracellular enzymes and remain in the cytoplasm of live cells but diffuse out of cells lacking an intact cytoplasmic membrane, wherein the dyes are one or more of fluorescein diacetate, CALCEIN AM, BCECF AM, carboxyeosin diacetate, CELLTRACKER™ GREEN CMFDA, Chloromethyl SNARF-1 acetate and OREGON GREEEN 488 carboxylic acid diacetate).

Via10. A method in accordance with any of the foregoing or the following, wherein viability is measured by any one or more of Annexin V, cleaved capases/caspase activation, including phosphorylation and/or nuclear lamin degradation.

GLU, ROS, MMP, CMP and Viability

GRC1. A method in accordance with any of the foregoing or the following, wherein one or more of the following physiological parameters is measured: glutathione concentration ("GLU"), free radicals and/or reactive oxygen species ("ROS"), mitochondrial membrane potential/permeability ("MMP"), cytoplasmic membrane permeability, and cell viability.

DNA Damage, Stress, Inflammation, Metabolism, Apotosis

DSI1. A method in accordance with any of the foregoing or the following, wherein one or more the following physiological parameters is measured: DNA damage; a stress response signaling pathway constituent; an inflammatory response pathway constituent; a metabolic pathway regulatory constituent or an apotosis pathway constituent.

DSI2. A method in accordance with any of the foregoing or the following, wherein the stress response signaling pathway constituent SAPK is measured.

DSI3. A method in accordance with any of the foregoing or the following, wherein the inflammatory responses signaling pathway constituent NF-kB is measured.

DSI4. A method in accordance with any of the foregoing or the following, wherein the metabolic pathway regulatory constituent measured is a lipid peroxidases, GSk3B, and/or ribosomal S6 kinase.

DSI5. A method in accordance with any of the foregoing or the following, wherein the apotic pathway constituent measured is $\beta$13K, AKT and/or a Bcl-family protein.

Reference Banks

Rbk1. A method in accordance with any of the foregoing or the following, wherein the known perturbing chemicals or exogenous molecular agents are further subgrouped based on their known effects.

Rbk2. A method in accordance with any of the foregoing or the following, further comprising creating response tables comprising information about changes in cell viability, mitochondrial toxicity, and at least one additional physiological or phenotypic descriptor at every employed concentration of said compound computed for every stage of cell cycle defined by cell-cycle dependent markers.

Rbk3. A method in accordance with any of the foregoing or the following, wherein tensors describing known compounds used to treat a particular disease are grouped into a single defined class or a plurality of defined classes and the compound tensors are used as a training set for a supervised learning which classifies unknown or not previously characterized compounds into said defined classes.

Rbk4 A method in accordance with any of the foregoing or the following, wherein tensors describing known compounds are grouped into classes on the basis of their off-target responses, such as, side-effects.

Rbk5. The method in accordance with any of the foregoing or the following, wherein feature tensors are used to discover clusters of similar compound using unsupervised learning.

Rbk6. The method in accordance with any of the foregoing or the following, wherein the feature tensors are vectorized.

Classification of Agent Action

Cls1. A method for classifying biologically active compounds in accordance with any comprising detecting a plurality of cellular features from a population of cells exposed to said compounds, wherein said features are correlated to morphological properties quantified simultaneously by proportions of light scatter intensity measured at two or more angles.

Cls2. A method in accordance with any of the foregoing or the following, comprising exposing a culture of said population of cells to a plurality of compounds and detecting the physiological response of said population of cells in the presence and absence of said compound.

Cls3 A method in accordance with any of the foregoing or the following, comprising detecting the physiological response of individual cells sampled from said culture Cls4. A method in accordance with any of the foregoing or the following, wherein the physiological response is mitochondrial toxicity, which is quantitated in terms of loss of mitochondrial membrane potential or a loss of mitochondrial membrane integrity using one or more fluorescence labels selected from the group consisting of JC-1, JC-9, JC-10, DiOC2(3), DiIC1(5), MITO TRACKER® ORANGE CMTMROS, MITO TRACKER® RED CMXROS.

Cls5. A method in accordance with any of the foregoing or the following, wherein the physiological response is overall cell viability, which is quantitated in terms of loss of cellular membrane integrity using one or more fluorescence labels.

Cls6. A method in accordance with any of the foregoing or the following, wherein the fluorescence labels are selected from groups consisting of dyes which enter the cell interior resulting in a very bright fluorescence (e.g., propidium IODIDE and 7-aminoactinomycin D);

dyes which cross membranes of intact cell membranes and produce fluorescent molecule upon interaction with intracellular enzymes (e.g., fluorescein diacetate, CALCEIN AM, BCECF AM, carboxyeosin diacetate, CELLTRACKER™ GREEN CMFDA, Chloromethyl SNARF-1 acetate, OREGON GREEN 488 carboxylic acid diacetate).

Cls7. A method in accordance with any of the foregoing or the following, further comprising detecting at least one additional physiological or phenotypic descriptor from the group consisting of concentration of glutathione, presence of reactive oxygen species or free radicals, Systems Sys1. A system for evaluating/comparing biological datasets, comprising a non-transitory computer readable storage medium storing a computer program that, when executed on a computer, causes the computer to perform any of the foregoing or following methods.

Sys2. A system for evaluating/comparing biological datasets, comprising a non-transitory computer readable storage medium storing a computer program that, when executed on a computer, causes the computer to perform any of the foregoing or following methods for characterizing one or more cellular responses to an agent, said method comprising:

measuring by cytometry a plurality of physiological parameters p, of cells in the population which are exposed to a concentration, c, of said agent;

calculating a set of distances between populations and controls for each parameter for the cell population at each concentration; and compiling a tensor or a set of tensors for each compound (where the tensors contain compound fingerprints); and compressing the tensors via tensor decomposition to yield an abbreviated compound fingerprint in a form of a vector.

Sys3. A computer system for evaluating/comparing biological datasets, comprising, a non-transitory computer readable storage medium storing a computer program that, when executed on a computer, causes the computer to perform a method for characterizing one or more cellular responses to an agent, said method comprising:

(A) exposing first cell populations to a plurality of concentrations, c, of a first agent;

measuring by cytometry a plurality of physiological parameters p, of cells in the population at each concentration of said first agent;

compiling one or more tensors from describing said first agent;

compressing the fingerprint tensors(s) via decomposition to obtain abbreviated compound fingerprint in a form of a vector;

(B) exposing second cell populations to a second plurality of concentrations, c2, of a second agent;

measuring by cytometry a plurality of physiological parameters p, of cells in the population at each concentration of said second agent;

compiling one or more tensors from describing said second agent;

compressing the fingerprint tensors(s) via decomposition to obtain abbreviated compound fingerprint in a form of a vector and (C) calculating a dissimilarity between the first and the second abbreviated fingerprint to determine the difference between the response of the cells to the first and second agents.

Sys4. A computer system for evaluating/comparing biological datasets, comprising, a non-transitory computer readable storage medium storing a computer program that, when executed on a computer, causes the computer to perform a method for characterizing one or more cellular responses to an agent, said method comprising:

measuring two or more cell physiology responses for one or more negative, one or more positive controls and for one or more concentrations of a compound;

selecting subpopulation of cells for the controls and the concentration series by gating the cells in a particular cell cycle compartments and a particular morphological class;

calculating a dissimilarity between the distributions of cellular measurements for each positive and negative controls and each of the concentrations;

thereby to determine the response of the cells to the compound.

Datasets and Databases

Dbs1. A dataset comprising values for two or more cellular parameters

Dbs2. A dataset comprising measured values for multiple cellular parameters for cells exposed to biological factors in the absence or presence of a candidate agent.

Dbs3. A database comprising compound fingerprint datasets in form of compound response tensors.

Dbs4. A database of trusted profiles for the identification of test profiles, where the trusted profile is a response tensor of an *a. priori* known and well-characterized compound.

Dbs5. Datasets may be control datasets, or test datasets, or profile datasets that reflect the parameter changes of known agents. For analysis of multiple context-defined systems, the output data from multiple systems may be concatenated.

Fingerprint

Fpt1. A drug fingerprint comprising value of multiple cell response parameters.

Fpt2. A drug fingerprint of a genus of compounds, comprising an average of repeated measurements of state tensors, Fpt2. A drug fingerprint of a genus of compounds, comprising vector or a matrix produced by a tensor decomposition where said tensor contained measurements of multiple compounds,

III

BRIEF DESCRIPTION OF THE DRAWINGS

Various features and advantages of the embodiments herein described can be fully appreciated as the same becomes better understood when considered in light of the accompanying drawings.

The upper left panel shows a clear delineation of cells in G1, S, and G/2M stages of the cycle by DNA staining (as described above for FIG. 5).

The top right panel shows results for phosphorylated histone H3 ("P—H3") measured using an P-H3 antibody conjugated to ALEXA FLUOR® 647 as a function of the cell cycle. DNA content was measured as for the upper left panel. The results show that P—H3 is expressed only in G2/M.

The bottom two panels show results for Cyclin A2 measured using an anti-A2 antibody conjugated to PE as a function of the cell cycle. DNA content was measured as for the upper left panel. Cyclin A2 increases as cells progress through S and form two populations of differing Cyclin A2 expression in G2/M.

The lower right panel shows results for Cyclin A2 versus those for P—H3 during cell progression through late S, to G2, to M.

By "gating" the subsequent analysis on only these cell cycle populations (using DNA content), it is evident that P—H3 is first expressed in cells with the highest Cyclin A2 levels (G2 population), that P—H3 is maintained at high levels while Cyclin A2 is degraded, and that P—H3 is then "lost" (by de-phosphorylation of the specific Serine residue that was phosphorylated upon entry into G2) as cells progress from mitosis (M) back into G1. In traditional flow cytometric analysis, these sequences of changes in protein expression are established by careful manual "gating" (selecting) different cell populations (based on DNA content) and subsequently analyzing the expression of protein (or other targets defined by different antibody-conjugates).

Figure 8:
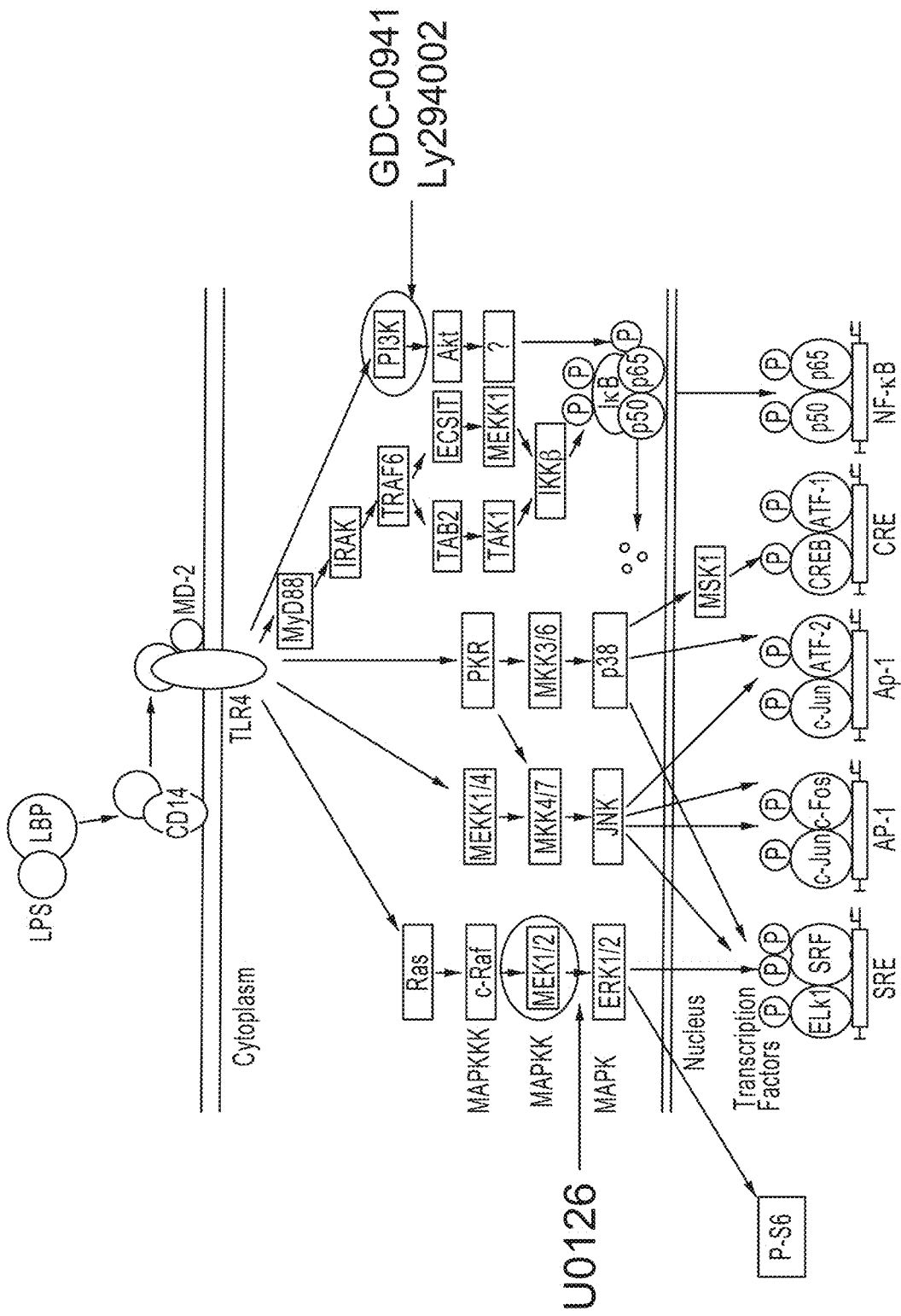

FIG. 8 shows an example of signal transduction pathways downstream of Toll-like receptor 4 (TLR4) found on peripheral blood monocytes. The representative inhibitors of β13 kinase (PI3K) and mitogen-associated protein kinase kinase (MAPKK) pathways are indicated by arrows.

Figure 9:
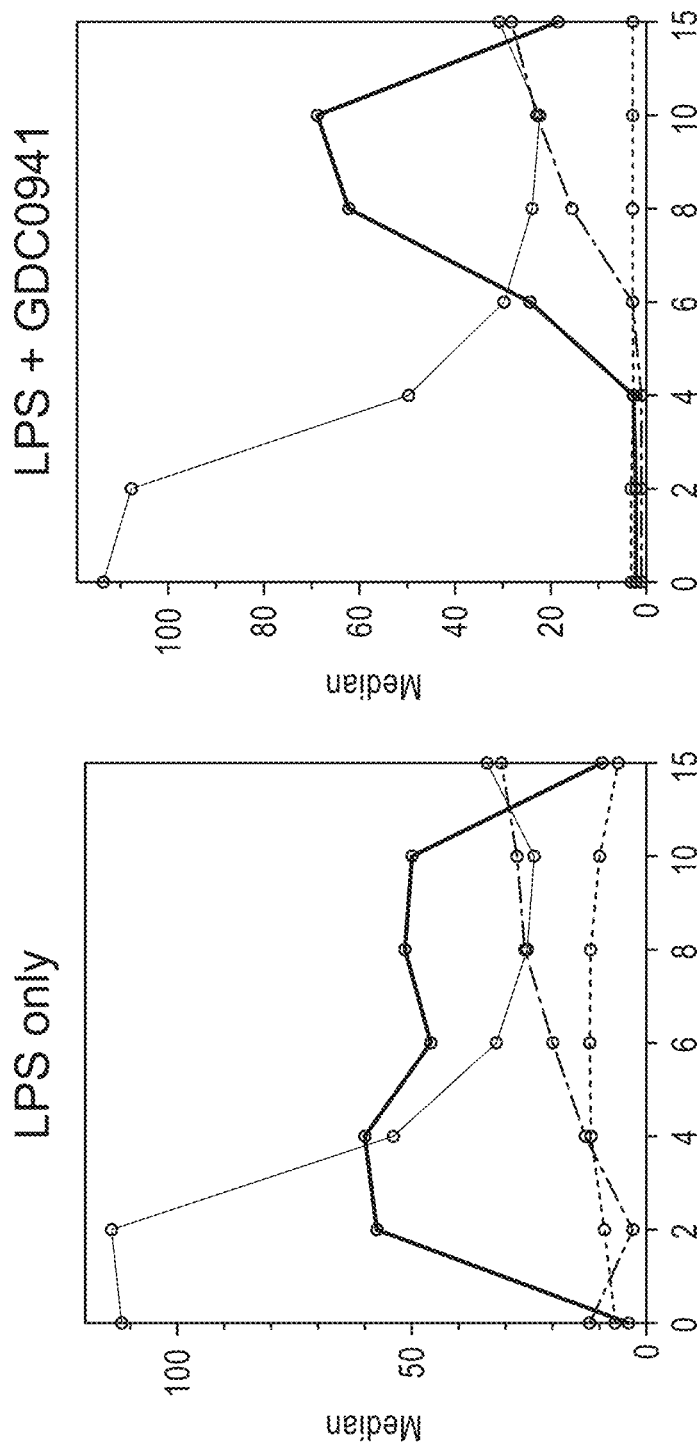

FIG. 9 shows kinetics (in minutes) of signal transduction responses in human peripheral blood monocytes to LPS in absence (left panel) and in the presence of the PI3 kinase inhibitor GDC0941, as described in Example 6.

Green—IκBα; Red-P-ERK; Orange—P-Akt; Blue—P-S6.

As can be seen in the left hand panel, LPS treatment activates the Iκ kinase (results in the proteasomal degradation of IκBα—loss of green/ALEXA FLUOR® 488 fluorescence signal), and activates (phosphorylates) ERK, Akt and S6 (individual phosphoproteins detected by flow cytometry using antibodies to P-ERK, P-Akt, and P-S6 conjugated with ALEXA FLUOR® 647, PE, and Pacific Blue, respectively).

The right hand panel shows that in the presence of the PI3 kinase inhibitor GDC0941, P-Akt is not phosphorylated, and the kinetics of ERK and S6 phosphorylation are delayed, compared to the control cells treated with LPS alone (left hand panel). It is further shown that PI3K inhibition has no impact on the proteasomal degradation of IκBα.

Figure 10:
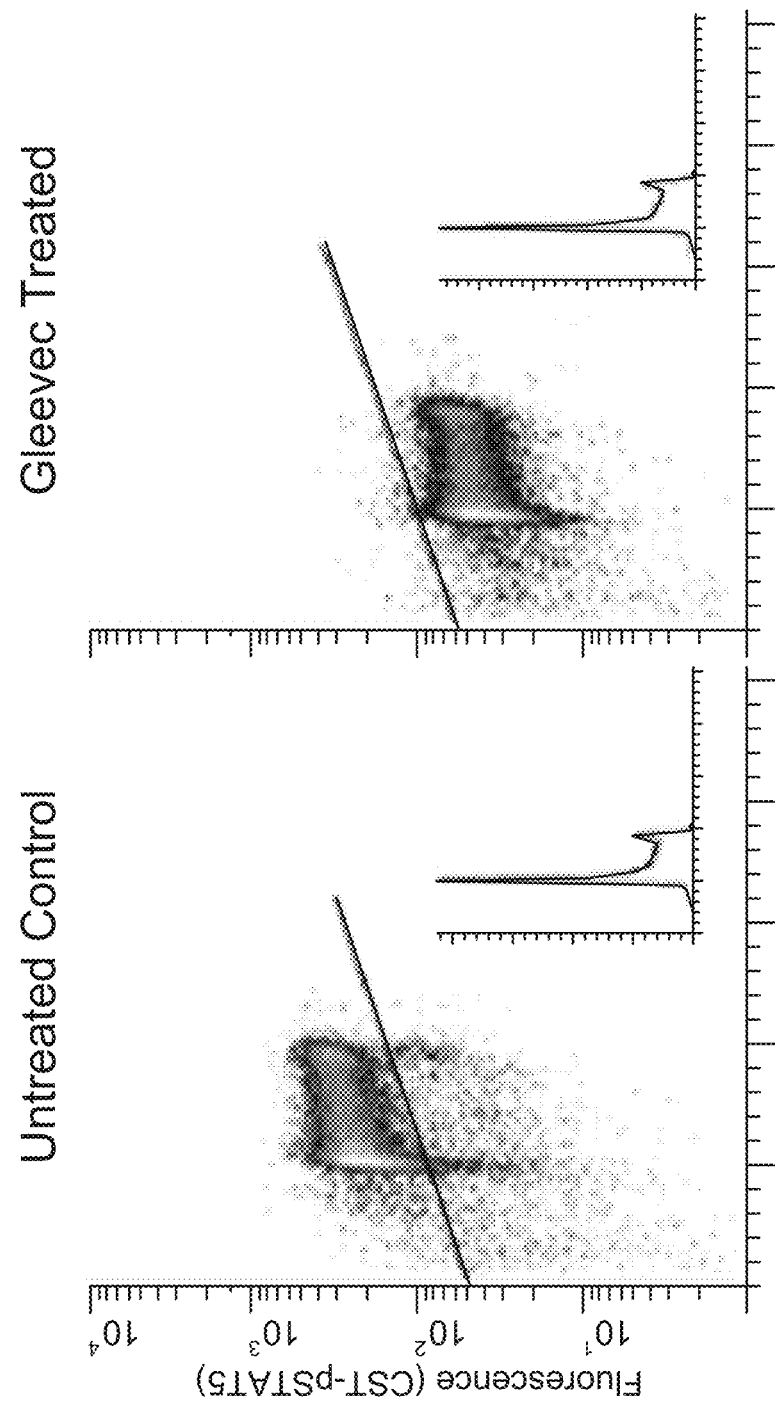

FIG. 10 shows the effect of exposing cells to GLEEVEC™ (imatinib, or STI571), the details of which are provided in Example 7. As can be seen from the figure, treatment of K562 cells for 30 min with 2 µM results in >95% inhibition of the phosphorylation of the downstream STAT5 target. Phosphorylated STAT5 acts as a transcriptional activator of several target proteins, including Cyclin D, and constitutive expression of Cyclin D maintains K562 cells in cell cycle.

As can be seen in the Figure, although the phosphorylation of STAT5 is inhibited after 30 min imatinib exposure (as demonstrated by a shift in the total population of cells that are P-Stat5 positive from above the threshold line to below the threshold line in GLEEVEC-treated cells), there is no concomitant change in the cell cycle, as measured by DNA content (see inset).

Figure 11:
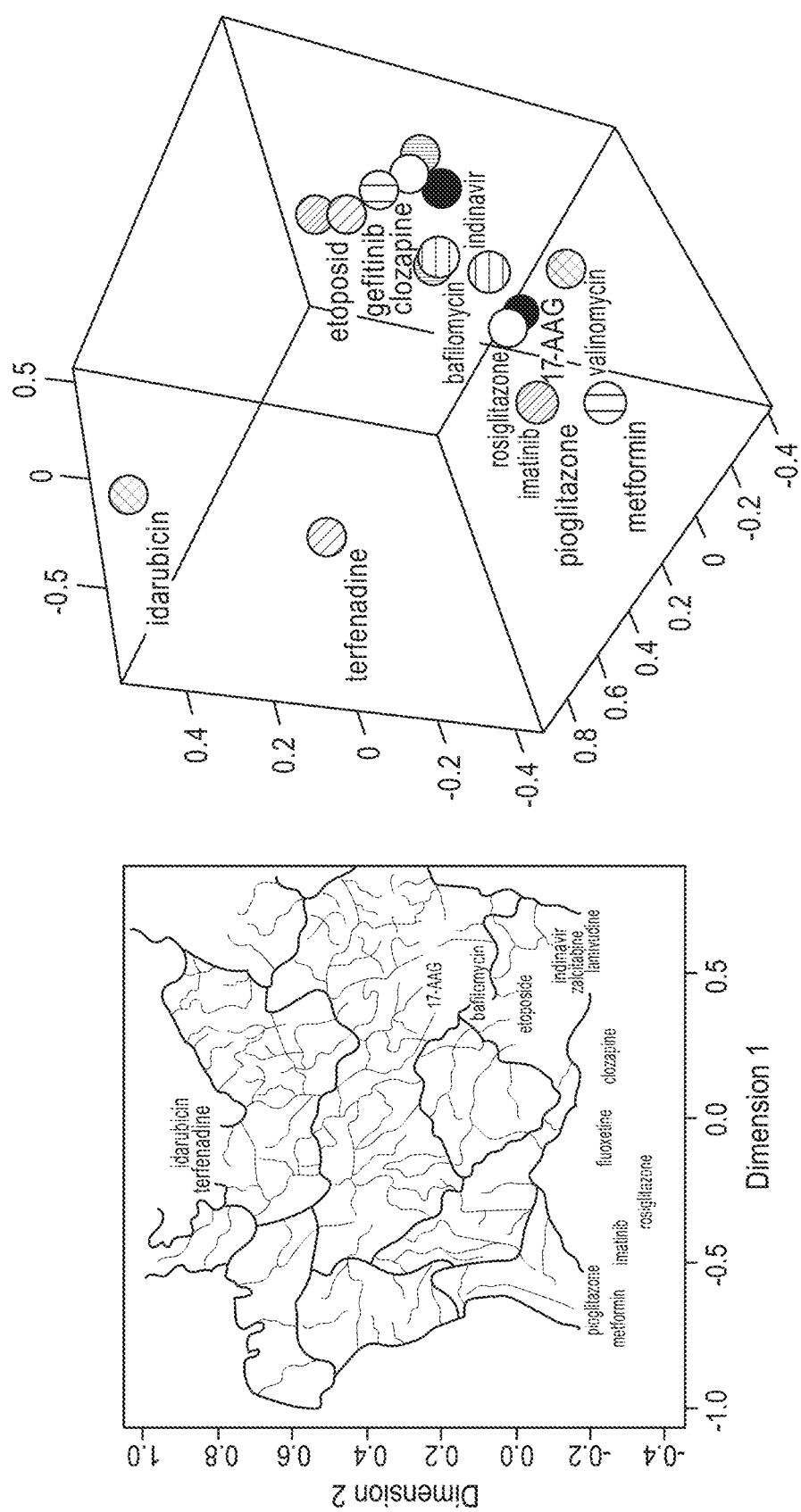

FIG. 11 provides an example in two dimensions and three dimensions of a multi-way MDS visualization of response data showing that compounds which appear to be close together in two dimensions may actually be distant from one another when mapped in three or more dimensions.

Figure 12:
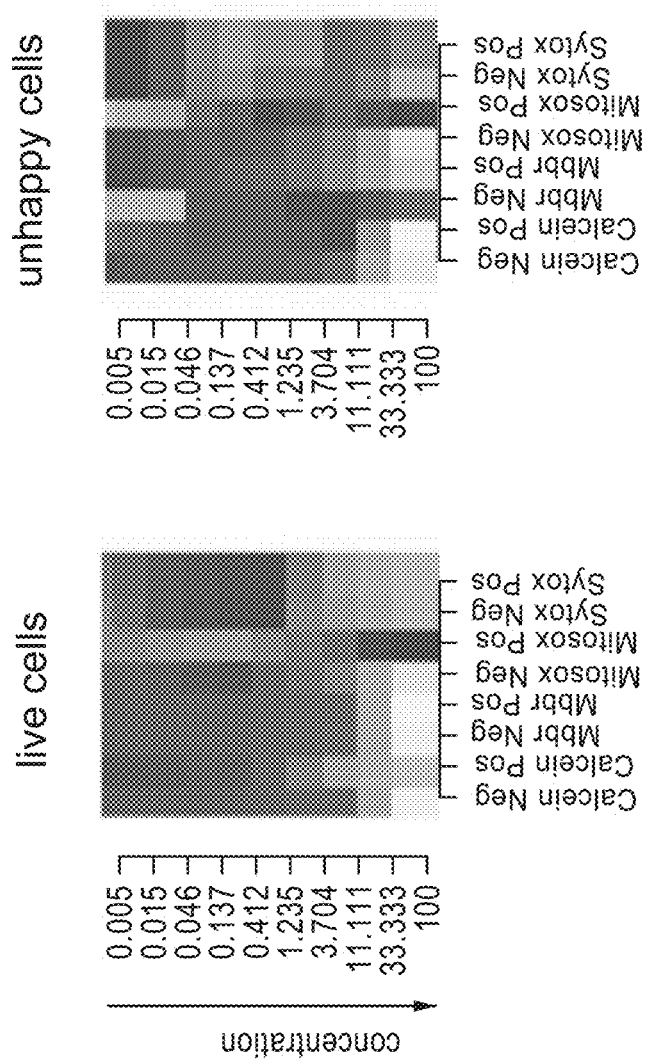

FIG. 12 shows a drug fingerprint for the anti-diabetic drug troglitazone, the details of which are outlined in Example 8.

Figure 13:
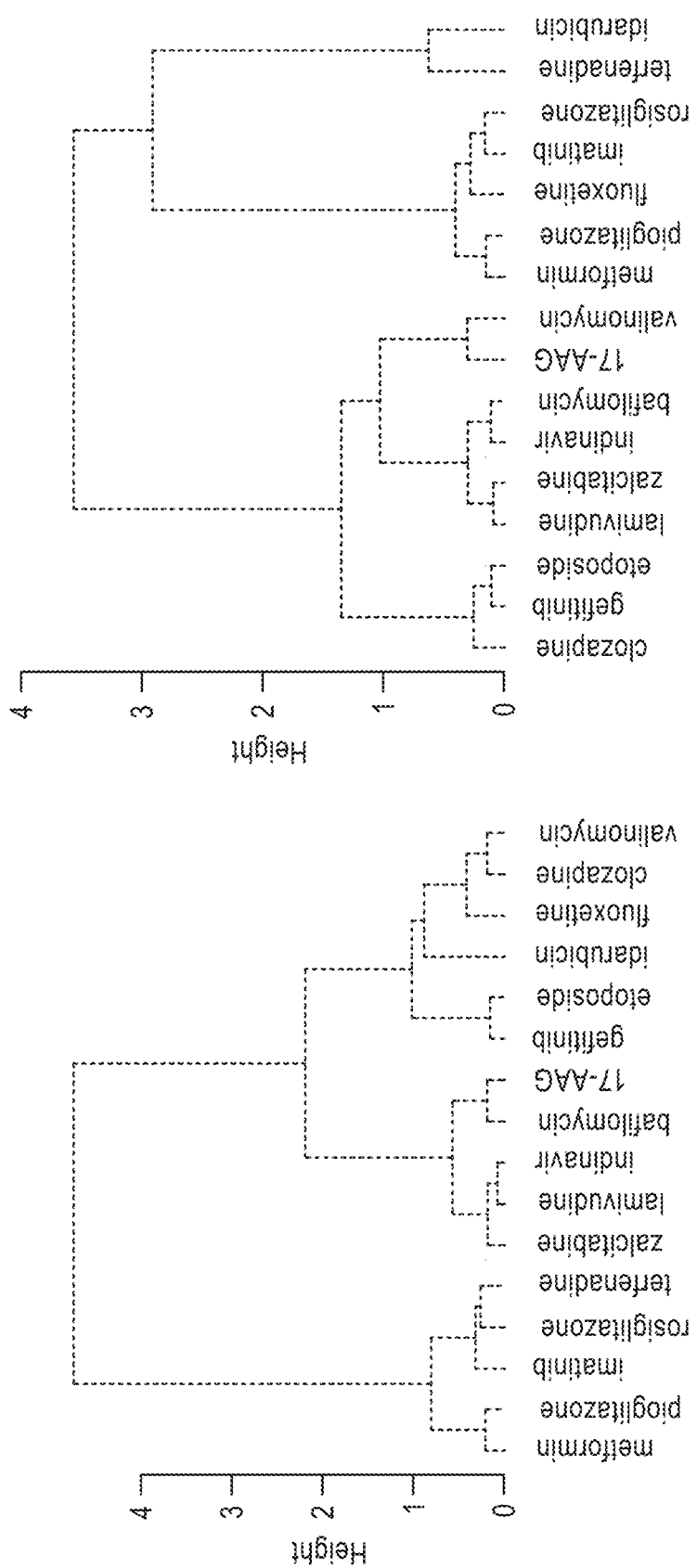

FIG. 13 shows representative dendograms for visualizing physiological similarities between various drugs based on the cellular phenotype (e.g., cellular and nuclear membrane integrity or presence of ROS) that is analyzed.

Figure 14:
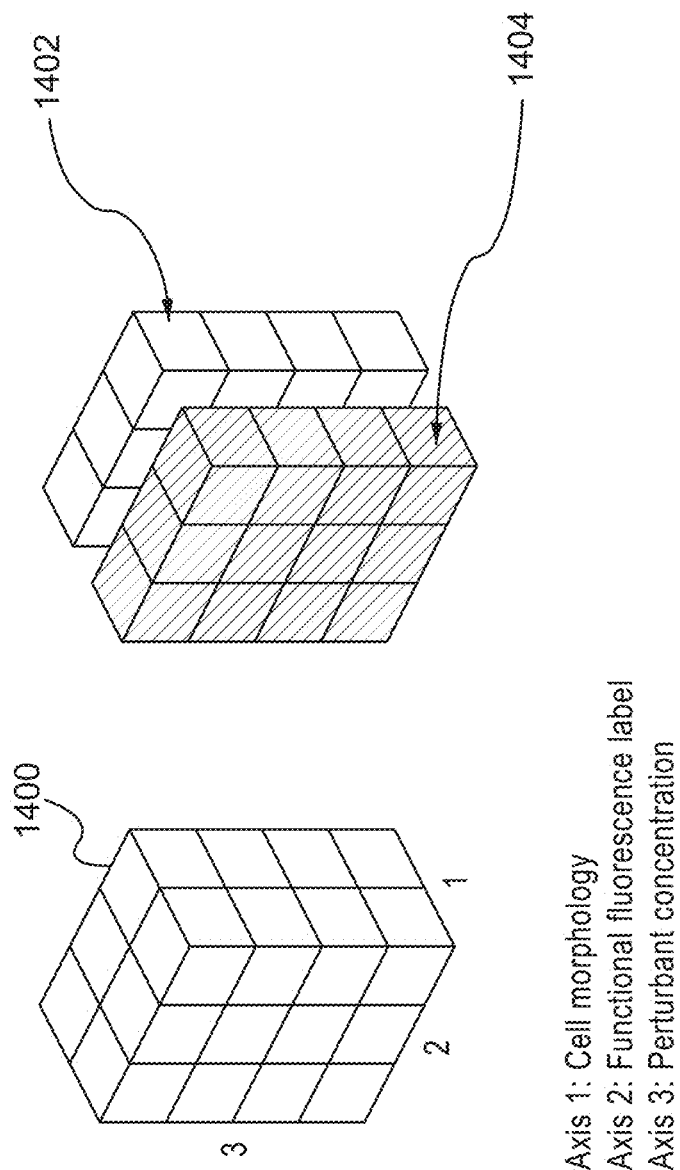

FIG. 14 shows an example of a multiway tensor representing a drug response fingerprint.

Figure 15:
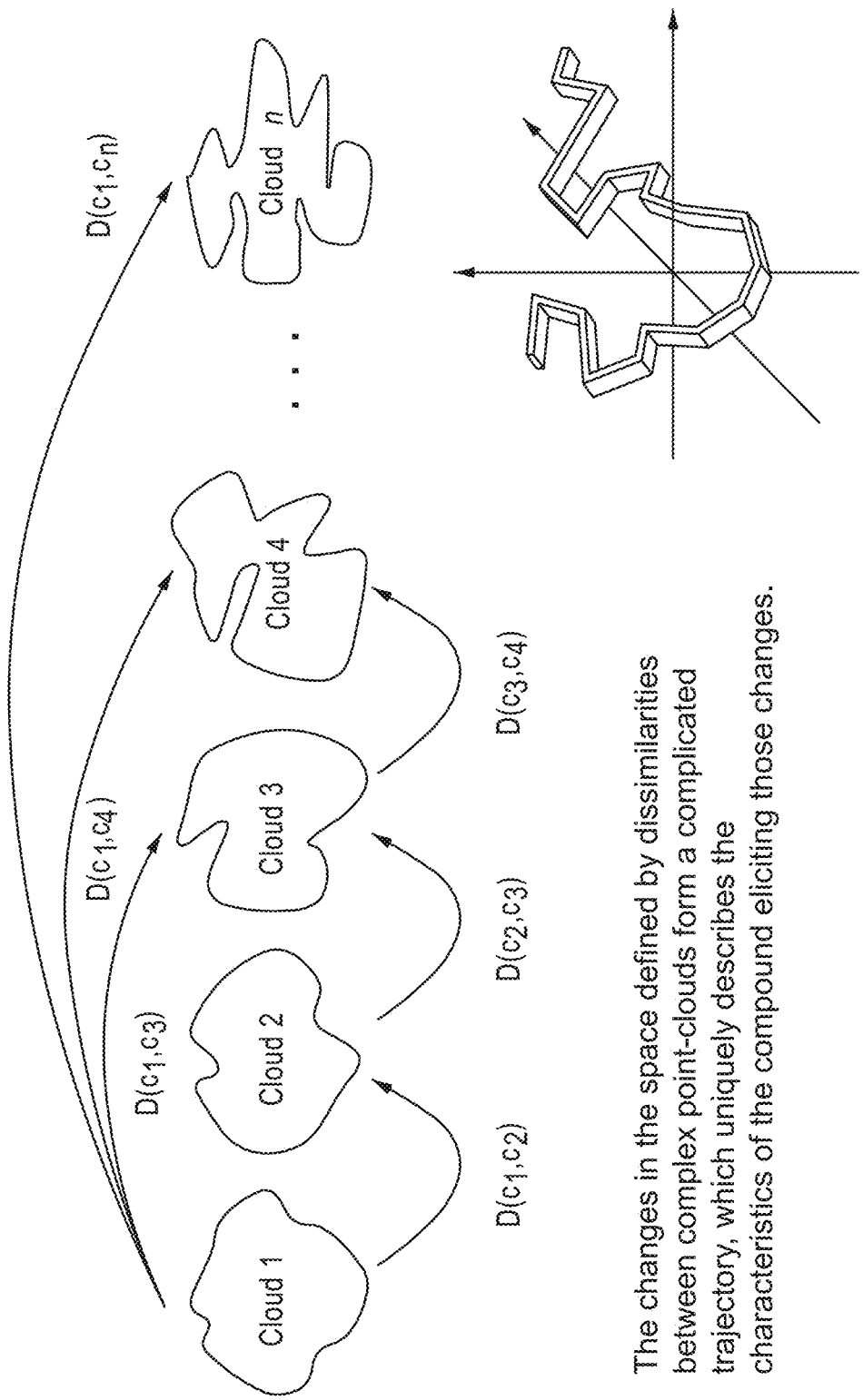

FIG. 15 shows a representative cloud evolution. The changes in the space defined by dissimilarities between complex point-clouds form a complicated trajectory, which uniquely describes the characteristics of the compound eliciting those changes.

Figure 16:
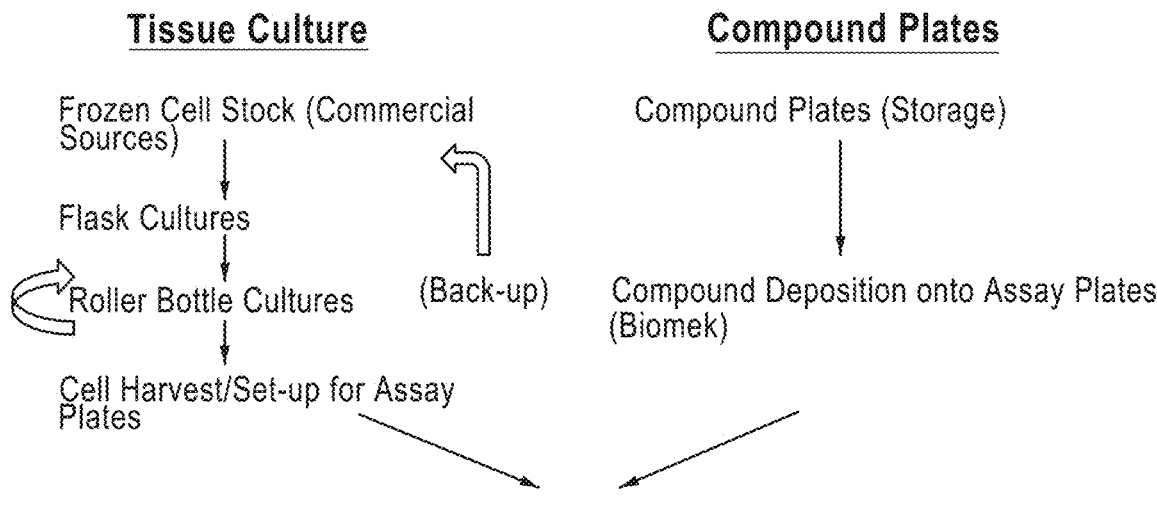

FIG. 16 is a flowchart showing general process steps for carrying out cell physiology assays.

Figure 17:
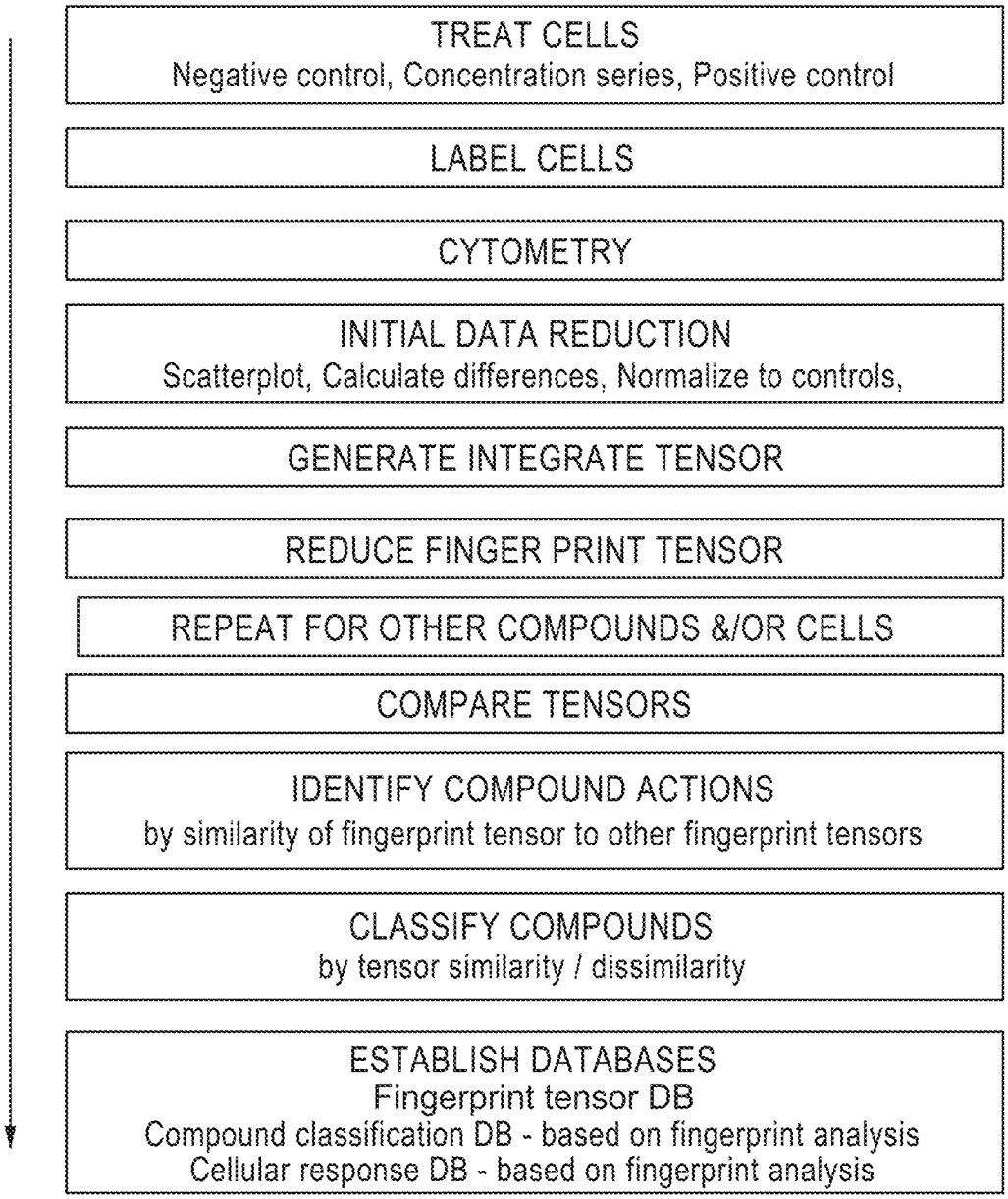

FIG. 17 is a flowchart showing steps in data analysis using tensor methods described herein.

Figure 18:
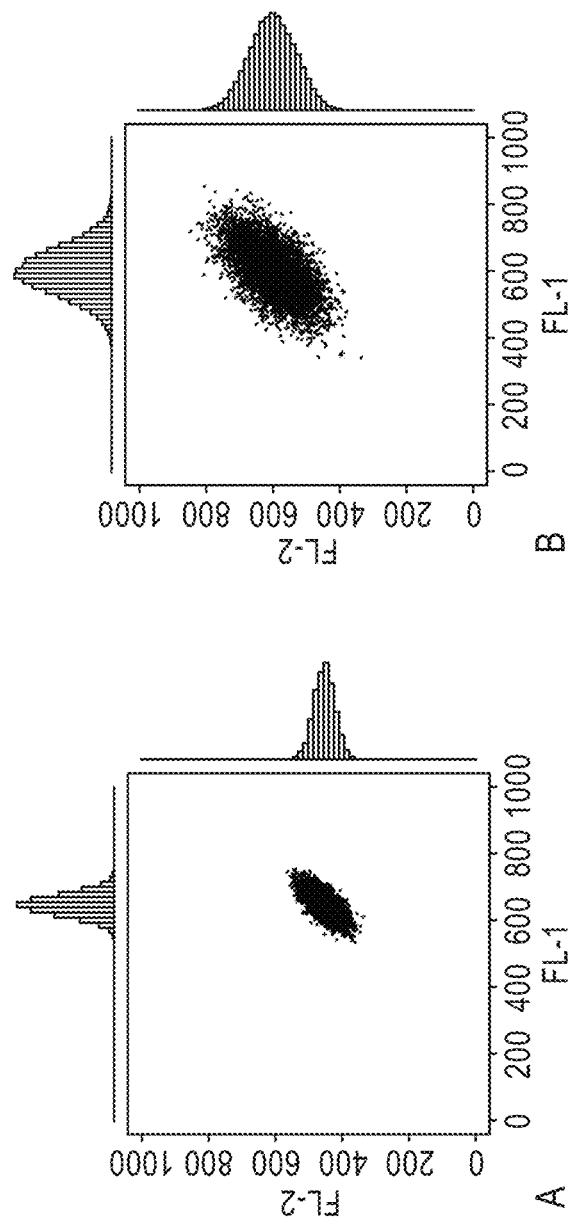

FIG. 18 shows the 2-D scatterplots of the results of a simulated flow cytometry analysis of cells that were (A) exposed and (B) not exposed to a compound. (A) and (B) represent positive and negative controls for the agent, respectively. FL1 and FL2 are fluorescent signals 1 and 2.

Figure 19:
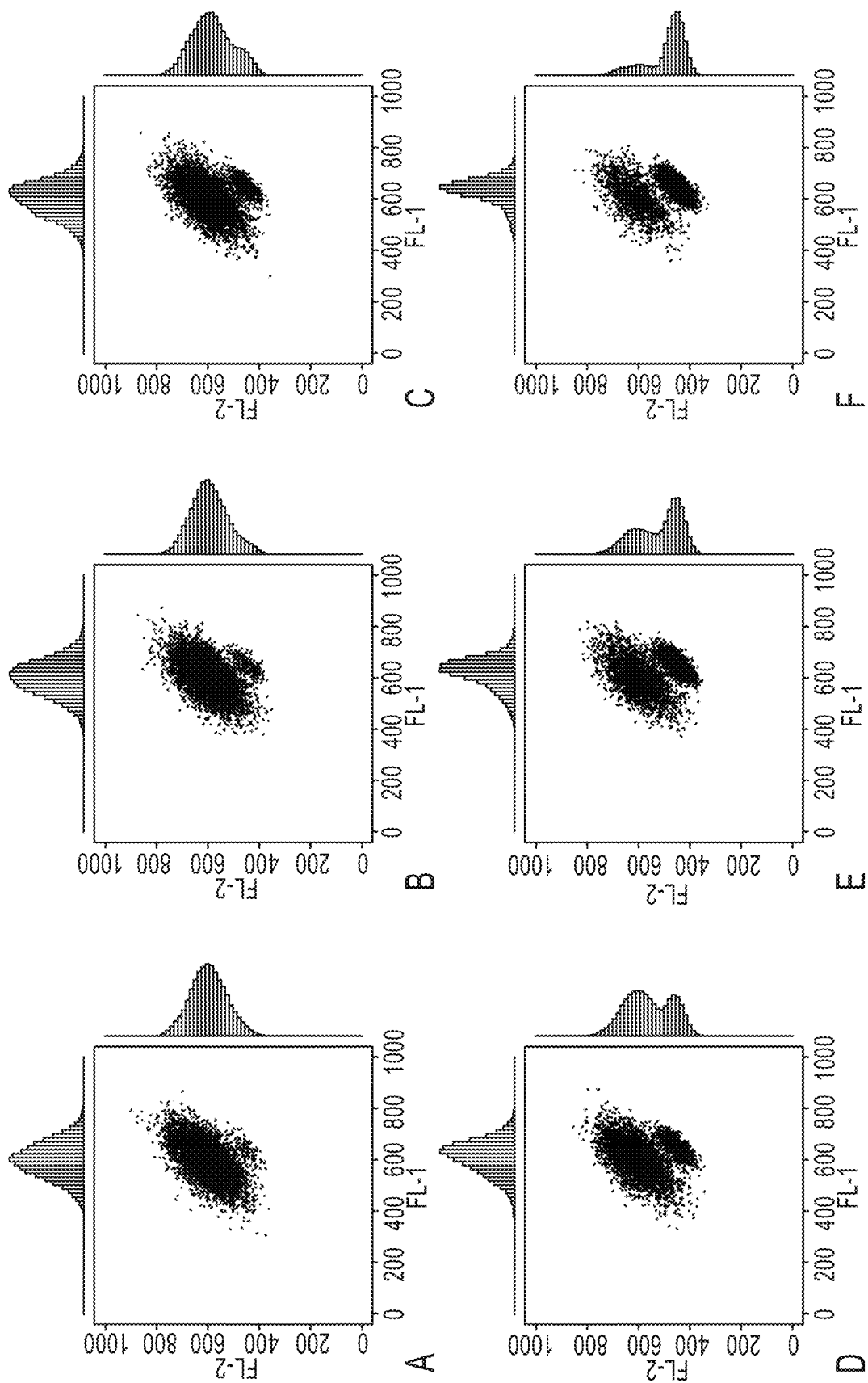
Figure 19:
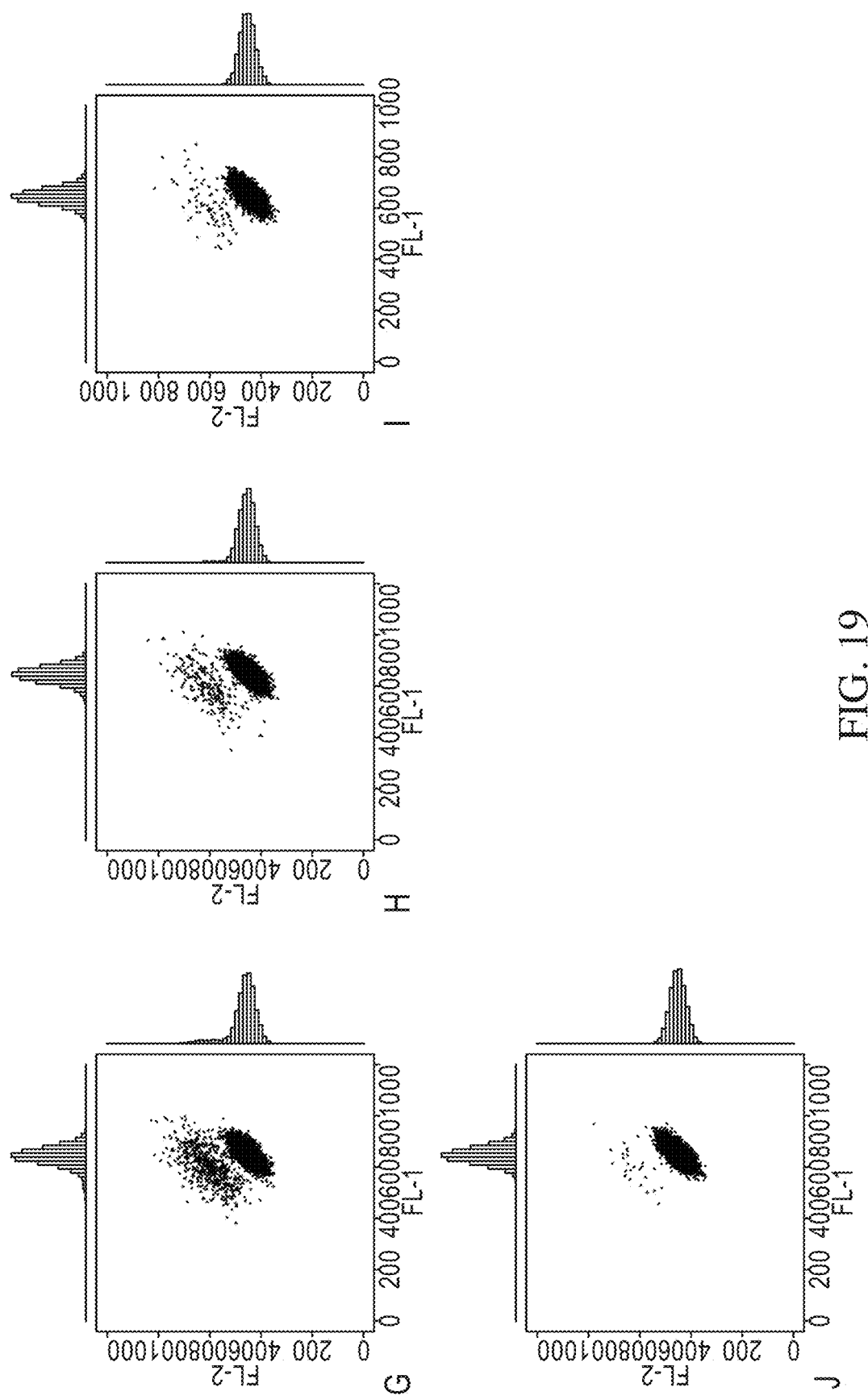

FIG. 19 shows the 2-D scatterplots of the results of a simulated flow cytometry analysis of ten samples exposed to increasing concentrations of a biological agent, as described in in Example 9. Each sample contains 5,000 cells. The concentrations were increased from A to J. The number of cells in in the positive control-like cluster decreased from 4,909 in A to 29 in J. FL1 and FL2 are fluorescent signals.

Figure 20:
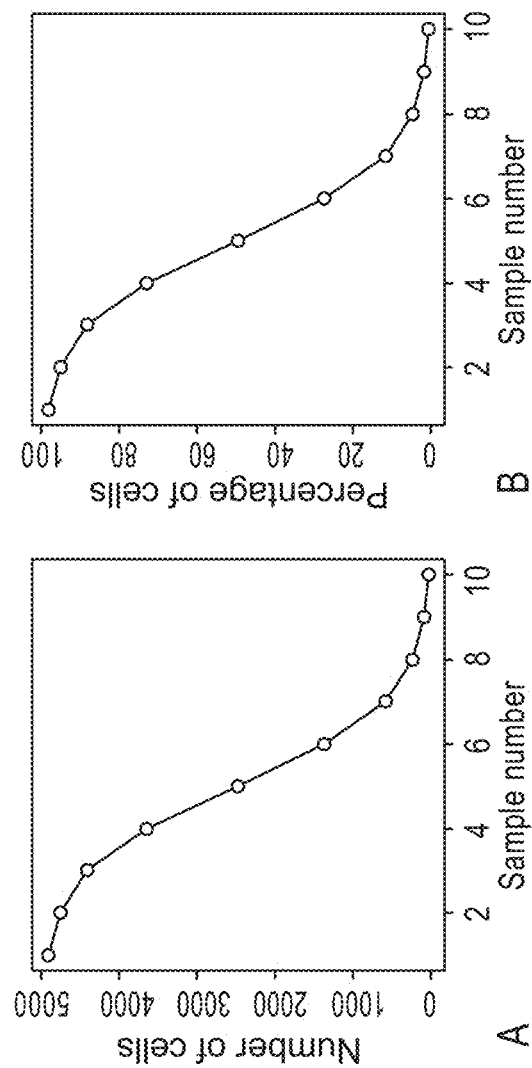

FIG. 20 provides two graphs of the response curves for the simulated flow cytometry analysis described in Example 9 and FIG. 18. (A) shows the results for each sample as a function of the number of cells in the positive-like control cluster. (B) shows the same results for each sample as a function of the percent of cells in the positive-like control cluster.

Figure 21:
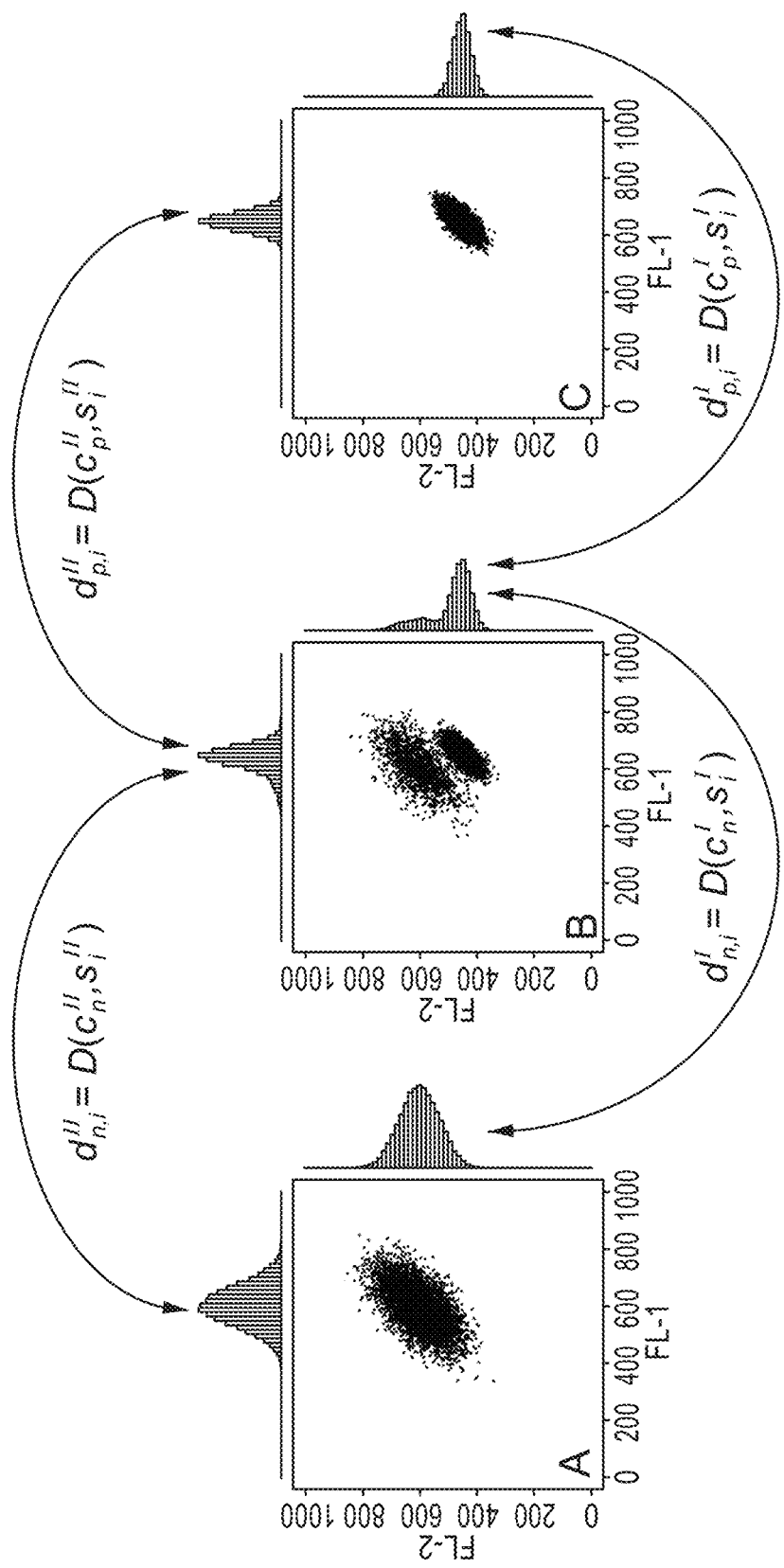

FIG. 21 shows the four distances calculated for each sample to provide a dissimilarity measure, as described in Example 9. (1) The distance between the sample and the negative control for parameter one. (2) The distance between the sample and the positive control for parameter 1. (3) The distance between the sample and the negative control for parameter two. (4) The distance between the sample and the positive control for parameter 2.

Figure 22:
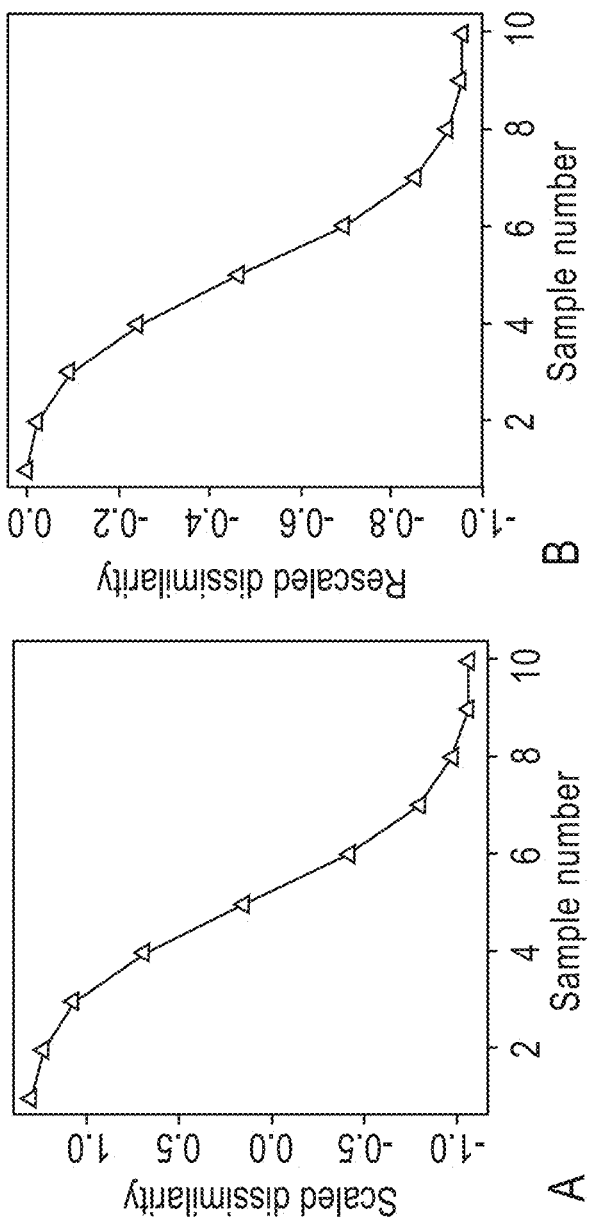

FIG. 22 shows response curves for the simulation described in Example 9 derived by polyadic tensor decomposition. The results were centered by subtracting the mean of the vector and dividing by the standard deviation. The results are expressed as a z-factor, and shown in the graph on the left. The graph on the right shows the results normalized to the difference between the negative and positive controls; i.e., in which the difference between the negative and positive controls is defined as unity (one) and the results are scaled to this difference.

Figure 23:
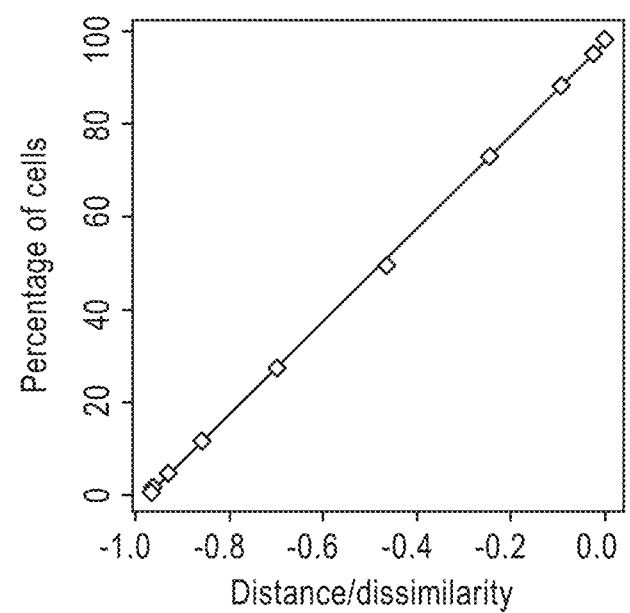

FIG. 23 is a graph for the results of the simulation described in Example 9 expressed conventionally in percentage of cells in the negative control-like cluster along the vertical axis and expressed in terms of distance/dissimilarity along the horizontal axis. Distance/dissimilarity was calculated for the same results using positive and negative controls as illustrated in FIG. 18 as described in Example 9.

Figure 24:
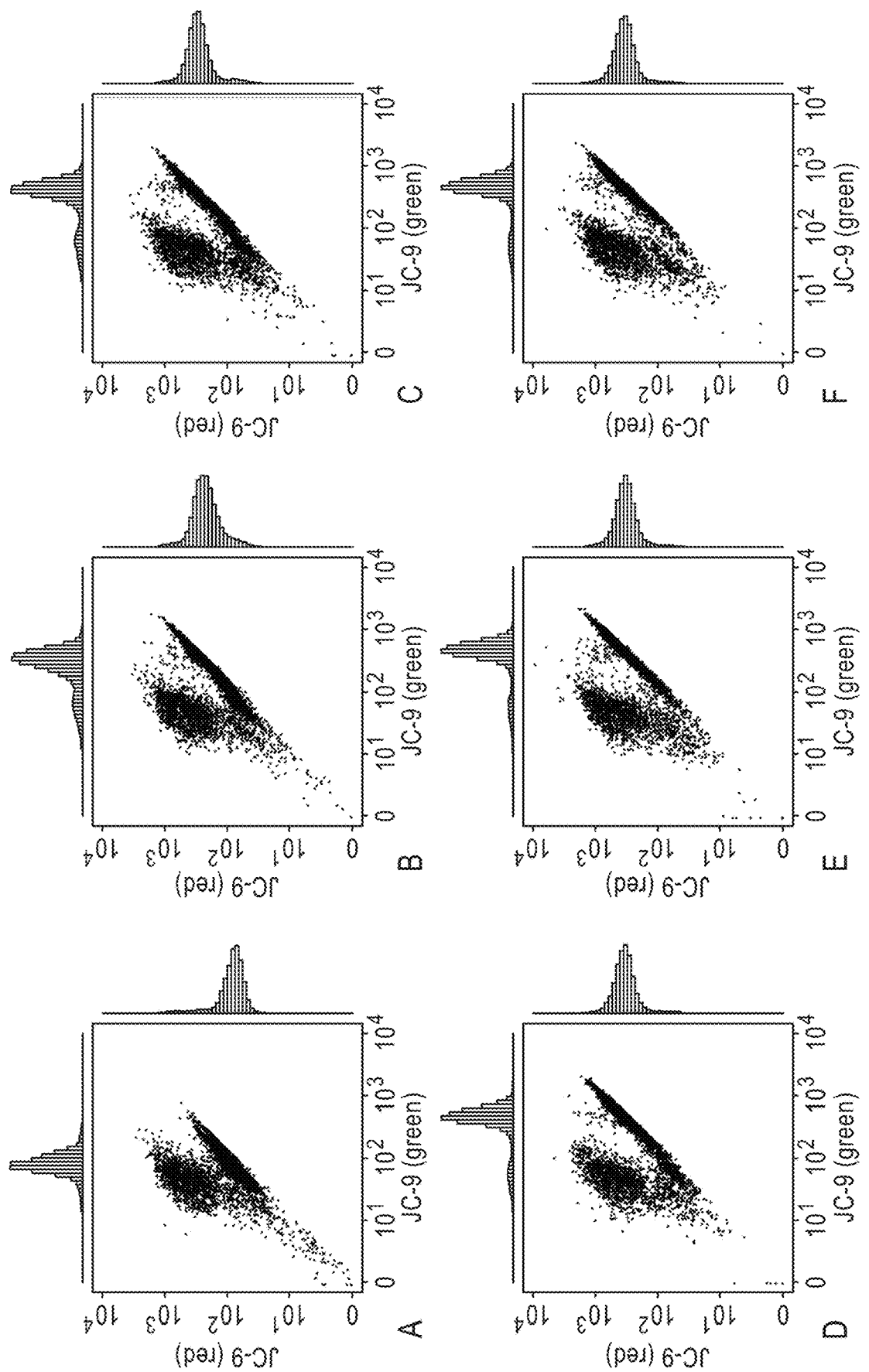
Figure 24:
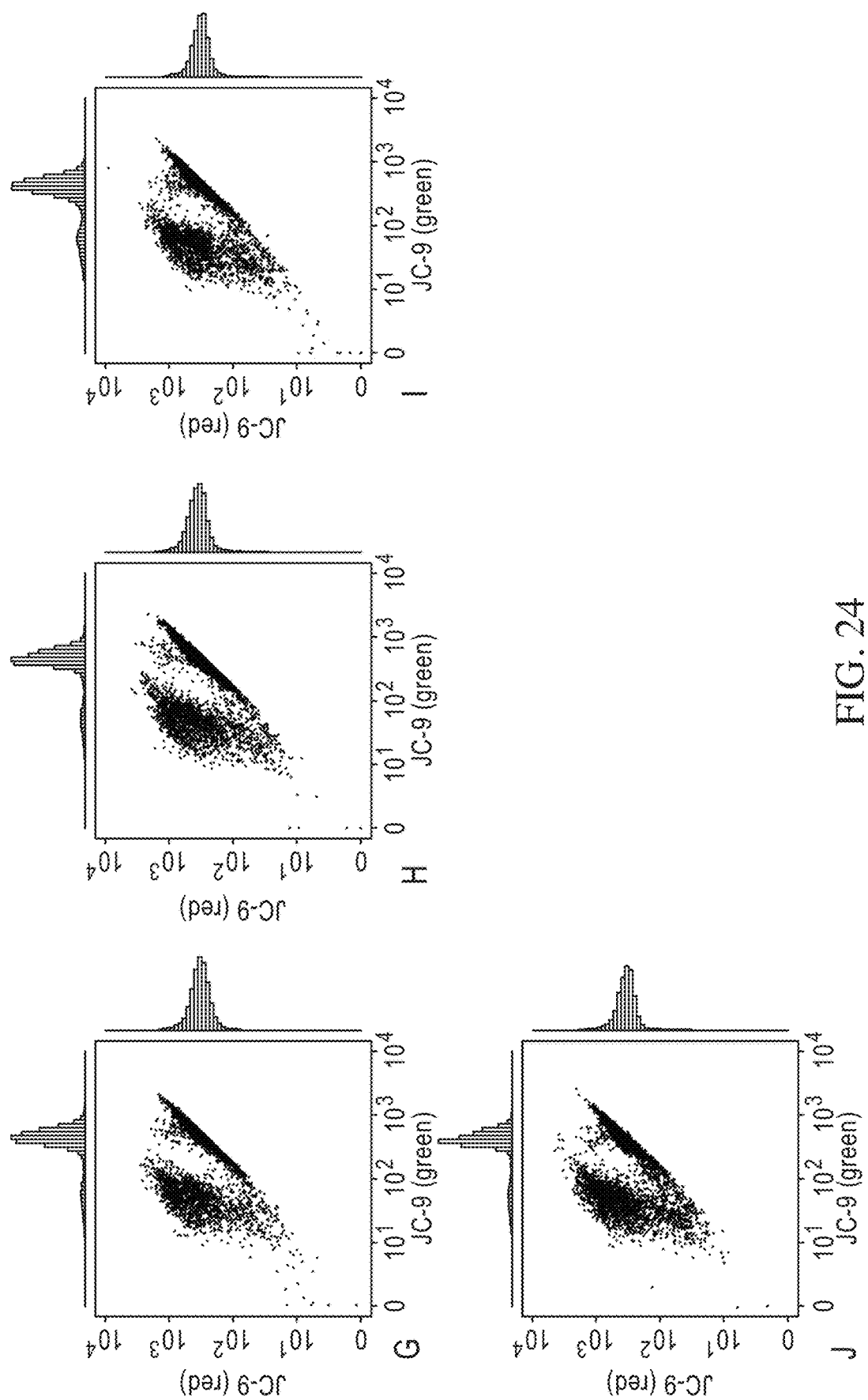

FIG. 24 shows the 2-D scatterplots of the results of flow cytometry analyses of ten samples exposed to increasing concentrations of a valinomycin as described in in Example 9B. The ratio of Red (vertical axis) and green (horizontal axis) fluorescence of JC9 were measured to determine mitochondrial membrane potential. Valinomycin concentration increased from A (lowest concentration) to J (highest concentration).

Figure 25:
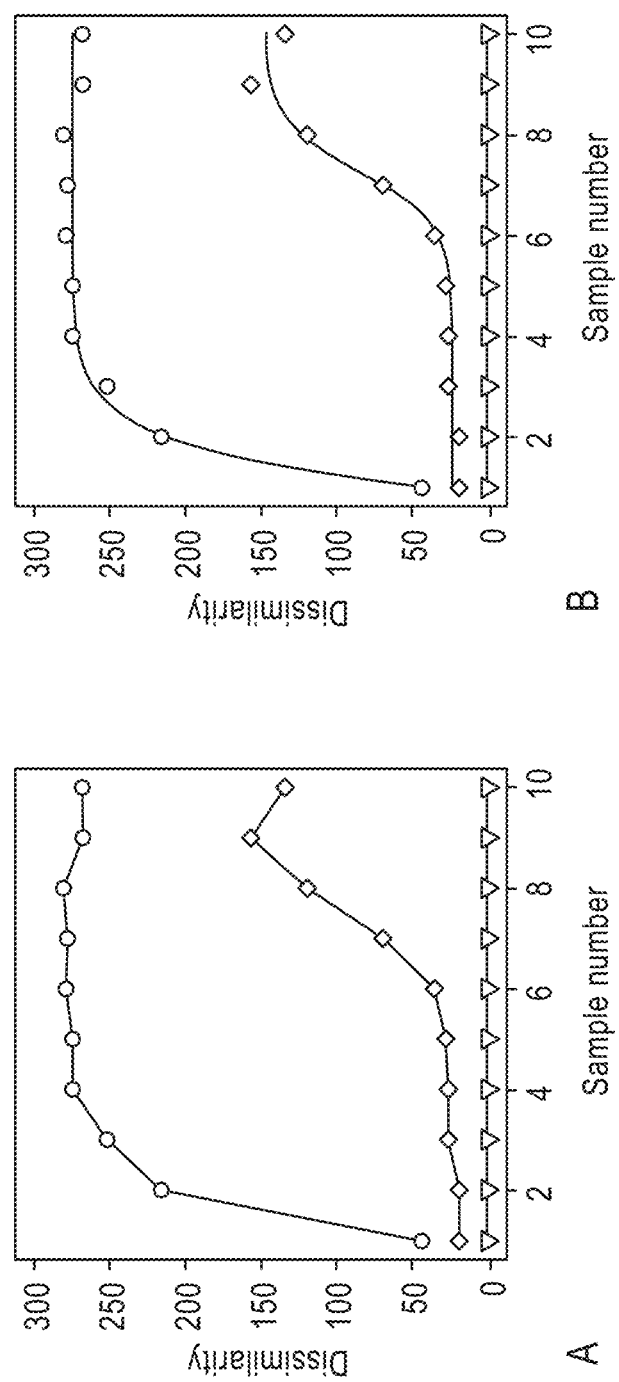

FIG. 25 shows dissimilarity response curves for the valinomycin analysis (circles) described in Example 9B and illustrated in FIG. 24, and for idarubicin (diamonds) and acetaminophen (triangles) data obtained the same way. Dissimilarities were calculated as described in the example and illustrated in FIG. 21. The graph on the left shows dissimilarity as function of sample number. The graph on the right shows dissimilarity as a function of concentration.

IV

Illustrative embodiments of the present invention provide automated, observer-independent, robust, reproducible, and generic methods to collect, compile, represent, and mine complex population based information, particularly, for instance, cytometry-based information, as for example for quantifying and comparing physiological responses of cells exposed to chemical compounds, such as drugs. Various embodiments provide methods for characterizes responses by response tensors. Illustrative embodiments provide for the use of various statistical measures of distances between distributions in one or more dimensions, and measures of dissimilarity between response vectors grouped into multi-way tensors. In various embodiments the differences in cells responses to two (or more) chemical compounds is characterized as the difference between two response tensors ("fingerprints") that represent said compounds. Embodiments provide methods for generating said fingerprints, and methods to manipulate, process, store, classify and use them.

In various embodiments herein described, for example, biological datasets are analyzed to determine matches between them, often between test datasets and control, or between test datasets and profile datasets. Comparisons may be made between two or more datasets, where a typical dataset comprises readouts from multiple cellular parameters, such as those resulting from exposure of cells to biological factors in the absence or presence of a candidate agent, where the agent may be, for instance, a genetic agent, e.g., expressed coding sequence; or a chemical agent, e.g. drug candidate; or an environmental toxin. In various embodiments, measurements are performed using cytometry, e.g., flow cytometry.

Cytometry

Methods of the various embodiments described herein are suitable for analysis of complex multi-parametric data on individual cells in cell populations, as determined by cytometry. Cytometric instruments and techniques, summarized herein (e.g., flow cytometry and imaging cytometry) allow for the simultaneous measurement of multiple intrinsic features (e.g., light scatter, cell volume, etc.) or derived features (e.g., fluorescence, absorption, etc.) of individual cells. Light scatter and fluorescence represent the most commonly utilized measurements for current cytometric applications. Fluorescence measurements can be performed either using either "intrinsic" fluorophores naturally present in cells (such as, for example, porphyrins, flavins, lipofuscins, NADPH), fluorophores genetically engineered for specific expression (e.g., GFP, RFP, etc.), or fluorescent reporters which target specific epitopes or structures in or on various cell types (e.g., fluorophore conjugated antibodies, aptamers, phage display, or peptides, or reporters that are converted from non-fluorescent to fluorescent states by specific enzymes in or on cells).

Cytometric techniques useful in embodiments herein described utilize living cells (e.g., using probes which report cell on aspects of cell "physiology", such as, for example, mitochondrial membrane potential, ROS, glutathione content, or a combination thereof). Cytometric techniques useful in some embodiments additionally employ cells that are fixed and permeabilized to allow transport of fluorophores, conjugated reporters, etc., into the cytoplasm and/or the nucleus.

General Methods for Cellular Assays Using Flow Cytometry

General methods useful for cytometry in accordance with various aspects and embodiments herein described are described below and set out in generalized flowchart in FIG. 16

Culture of Anchorage Independent Cells

Cells and methods suitable for activity assays and analysis by flow cytometry that are well known and routinely employed in the art can be employed in carrying out embodiments of inventions described herein.

Cells for assays may be obtained from commercial or other sources. Cells derived from human cancer can be used, such as those from leukemias (e.g., HL-60 cells currently used in cell physiology assay), which grow unattached to the culture vessel. Cells generally can be stored in liquid nitrogen in accordance with standard cell methods. Frozen cells are rapidly thawed in a 37° C. water bath, and cultured in stationary flasks in pre-warmed fresh tissue culture medium in a 37° C. tissue culture incubator. Tissue culture media typically is replaced daily for the first 2-4 days in culture, to dilute out the DMSO that the cells are frozen in.

Once growth is established in stationary flasks (cell number and viability are monitored using a Vi-cell™ cell counter), aliquots of cells can be removed for freezer storage (these early passage cells are only used for backup). In addition, these cells can be used to establish roller bottle cultures needed to have sufficient cell numbers for plate assays. Cells growing in flasks are placed in roller bottles at relatively high cell concentration (~$10^6$ cells per ml in 200 ml fresh tissue culture medium) and cultured in a tissue culture incubator. Initially, roller bottle cultures typically are fed by addition of fresh tissue culture medium. Once growth is established, cells are removed as needed to maintain cells at a concentration of 0.5-1.5×$10^6$ viable cells/ml. Many cell types adapt to roller bottle cultures slowly and need weeks to successfully adapt to these types of cultures. Successful roller bottle adaptation is evidenced by continuous high viability (~95%) and consistent growth rates (measured using doubling time). When successfully adapted, stocks of cells are frozen (in 50 ml sterile tubes containing sufficient cells to initiate one new roller bottle culture) in order to maintain cells used for assays at a similar low passage number (details below). Cells maintained in roller bottles are harvested for assay plates, centrifuged, and resuspended in fresh tissue culture media at appropriate cell concentration for the assay to be performed (cell number and viability measured and recorded for each harvest).

As indicated above, roller bottle adapted cells can be frozen for future use, to maintain similar low passage number cells for all plate assays. Roller bottle cell cultures can be maintained for one month before switching to a new lot of low passage frozen cells. During the month of routine use, one tube of frozen cells typically is thawed and re-established to roller bottle culture. Once successfully adapted to roller bottle culture (as above) the newest lot of cells usually is first evaluated for assay performance (see "Cross-Over" studies, below), before this lot of cells is used in plate assays. Establishing frozen cells to roller bottle culture and testing routinely takes 10 to 21 days.

Cells generally are routinely tested at multiple steps in the culture process for *mycoplasma* contamination. These include initial flask cultures, roller bottle adapted cells, and each tube of frozen cells (tested before each "Cross-Over" study). *Mycoplasma* testing can be provided by an external, certified testing company, typically using a PCR-based assay.

Compound Storage and Compound Assay Preparations

Test compounds are generally obtained as 10 mM stocks in DMSO deposited in 96-well plates. Compound plates are stored sealed at room temperature in the dark. For compound assays, stock solutions are diluted (5 to 10 step compound dilutions in DMSO) and deposited into assay plates using a liquid handling system. All dilutions and compound deposition into assay plates are performed the same day as the assay is performed. The final volume of compound deposited into each well is 2 µl, giving a final concentration of 1% DMSO after the addition of cells.

The reproducibility of assays should be assessed using test compounds. A set of 16 compounds that have well-documented impacts on specific cell physiological measurements have been used to test the reproducibility of cell physiology assays. These compounds are stored, as above, as 10 mM assay solutions in DMSO in 96-well plates. For "Cross-Over" studies, 16 compound set are used to compare the physiological responses of the newly thawed and roller bottle adapted cells with current lots of production cells.

Cell Physiology Assays

For cell physiology assays it can be convenient to use 2 sets of 384 well plates to measure the impact of compounds on ten or more cellular response parameters. For both sets of plates, compound dilutions are first deposited into wells, and then 1×$10^6$ assay cells are added to each well, as shown in step 2602. Compounds are routinely run with duplicate compound dilution sets on the same plate; at the start of a study for an individual client, duplicate plates are run for the first 16 to 32 compounds in order to measure the reproducibility of responses. After thorough mixing, plates are sealed (using an $O_2/CO_2$ permeant seal) and placed into a 37° C. tissue culture incubator for varying periods of time (typically 4 hrs), as shown in step 2604. Plates are then centrifuged in step 2606, half the supernatant fluid is removed, and replaced by the same volume of the appropriate dye mix (for plate A, the dye mix may include Monobromobimane, Calcein AM, MitoSox™, and Sytox Red™; for plate B, the dye mix may include Vybrant Violet™ (live cell cycle), JC-9 (mitochondrial membrane potential), and Sytox Red™), followed by mixing, as shown in step 2608. Plates are returned to the tissue culture incubator for about 15 (plate A) or 30 (plate B) minutes in step 2610, followed by a mix, and immediately run on the flow cytometer in step 2612.

The data from positive and negative control wells on each row are used to calculate the responses as described in greater detail herein. The positive control compounds used for plate A and B are different, and are designed to provide a unique "signature" ("fingerprint") in the cell responses measured in plate A or B, using the disclosed embodiments.

High Throughput Flow Cytometry

In a variety of assays the flow cytometer is set up using a standard procedure on each day that plates are assayed. Setup includes flow instrument QA/QC using fluorescent beads, which are used to set each detector (PMT) to a standardized target. Each well of a 384-well plate is then sequentially sampled using a 6-second sip time, followed by a 1-second air bubble between samples. The sample stream flows through the flow cytometer in a continuous fashion, sampling a complete plate in 20 to 30 minutes (plates A and B, respectively).

The flow cytometry data file (for one plate) is subsequently processed by the disclosed embodiments to identify individual well data (using some interaction and human intervention), and is then stored on a server as the list mode data (LMD) for each well from a single plate.

QA/QC Analysis of Each Plate

Both plates (A and B) contain negative controls (untreated samples), and positive controls (sample treated with a mixture of 50 µM FCCP plus 50 µM Myxathiazol for plate A, or 25 µM FCCP for plate B). The dissimilarity between positive controls and negative controls does not define in this assay the possible range of responses. However, it defines a unit of response. During the time of analysis of an entire plate, the dissimilarity between positive and negative controls may change owing to deteriorating physiological conditions in the plate (change in temperature, $O_2$, etc). This is why a certain minimum level of dissimilarity for every pair of controls is expected. For each positive and negative control within a single row, the disclosed embodiments determine the QF distance between the positive and negative populations for each dye response individually. The disclosed embodiments then plot the change in QF distance from the beginning (row A) to the end of the plate (row P).

Experiments described herein generally have been carried out in accordance with the foregoing procedures.

Cytometer Instrumentation

Current flow cytometry instruments are equipped with multiple lasers and multiple separate fluorescence detectors that can simultaneously quantitate many fluorescence signals plus intrinsic optical features originating from individual cells. Thus, cytometric techniques and instruments such as those illustratively described below allow measurement of thousands to millions of cells in a sample. The resultant extremely large data sets present a significant challenge to the presently-employed cytometry data processing and visualization methods. These challenges are handled effectively by methods described herein.

Modern cytometers are typically designed for simultaneously detecting several different signals from a sample. A variety of cytometers are available commercially that can be used in accordance with the methods described herein. A typical instrument includes a flow cell, one or more lasers that illuminate the flow cells through a focusing lens, a detector or light passing through the flow cell, a detector for forward scattered light, several dichroic mirror-detector arrangements to measure light of specific wavelengths, typically to detect fluorescence. A wide variety of other instrumentation often is incorporated in commercial instruments.

In typical operations, the laser (or lasers) illuminates the flow cell and the cells (or other sample) flowing through it. The volume illuminated by the laser is referred to as the interrogation point. Flow cells are made of glass, quartz, and plastic, as well as other materials. Although lasers are the most common source of light in cytometers, other light sources can also be used. Almost all cytometers can detect and measure a variety of parameters of forward-scattered and back-scattered light and several wavelengths of fluorescence emission as well. Detectors in these instruments are quite sensitive and easily quantify light scattering and fluorescence from individual cells very short periods of time. Signals form the detectors typically are digitized and analyzed by computational methods to determine a wide variety of sample properties. There are many texts available on flow cytometry methods that can be used in accordance with various aspects and embodiments of the inventions herein described. One useful reference in this regard is Practical Flow Cytometry, 4th Edition, Howard M. Shapiro, Wiley, New York (2003) ISBN: 978-0-471-41125-3, which is herein incorporated by reference particularly in parts pertinent to cytometry and cell analysis as may be used in accordance with the methods herein described.

Spectral Unmixing of Flow Cytometric Signals

Since the signals emitted by the functional fluorescence labels are measured by a series of detectors in a cytometry system (flow- or image-based), the detection systems are prone to spectral cross-talk. As a result, the intensities of individual fluorochromes cannot be measured directly to the exclusion of other fluorochromes. In order to minimize or eliminate noise due to spectral cross-talk, all of the collected signals can be modeled or processed as linear mixtures. The signal mixture for each measured cell is decomposed into approximations of individual signal intensities by finding a minimal deviance between the measured results and approximated compositions which are formed by multiplying the estimator of the unmixed signal with the mixing matrix. The mixing matrix (also called "spillover matrix") describes the n-band approximation of fluorescence spectra of the individual labels (where n is the number of detectors employed in the system). An application of a minimization algorithm allows to find the best estimation of the signal composition. This estimation provides information about the abundances of different labels. In the simplest case, if the measurement error is assumed to be Gaussian, the unmixing process may be performed using ordinary least-squares (OLS) minimization.

Variance Stabilization

Variance stabilization (VS) is a process designed to simplify exploratory data analysis or to allow use of data-analysis techniques that make assumptions about data homoskedasticity for more complex, often noisy, heteroskedastic data sets (i.e., random variables in the sequence have different finite variance). VS has been routinely widely applied to various biological measurement systems based on fluorescence. It is an important tool for analysis of microarrays.

In the context of flow cytometry and in microarray analysis, log transformation has traditionally been used. However, modern approaches, for example, in the context of microarray analysis are known. For example, see Rocke et al. (Approximate variance-stabilizing transformations for gene-expression microarray data." *Bioinformatics*, 19, 966-972, 2003) and Huber et al. ("Variance stabilization applied to microarray data calibration and to the quantification of differential expression." *Bioinformatics*, 18, S96-S104, 2002). Huber describes the use of a hyperbolic arcsine function in variance stabilization. In the context of flow cytometric data analysis, Moore et al. ("Automatic clustering of flow cytometry data with density-based merging," *Adv Bioinformatics*, 2009) uses logical transformation. Bagwell ("Hyperlog-a flexible log-like transform for negative, zero, and positive valued data." *Cytometry A*. 64(1): 34-42, 2005) describes the use of hyperlog transformation in the analysis of output from flow cytometers.

In an embodiment of the present invention, in contrast, hyperbolic arsine technique (generalized logarithm) with an empirically found parameter is used in variance stabilization.

$$g\ \log(x) = a\ \sinh(x) = \log(x+\sqrt{x^2+1})$$

$$g\ \log(x,a,b,c) = a\ \sinh(ax+b)+c$$

Comparisons

Certain embodiments described herein provide methods involving a comparing step, wherein the distribution of the unmixed signal intensities is compared to the distribution of the unmixed signals originating from controls or other test data. Depending on the comparison method applied, the distributions may be first normalized by dividing every distribution by its integral.

The comparing step may involve compilation of response tensors containing information about dissimilarities between cellular populations such as before and after treatment. The dissimilarities are computed as distances between signal distributions of the treated population of cells, untreated populations ("negative" or "no effect" controls), and populations treated with a mixture of perturbants designed to maximize the observable physiological response ("positive" or "maximum effect" controls).

In order to standardize the result and render it unaffected by experimental variability, the measured dissimilarity can be expressed in units equal to mean dissimilarity between positive and negative controls.

Various measures of dissimilarity or distance can be applied, including (but not limited to): Wasserstein metric, quadratic-form distance (QFD), quadratic chi-distance, Kolmogorov metric, (symmetrized) Kullback-Leibler divergence, etc. In the preferred implementation, the methods and algorithms of the instant invention use Wasserstein metric or quadratic chi-distance.

In illustrative methods below, the abundance distributions are typically compared in one dimension. However, some labels are encoded by two related signals (for instance, JC-1, the mitochondrial membrane potential label that emits fluorescence in two separate channels). In this case, a 2-D dissimilarity measure between distributions is computed. Finally, it may be preferable to compute 2-D or 3-D dissimilarity measures by utilizing multidimensional distributions based on morphology-related measurements (obtained via light scatter) and an abundance (computed from the fluorescence signal). A variety of distances or dissimilarity measures, assuming that they are easily generalizable to multiple dimensions, may be used. For instance, routine methods based on the Wasserstein metric or the QFD may be used in this context, but not the Kolmogorov metric.

A representative equation for comparison of populations is provided below (see, Pele et al. "The Quadratic-Chi Histogram Distance Family." *Computer Vision—ECCV 2010, Lecture Notes in Computer Science. Springer Berlin Heidelberg*, pp. 749-762; Daniilidis, K., Maragos, P., Paragios, N. (Eds.)):

$$QFD(x, y) = \sqrt{\max[(dAd^T), 0]}$$

$$d = \frac{(x-y)}{z}$$

$$z = ((x+y)A)^m$$

$$A[i, j] = 1\sqrt{\frac{(i-j)^2}{d_{max}}}$$

wherein x and y are distributions of interest, and A is a positive-semidefinite dissimilarity matrix.

Analysis of Cytometry Data Using Tensors

Cytometric multi-parametric data can be expressed as tensors and the comparisons between controls and tested samples can be described by compound fingerprint tensors. A tensor is a multidimensional array and can be considered as a generalization of a matrix. A first-order (or one-way) tensor is a vector; a second-order (two-way) tensor is a matrix. Tensors of order three (three-way) or higher are called higher-order tensors.

Biological measurements performed in a single-cell system individually for every cell in a population form a distribution. A distance between a distribution of measurements performed on cells exposed to a presence of a compound, and a distribution of measurements performed on cells not exposed to the compound can be expressed by a single number (scalar value). The cells may be exposed to a number of different drug concentrations, and a biological measurement can be performed for each of these exposure levels. Such an experiment produces a series of values that can be expressed as a vector (e.g., a one-way tensor). If multiple biological parameters are measured, the results can be arranged in a two-way tensor (or a matrix), in which every column contains a different measured parameter and every row describes a different concentration of the compound.

This arrangement of data can be expanded further. If we attempt to measure the distances between the distributions of measurements obtained from treated cells and a distribution of measurements collected from population of cells exposed to another compound, we can group the results into another matrix. For instance, it may be beneficial to measure dissimilarity between cells treated with one compound and another group of cells treated with a different and well characterized compound that creates an easy to observe effect serving as a positive control.

The two matrices (two-way tensors) put together produce a three-way tensor. The dimensionality of this three-way tensor is $I_1 \times I_2 \times I_3$, where $I_1$ is the number of concentrations, $I_2$ is the number of measured biological parameters, and $I_3$ is the number of measured dissimilarities/distances (typically two: positive control distance measurement, and a negative control distance measurement). Therefore, for a tensor A representing the biological measurement, the element (i,j,k), denoted by $a_{i,j,k}$ describes a distance between measurements of parameter j obtained from a cell population exposed to a compound at concentration i, and a control cell population k.

A column fiber of tensor A, denoted as $a_{:jk}$ contains a whole series of distances between measurements of parameter j performed for a series of tested samples and a control k. If 10 concentrations of a compound are tested, the column fiber $a_{:jk}$ will be a 10-element vector. A frontal slice of the tensor A denoted $A_{::k}$, forms a matrix that describes the distances measured to k-control. A lateral slice $\lambda_{:j:}$ is a matrix showing measurements of distances for parameter j.

The tensor A can be further expanded to account for multiple environments, cell cultures or phases of cell cycle. Therefore, multiple repeats of the measurements, multiple phases of cell cycle in which the measurements are performed, and so forth, can be stored in a compound fingerprint tensor. In fact, any multidimensional screening experiment can be represented as a $p^{th}$-order tensor $A \in \mathbb{R}^{I_1 \times I_2 \times \cdots \times I_p}$ For instance, one may group the data from multiple experiments in a four-way tensor with a dimensionality $I_1 \times I_2 \times I_3 \times I_4$, where $I_4$ is the number of unique measured compounds. In this setting, a slice $\lambda_{:jkl}$ contains dissimilarities between tested samples containing compound l and a control k, computed for parameter j. If four repeats of a compound l were measured, the resultant $\lambda_{:jkl}$ slice is a matrix of ten rows (concentrations), and four columns (repeats).

The tensor representation of the compound measurements can be used to define a number of compound-related metrics and operators, such as a compound similarity/dissimilarity, compound fingerprint, compressed compound fingerprint, compound normalization, etc. The arrangement of the phenotypic screening data in a tensor format enables the formulation of unique insights regarding compound characteristics through analysis of compound response similarities. This is impossible when the information regarding the compounds is represented simply as data vectors. Specifically, the techniques described below would be impossible to implement if compounds were described only using scalar values (such as traditionally utilized $IC_{50}$ value).

The foregoing analysis can be stated in general terms in the form of the following equation and operations herein referred to as General Tensor Analysis of Population Data General Method and Equations—I In the first step a pair of distances between the positive controls ($C_p$) and the negative control (Ca) is computed for every marginal histogram V. These distances are kept as references for further use and rescaling:

$$f_{np}^{(\psi)} = D(C_n^{(\psi)}, C_p^{(\psi)}) \text{ where } \psi \in \{1, \ldots, p\}$$

The distance function D can be a quadratic form distance, a Wasserstein distance, a quadratic-$\lambda^2$ distance or any other distance operating on vectors representing histograms.

$$f_j = D(C_\kappa^{(\psi)}, C_i^{(\psi)})$$

Following this operation a series of distances for the biological samples are calculated in an analogous fashion. Distances are computed for every pair made of a control K and a biological sample in the series of concentration $(S_1, S_2, \ldots, S_i)$, where i denotes the concentration of a tested compound.

$$d_{\kappa,i}^{(\psi)} = D(C_\kappa^{(\psi)}, S_i^{(\psi)})$$

The resultant values form a multidimensional array or $p^{th}$-order tensor $A \in \mathbb{R}^{I_1 \times I_2 \times \cdots \times I_p}$. The size and the dimensionality of the tensor depend on the number of controls, the number of utilized one-dimensional histograms, and the number of biological conditions at which the measurements were conducted.

A column fiber of tensor A, denoted as $a_{[\kappa,\psi]}$ is a vector which contains a series of distances between measurements of a biological parameter summarized by marginal histogram V performed for a series of tested samples and a control K.

$$a_{[\kappa,\psi]} = \begin{bmatrix} d_{\kappa,1}^{(\psi)} = D(C_\kappa^{(\psi)}, S_1^{(\psi)}) \\ d_{\kappa,1}^{(\psi)} = D(C_\kappa^{(\psi)}, S_2^{(\psi)}) \\ \vdots \\ d_{\kappa,1}^{(\psi)} = D(C_\kappa^{(\psi)}, S_n^{(\psi)}) \end{bmatrix}$$

A frontal slice of the tensor A denoted $a_{[\kappa,\psi]}$, forms a matrix which describes the distances for biological parameter V, where the measurement involves all controls.

$$a_{[\psi]} = \begin{bmatrix} \begin{bmatrix} d_{\kappa_1,1}^{(\psi)} = D(C_{\kappa_1}^{(\psi)}, S_1^{(\psi)}) \\ d_{\kappa_1,1}^{(\psi)} = D(C_{\kappa_1}^{(\psi)}, S_2^{(\psi)}) \\ \vdots \\ d_{\kappa_1,1}^{(\psi)} = D(C_{\kappa_1}^{(\psi)}, S_n^{(\psi)}) \end{bmatrix}, \begin{bmatrix} d_{\kappa_2,1}^{(\psi)} = D(C_{\kappa_2}^{(\psi)}, S_1^{(\psi)}) \\ d_{\kappa_2,1}^{(\psi)} = D(C_{\kappa_2}^{(\psi)}, S_2^{(\psi)}) \\ \vdots \\ d_{\kappa_2,1}^{(\psi)} = D(C_{\kappa_1}^{(\psi)}, S_n^{(\psi)}) \end{bmatrix}, \ldots, \begin{bmatrix} d_{\kappa_m,1}^{(\psi)} = D(C_{\kappa_m}^{(\psi)}, S_1^{(\psi)}) \\ d_{\kappa_m,1}^{(\psi)} = D(C_{\kappa_m}^{(\psi)}, S_2^{(\psi)}) \\ \vdots \\ d_{\kappa_m,1}^{(\psi)} = D(C_{\kappa_m}^{(\psi)}, S_n^{(\psi)}) \end{bmatrix} \end{bmatrix}$$

A lateral slice $\lambda_{[\psi]}$ is a matrix showing measurements of distances for multiple biological parameters, where the measurement was performed using just a single control K.

$$A_{[\kappa]} = \begin{bmatrix} \begin{bmatrix} d_{\kappa,1}^{(\psi_1)} = D(C_\kappa^{(\psi_1)}, S_1^{(\psi_1)}), d_{\kappa,1}^{(\psi_2)} = D(C_\kappa^{(\psi_2)}, S_1^{(\psi_2)}), \cdots, d_{\kappa,1}^{(\psi_p)} = D(C_{\kappa_1}^{(\psi_p)}, S_1^{(\psi_p)}) \end{bmatrix} \\ \begin{bmatrix} d_{\kappa,1}^{(\psi_1)} = D(C_\kappa^{(\psi_1)}, S_2^{(\psi_1)}), d_{\kappa,1}^{(\psi_2)} = D(C_\kappa^{(\psi_2)}, S_2^{(\psi_2)}), \cdots, d_{\kappa,1}^{(\psi_p)} = D(C_{\kappa_1}^{(\psi_p)}, S_2^{(\psi_p)}) \end{bmatrix} \\ \vdots \\ \begin{bmatrix} d_{\kappa,1}^{(\psi_1)} = D(C_\kappa^{(\psi_1)}, S_n^{(\psi_1)}), d_{\kappa,1}^{(\psi_2)} = D(C_\kappa^{(\psi_2)}, S_n^{(\psi_2)}), \cdots, d_{\kappa,n}^{(\psi_p)} = D(C_{\kappa_1}^{(\psi_p)}, S_n^{(\psi_p)}) \end{bmatrix} \end{bmatrix}$$

Therefore, the tensor A can be expressed as:

$$A = \begin{bmatrix} a_{[\kappa_1,\psi_1]} & \cdots & a_{[\kappa_1,\psi_p]} \\ \vdots & \ddots & \vdots \\ a_{[\kappa_m,\psi_1]} & \cdots & a_{[\kappa_m,\psi_p]} \end{bmatrix}$$

The biological measurements may be further normalized by dividing every $d_{\kappa,i}^{(\psi)}$ by the corresponding $f_{np}^{(\psi)}$ resulting in a normalized tensor of distances:

$$\tilde{A} = \begin{bmatrix} \tilde{a}_{[\kappa_1,\psi_1]} & \cdots & \tilde{a}_{[\kappa_1,\psi_p]} \\ \vdots & \ddots & \vdots \\ \tilde{a}_{[\kappa_m,\psi_1]} & \cdots & \tilde{a}_{[\kappa_m,\psi_p]} \end{bmatrix}$$

The same analysis can be carried out for a variety of conditions, resulting in a series of normalized tensors of distances.

Compression

A tensor A obtained from a series of measurements forms a unique compound fingerprint, as it contains all the phenotypic characteristics of a tested compound. This tensor A can be "compressed" using a low-rank tensor approximation techniques such as polyadic tensor decomposition or other methods. See Kolda and Bader, "Tensor decompositions and applications," *SIAM Rev.* 51, 455, 2009, which is incorporated by reference in parts pertinent thereto.

Tensor decomposition factorizes a tensor into a sum of component rank-one tensors. A tensor $A \in \mathbb{R}^{I_1 \times I_2 \times \cdots \times I_p}$ by definition is rank one if it can be expressed as the outer product of p vectors:

$$A = a^{(1)} \circ a^{(2)} \circ \ldots \circ a^{(p)}$$

The goal of canonical polyadic (CP) decomposition is finding an approximation of tensor A denoted Â, which satisfies the following criteria:

$$\min_{\hat{A}} \|A - \hat{A}\|, \text{ where } \hat{A} = [[\lambda, A^{(1)}, A^{(2)}, \ldots, A^{(n)}]] = \sum_{r=1}^{R} \lambda_r a_r^{(1)} \circ \cdots \circ a_r^{(p)}$$

where $\|.\|$ denotes norm of a tensor.

Tensors can be decomposed using other techniques as well. For instance, Tucker decomposition decomposes a tensor into a core tensor multiplied by a matrix along each mode:

$$\hat{A} = [[G; M^{(1)}, M^{(2)}, \ldots, M^{(p)}]] = \sum_{r_1=1}^{R_1} \sum_{r_2=1}^{R_2} \cdots \sum_{r_p=1}^{R_p} g_{r_1 r_2 \cdots r_p} a_{r_1}^{(1)} \circ a_{r_2}^{(2)} \circ \cdots \circ a_{r_N}^{(p)}$$

The various methods for tensor decomposition allow us to approximate a complicated multidimensional compound fingerprint with a "compressed," abbreviated version. This goal can be accomplished by removing the part of a decomposition, which does not contribute significantly to tensor rebuilding accuracy.

The example below illustrates the point. Assume that A is a three-way tensor containing a compound's information. The front slices of tensor A, denoted $A_{:,:,1}$, and $A_{:,:,2}$, are:

|      | [,1]  | [,2]  | [,3]   |      | [,1]  | [,2]  | [,3]   |
|------|-------|-------|--------|------|-------|-------|--------|
| [1,] | 9.02  | 17.63 | 27.07  | [1,] | 9.90  | 20.25 | 29.92  |
| [2,] | 18.23 | 36.13 | 53.95  | [2,] | 19.92 | 40.12 | 59.78  |
| [3,] | 27.16 | 53.81 | 81.07  | [3,] | 29.73 | 59.67 | 90.24  |
| [4,] | 36.02 | 72.05 | 108.15 | [4,] | 39.81 | 80.16 | 119.79 |
| [5,] | 44.85 | 89.85 | 134.89 | [5,] | 49.58 | 99.94 | 149.88 |
| Slice $A_{:,:,1}$ | | | | Slice $A_{:,:,2}$ | | | |

After performing CP decomposition we obtain the following vectors:

$a_1^{(1)} = [-0.1348, -0.2698, -0.4048, -0.5398, -0.6737]$ $a_2^{(1)} = [0.2366, 0.4133, -0.7798, 0.4011, -0.0657]$ $a_1^{(2)} = [-0.2663, -0.5347, -0.802]$ $a_2^{(2)} = [0.1966, -0.8447, 0.4979]$ $a_1^{(3)} = [0.6691, 0.7431]$ $a_2^{(3)} = [-0.2009, -0.9796]$ $\lambda_1 = 372.9803, \lambda_2 = 0.5591139$ The original tensor may be rebuilt from this result following the CP model:

$$\hat{A} = \lambda_1 a_1^{(1)} \circ a_1^{(2)} \circ a_1^{(3)} + \lambda_2 a_2^{(1)} \circ a_2^{(2)} \circ a_2^{(3)}$$

After rebuilding the approximated tensor A contains the following values:

|      | [,1]      | [,2]     | [,3]      |      | [,1]      | [,2]     | [,3]      |
|------|-----------|----------|-----------|------|-----------|----------|-----------|
| [1,] | 8.954503  | 18.01123 | 26.96964  | [1,] | 9.924882  | 20.08719 | 29.90171  |
| [2,] | 17.924563 | 36.04534 | 53.98549  | [2,] | 19.872031 | 40.17834 | 59.86737  |
| [3,] | 26.920336 | 53.94035 | 81.06428  | [3,] | 29.961619 | 59.62570 | 90.19134  |
| [4,] | 35.865694 | 72.06470 | 108.01636 | [4,] | 39.797839 | 80.17582 | 119.87475 |
| [5,] | 44.777038 | 89.89133 | 134.84858 | [5,] | 49.733276 | 99.80670 | 149.77195 |
| Slice $\hat{A}_{:,:,1}$ | | | | Slice $\hat{A}_{:,:,2}$ | | | |

However, the tensor A can be rebuilt using only vectors $a_1$ rather than $a_1$ and $a_2$. Although the resultant approximation has a higher error, it still captures most of the information represent by A:

$$\hat{A} = \lambda_1 a_1^{(1)} \circ a_1^{(2)} \circ a_1^{(3)}.$$

|      | [,1]      | [,2]     | [,3]           |      | [,1]      | [,2]     | [,3]       |
|------|-----------|----------|----------------|------|-----------|----------|------------|
| [1,] | 8.95873   | 17.98877 | 26.98287       | [1,] | 9.950363  | 19.97770 | 29.96624   |
| [2,] | 17.93369  | 36.00612 | 54.00860       | [2,] | 19.916531 | 39.98714 | 59.98007   |
| [3,] | 26.90311  | 54.01435 | 81.02066       | [3,] | 29.877657 | 59.98645 | 89.97872   |
| [4,] | 35.87455  | 72.02664 | 108.03880      | [4,] | 39.841025 | 79.99027 | 119.98411  |
| [5,] | 44.77559  | 89.89757 | 134.84490      | [5,] | 49.726202 | 99.83710 | 149.75404  |
|      | Slice $\hat{A}_{:,:,1}$ | | |      | Slice $\hat{A}_{:,:,2}$ | | |

As demonstrated above, the tensor A can be approximated using only a, vectors. If the resultant accuracy is sufficient, the decomposition effectively compresses tensor A approximately 6-fold —it takes 60 numbers to encode the original tensor but only 11 numbers to encode the compressed tensor $\hat{A}$ (vectors $a^{(1)}$, $a^{(2)}$, $a^{(3)}$ and value of $\lambda$). The decomposed form of the tensor can be further used for tensor-to-tensor comparison, as well as an input for supervised machine learning methods, such as, for example, to support vector machine learning.

It should be noted that simple CP decomposition and the more complex Tucker decomposition, although most commonly used for expressing the content of tensor-arranged information in a simpler, easier-to comprehend form, are not the only methods useful in decomposing tensors. Other tensor decomposition methods can be also used with the screening data, as long as the organization of the datasets follows an acceptable convention.

Moreover, as mentioned above, tensor decomposition can be applied to higher-order tensors. In this case the multiple measurements performed for multiple compounds will be decomposed along the modes of a tensor, revealing the crucial differences between compounds. Also, multiple repeats of the same tested compound can be used, effectively leading to computation of a synthetic "averaged" compound fingerprint which can then be compared to other fingerprints.

Automated Gating Based on Morphology

An embodiment provides for the use of model driven automatic gating (although, the use of gating algorithms is optional). Herein, state-of-art techniques of mixture modeling with or without proprietary additions may be added to the algorithm. The system may rely on an iterative approach to improve efficiency of the assay.

In an embodiment, the gating technique comprises 3 skew-normal probability distributions representing "live cells," "dying cells," and "dead cells" (debris). Depending on the data, an existing (e.g., old validated) model may be used or a new generated based on the controls. For example, it is possible to proceed by calculating the total log-likelihood (LL) for each mixture model. Specific models for which LL is higher are then retained for future use.

Compound Dissimilarity

Compound dissimilarity measurements can be performed after decomposition of an individual compound fingerprint, following a decomposition of a result tensor in which all the compounds (and all the measurement repeats) are stored, or directly using the full, "uncompressed" version of the fingerprints. If the comparison involves decomposed tensors, the problem is essentially reduced to comparison of vectors.

However, as mentioned above, the compound fingerprint tensors can be also compared directly. In this case the dissimilarity between compound tensors is expressed as a vector storing dissimilarities (distances) between mode-1 fibers $a_{:jk}$ of the compound tensor A. Since the fibers $a_{:jk}$ store information about responses of cell cultures exposed to increasing concentrations of the tested compounds, the values form a series, which can be viewed as a polygonal curve. Consequently, the tensor-oriented arrangement of data allows us to utilize distances between discrete curves (vectors).

One such distance is the discrete Fréchet distance, which is defined as the minimal length of a leash necessary for the dog and the handler to move from the starting points of the two curves describing their paths to the endpoints, provided that both dog and the handler can only move forward, although they can control their speed. Since the fibers can be viewed as polygonal curves, in this setting both the dog and the handler can only stop at vertices of the curves and each of them can either stay at their current vertex or jump to the next one while walking. See Aronov et al., "Fréchet Distance for Curves," Revisited, in: Azar, Y., Erlebach, T. (Eds.), *Algorithms —ESA* 2006, *Lecture Notes in Computer Science*. Springer Berlin Heidelberg, pp. 52-63, 2006, which is incorporated by reference herein in parts pertinent thereto.

A conceptually similar distance measure is dynamic time warping distance, which measures distance between two polygonal curves by warping them in a non-linear fashion in order to find the best alignment. The cost of performing the alignment is defined as the distance value. See Berndt and Clifford, "Using dynamic time warping to find patterns in time series," *AAAI94 Workshop on Knowledge Discovery in Databases*, pp. 359-370, 1994, which is incorporated by reference herein in parts pertinent thereto.

Therefore, in a general case we can express the dissimilarity between two compound fingerprints (tensors) A and B as:

$$w_{A,B} = D(A,B) = d(a_{:jk}, b_{:jk}),$$

where D is the dissimilarity between compound tensors A and B, d is the distance function comparing mode-1 fibers of each of the tensors (such as Fréchet distance or dynamic time-warping distance), and w is the distance vector. For a three-way tensor produced by experiments involving a 10-dose response curve, four parameters and positive and negative controls, the vector w would have a length of 8. Every element of the vector would be computed as a curve-distance between corresponding fibers of tensors A and B.

Graphical Representations of Compound Dissimilarities

Similarities/dissimilarities between compounds can be demonstrated graphically using various methods depending on the function used to evaluate the dissimilarity. An example is illustrated FIG. 11. If an abbreviated compound fingerprint can be expressed as a vector after a decomposition (formed by multiple concatenated vectors), then one may apply an *a. priori* chosen distance between vectors, or train a distance function using metric learning methods. See Weinberger and Saul, "Distance metric learning for large margin nearest neighbor classification," J. Mach. Learn. Res. 10, 207-244, 2009, which is incorporated by reference herein in parts pertinent thereto. The final result can be visualized using multidimensional scaling (MDS), hierarchical clustering, or manifold learning methods.

If decomposition/compression is not used, the visualization of similarities between compounds requires an approach utilizing vectors of dissimilarities, rather than scalar measures of dissimilarity. One such method is multi-mode MDS algorithm utilizing stress majorization. See Leeuw and Mair, "Multidimensional Scaling Using Majorization: SMACOF," R. J. Stat. Softw. 31, 1-30, 2009, which is incorporated by reference herein in parts pertinent thereto.

Utilizing the formed dissimilarity matrices by multi-way multi-dimensional scaling techniques place the measured compound signatures in a space defining inter-compound similarity. See, Groenen et al. ("The majorization approach to multidimensional scaling for Minkowski distances." J. Classif. 12, 3-19, 1995), which is incorporated by reference herein. The compounds localized close in the resultant space will be deemed "similar" in the sense of the described process, and the compound located far away will be considered "dissimilar."

Comparison of Distributions Using Multiple Cellular Subsets

The control versus tested sample dissimilarity can be computed employing all the measured instances (cells) or calculated separately for each functionally defined subset of the cellular population. For instance, one may define two morphologically distinct subsets of cells on the basis of the measured light scatter. In this setting the two cellular subsets may be compared to the controls separately. What follows is that the number of comparisons is dependent on the number of formed subsets. For instance, if five functional labels are designated to demonstrate five different aspects of cell physiology, and one chooses to compare the treated outcome to untreated outcome for each of the morphologically different cell populations, one can produce up to 20 different distances (5 labels×2 controls×2 cellular subsets).

Since the concentration of the perturbant resulting in the desired physiological effect cannot be ascertained a. priori, a function describing the gradual increase of the effect with the perturbant concentration can be used to indicate properties of the perturbant, the measurement being performed with several concentrations of a drug. Therefore, for the scenario outlined above, assuming the use of 10 concentrations, the final data set would comprise 200 values (5 labels×2 controls×2 subpopulations×10 concentrations). The measured values are not independent; therefore, they are treated for further processing as a multi-way tensor. For instance, if only one type of control is used (e.g., a "positive" control), the data set would form a three-way tensor with the dimensions of 5×10×2. FIG. 14 shows an example of a multiway tensor representing a drug response fingerprint.

Use of a Multi-Dimensional Feature Space

In an embodiment of the present invention, the evolution of a point-cloud in a multidimensional feature space can be computed by directly computing distances between distributions. Examples of point clouds that evolve in a multi-dimensional feature space include, but are not limited to, for example, variables such as drug concentration, incubation time, etc. The changes in evolution of the cloud in the space defined by dissimilarities between complex point-clouds form a complicated trajectory, which uniquely describes the characteristics of the compound eliciting those changes.

A representative cloud evolution is shown in FIG. 15.

Comparison of Distributions Using Cell-Cycle Information

In embodiments, fingerprint tensors are created for each of the clusters or cellular subsets defined by cell-cycle-dependent labels. In this setting, the assessment of cell-cycle phases is performed simultaneously with other measurements such as by quantifying the intensity of fluorescence labels intercalating into DNA (such as HOECHST 33342, DRAQ5, YO—PRO-1 IODIDE, DAPI, CYTRAK ORANGE), by quantifying the presence of immunolabeled proteins associated with the cell cycle (e.g., cyclins, phosphorylated histone proteins, etc.), or by measuring the signal of genetically encoded fluorochromes linked to cell-cycle phases. In the simplest case, these techniques allow one to determine three compartments of the cell cycle, leading to the formation of a 5×10×3 result tensor (or more complex tensors, depending on the number of additional labels). This is illustrated in Example 5A.

Unsupervised and Supervised Classification

Embodiments provide classification methods, wherein subsequent analyses are performed using multiple approaches. These analytical techniques may be implemented depending on the preferred final representation or visualization of the results. For instance, in the unsupervised setting, the distance tensor can be processed by a multi-mode multidimensional SMACOF (Scaling by MAjorizing a COmplicated Function) algorithm or other suitable mathematical technique for scaling. After application of the MDS method, the drug fingerprints will be placed onto a 2-D plane or onto any other n-dimensional surface (e.g., sphere) defined by the researchers. This allows easy interpretation and visualization of the data sets, which form a "map" upon MSD projection.

In the supervised framework, the fingerprints representing compounds belonging to various groups defined by function, response type, chemical structure, etc., are used to create a training library with multiple classes. The training library can subsequently be used to train a classifier (such as a neural-network classifier, support-vector machine, or another type of machine-learning system) that will categorize previously unknown fingerprints into classes defined by known compounds.

By extension, related embodiments of the present invention provide methods for assessing the effects of unknown perturbants (not known a. priori to impact MMP) to determine if they have a differential impact on MMP (and other cell physiology measurements, e.g., SYTOX™ RED low versus high cells) in different cell cycle phases. Therefore, for every tested compound, there is provided a multi-way measurement tensor (compound signature) which comprises cell cycle-related state tensor as one of the dimensions in which the cell state is evaluated.

The following is a representative method for comparing different perturbants using the systems and the algorithms of the instant invention:

First, for each fluorescence channel (for example, separately for live cells and dying cells), a distance matrix between all compounds is created using the above-described technique. For example, the distance can be the dynamic time warping distance (dtw) between response curves. Subsequently, a multi-way multi-dimensional scaling (MDS) is used to combine several matrices into an Euclidean space. Then, the MDS for one group of matrices containing only MMP data (CALCEIN, SYTOX™) and another group with only permeability data (MBBR, MITOSOX™) may be calculated. The various physiological similarities between the compounds may be visualized with the help of known mapping and clustering techniques, e.g., dendograms or graph visualization (e.g., creating intermediary nodes and exporting the data to any one of a variety of external visualization software packages. Furthermore, supervised approach using one or more classifiers may also be employed.

Cell Cycle

Embodiments herein described allow measurements of coordinated protein (or other marker) expression in populations of cells as a function of cell cycle (e.g., G1, S, G2M), and to determine cell-cycle-dependent effects of the test compounds. Multi-parametric analysis may thus be conducted by analyzing the effect of each perturbant at different concentrations and/or time points to investigate the effect of said compounds on the various cellular parameters (e.g., mitochondrial membrane potential, nuclear or cytoplasmic membrane permeability, ROS, cell death or apoptosis).

An example of cell-cycle dependent analysis is based on the measurement of Cyclin A2 expression in normal (unperturbed) cells. Herein, the possible "states" include Cyclin A2 negative, Cyclin A2 low and Cyclin A2 high. Similarly, for phospho-histone 3 (P—H3), which is a second marker in cell-cycle analysis, the possible "states" include "negative" and "positive". These two cell-cycle markers may also be analyzed in combination, thus yielding nine different possible combinations ("states"). It is not always necessary to investigate all possible "states" because all the states may not exist in normal biological space (sparse matrix).

Accordingly, depending on the cell cycle state a particular cell is in, differential perturbations caused by drugs or compounds of interest can be investigated by populating cells in discrete (normal) matrix elements. As an example, drugs which block normal progression from mitosis back into G1, which cause quantitative changes in "normal" matrix populations (i.e., accumulation of cells into "late" (normal) cell cycle compartments (e.g. G2 and M)) and/or deplete cells in the G1 phase, can be analyzed in concert using Cyclin A2 and/or P—H3 staining. Similarly, a drug which prevents separation of daughter nuclei would be expected to show a different quantitative fingerprint pattern compared to a drug which arrests cells in S-phase (e.g., a drug which inhibits new DNA synthesis). Accordingly, compounds which cause cells to appear in different matrix elements not only creates a unique signature, but also the specific matrix element that is occupied could provide information regarding the mechanism of drug action. For example, expression of Cyclin A2 in G1 and or M can be the result of a proteasome inhibitor preventing normal Cyclin A2 degradation.

Multiple Cell Type Assay System

In an embodiment, the present invention provides for methods for assaying cellular states using a plurality of cell types, e.g., two or more cell lines (from tissue culture) in a single assay. One advantage of this approach is it allows analyses of DNA damage/responses. An additional advantage is that it allows studies of both constitutive and inducible signaling pathways in the same assay (using one cell line with constitutive expression and another that can activate the same pathway using an appropriate agonist). Using two (or more) cell lines simultaneously, it will be possible to cover multiple signaling pathways in one assay.

For example, using human myeloid cell lines (derived from patients with myeloid leukemia), one cell line responsive to LPS will activate NF-κB and PI3 Kinase pathways, while another responsive to TNF-α will activate multiple MAP kinase pathways; in both cases, upstream (Iκ kinase for NF-κB) and downstream (P-S6 for ERK and mTOR for PI3K) can be evaluated. In addition, these assays can include DNA damage/response markers, as indicated above. The responding cell line in cell mixtures can be identified using either DNA content (some cell lines are diploid; others are aneuploid with different abnormal DNA content), or biological characteristics (cell surface markers), or cells can be "barcoded" (G. Nolan et al.). Finally, signaling assays can include cell cycle analysis (e.g., DNA content) to allow correlation of signal transduction pathway responses with cell physiology in response to the same drugs.

EXAMPLES

The following examples are provided by way of illustration only by means of various particular embodiments and are in no way exhaustive or exclusive.

General Methodology of the Following Examples

Tissue Cultures

Human tissue culture cells were obtained from Sigma-Aldrich (St Louis, MO, USA) as frozen stock. Cell lines are thawed and initially placed into static culture, followed by continuous culture in 1 L roller bottles, in RPMI 1640/10% FBS/Glut (±0.5-2 mM)/Penn/Strep. Cells for in vitro screening assays were maintained in log phase growth under highly standardized conditions (input and harvest cell density, viability, etc.).

Preparation of Cell Physiology Assay Plates 1a and 1b

Cells were deposited into 384 well plates ($1\times10^6$ cells in 40 µl tissue culture media), and serial dilutions of test compounds (or vehicle in the case of controls) were deposited in individual wells using standard robotic techniques. Compound deposition and dilution was performed by BIOMEK FX (5 or 10-step dilutions from 100 to 0.005 µM). Dilutions were prepared from stock solutions of compounds dissolved initially in 100% DMSO. Final volume deposited into each well is 2 µl of each compound dilution (compounds are in a final concentration of 1% DMSO). After incubation in a tissue culture incubator (5% $CO_2$ at 37° C.) for varying periods of time (typically 4 hours), plates were centrifuged at room temperature, followed by removal of 20 µl supernatant fluid. After vibration of the plate to re-suspend cells, a dye mix (Plate 1a Monobromobimane, CALCEIN AM, MITOSOX™ and SYTOSOX™ RED; plate 1b VYBRAN-VIOLET™ Live Cell Cycle dye, JC-9, and SYTOSOX™ RED) was added in a total volume of 20 µl, followed by an additional mixing step. Plates were returned to the tissue culture incubator (5% $CO_2$ at 37° C.) for an additional 15 min (plate 1a) or 30 min (plate 1b), followed by immediate analysis using the HYPERCYT-CYAN™.

Preparation of Cell Cycle or Cell Signaling Assay Plates 2 and 3

Cells were deposited onto dilutions of test compounds deposited into individual wells of 96 well plates, as indicated above. Following incubation in a tissue culture incubator (5% $CO_2$ at 37° C.) for 30 minutes to 12 hr, the cells were pelleted by centrifugation, the supernatant was removed, the cells were re-suspended by vibration in the remaining supernatant fluid, and 50 µl of fixative (1.2% formaldehyde in PBS) was added. Following 15 min incubation (at 37° C.), cells were pelleted by centrifugation, supernatant removed, and the cells were suspended by vibrating the plate.

Cell were permeabilized by adding 150 μl cold absolute methanol, followed by incubation at 4° C. for 15 minutes. Permeabilized cells were centrifuged, supernatant removed, and cells were washed three times with cold (4° C.) PBS containing 4% FBS. Following the final wash, cells were centrifuged, the supernatant was removed, and cells were re-suspended in an antibody cocktail (total volume 20 μl) appropriate for that experiment.

For DNA content/cell cycle analysis, cells were resuspended (following washes to remove unbound antibody conjugates) in PBS/FBS containing DAPI (1 μg/ml), followed by analysis using the HYPERCYT-CYAN™.

HYPERCYT-CYAN High Throughput Flow Cytometry

Each well of the 384-well plate was sampled with a 6 second sip time, plus 1 second delay between wells, resulting in a total read time for each plate of approximately 45 minutes. Data was acquired using a CYAN™ flow cytometer, with the HYPERCYT™ software used to compile files for each well on an individual plate using an FCS format. Data for each plate was subsequently analyzed for several quality assurance parameters (total number of events per well, numbers of events associated with morphologically normal events, number of dead cells), as described below.

Example 1 Normal Cells

Flow cytometric analyses of intrinsic cell properties (forward light scatter and light scattered orthogonal to the laser beam) and fluorescence signals derived from the dyes listed in Table 1 was carried out for plates 1a and 1b.

TABLE 1

List of dyes used in Plates 1a and 1b with physiologic targets

| Dye | Plate | Physiologic Response |
|---|---|---|
| Monobromobimane (MBBR) | 1a | Cellular/nuclear-SH (predominantly Glutathione (GSH) |
| CALCEIN AM | 1a | Cytoplasmic membrane permeability |
| MITOSOX RED ™ | 1a | Reactive Oxygen Species (related to mitochondrial function) |
| SYTOXRED ™ | 1a and 1b | Cytoplasmic and nuclear membrane permeability (live/dead) |
| VYBRANVIOLET ™ | 1b | Cell cycle measurement including viable cells |
| JC-9 | 1b | Mitochondrial membrane potential (MMP) |

™ MOLECULAR PROBES/INVITROGEN

Figure 1A:
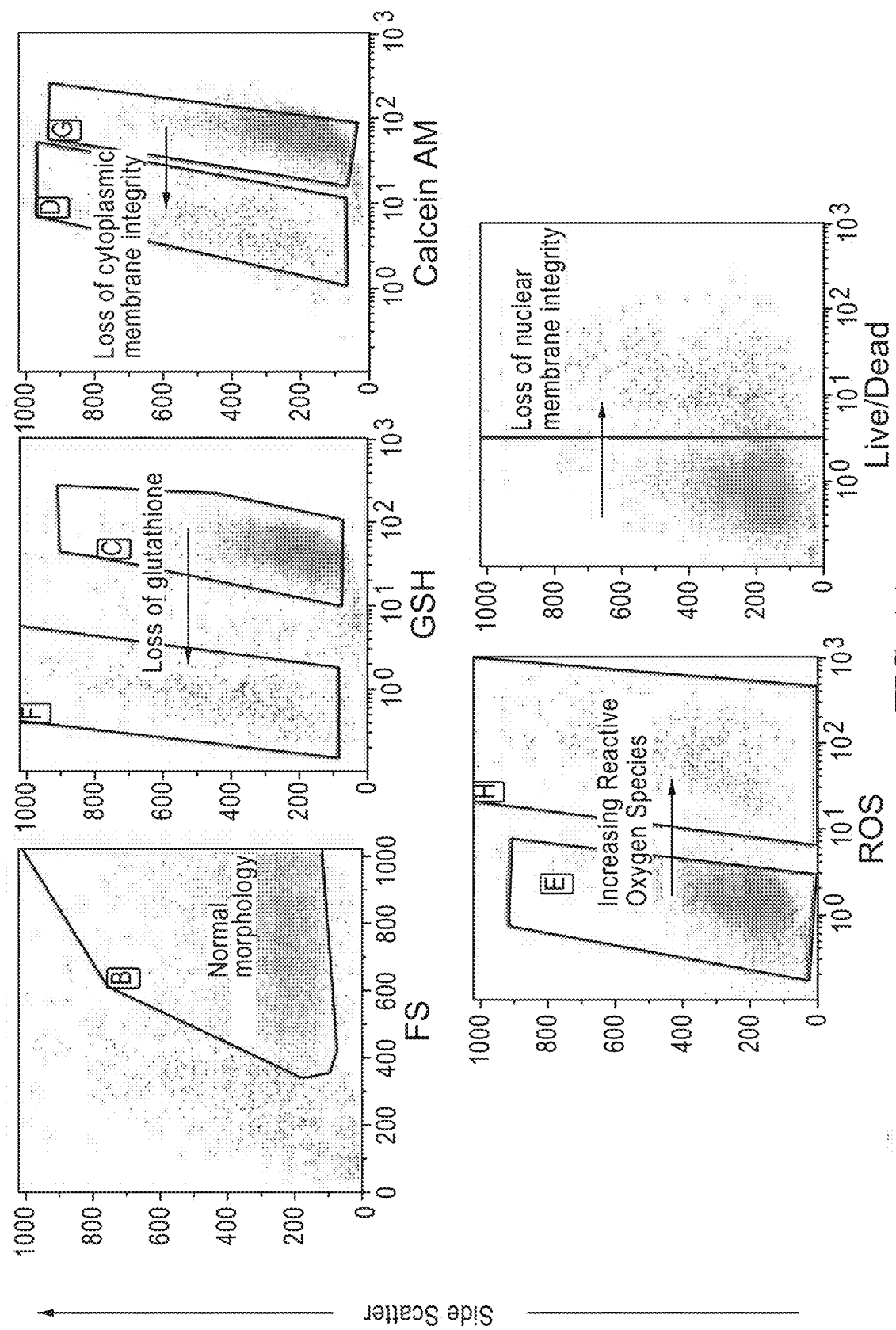
FIG. 1A shows cytometric profiles of normal cells as described in Example 1. Cells were specifically labeled to measure cellular/nuclear thiol levels, predominantly glutathione (GSH) levels, as measured with monobromobimane (MBBR). Cells were stained using various fluorescence dyes, as described in Example 1. Cytoplasmic membrane permeability is measured with CALCEIN AM; Reactive Oxygen Species (ROS; related to mitochondrial function) is measured with MITOSOX RED™; Cytoplasmic and nuclear membrane permeability (live/dead) is measured with SYTOXRED™.

The results are shown in the scatter plot in FIG. 1A. As seen in the plot, light scatter alone allows the identification of cells having "normal" morphology. Cells in this figure are not treated with any drug, and the majority of cells (here, greater than 95% of all events) show "normal" morphology.

Cells shown in this figure were also treated with a dye mixture of Table 1 as follows:

(1) Monobromobimane (MBBR) to measure intracellular glutathione (GSH) content, as described previously in Cossarizza et al. ("Simultaneous analysis of reactive oxygen species and reduced glutathione content in living cells by polychromatic flow cytometry." *Nat. Protoc.* 4, 1790-1797, 2009); Kosower et al. ("Bimane fluorescent labels: labeling of normal human red cells under physiological conditions." *Proc. Natl. Acad. Sci. U.S.A* 76, 3382-3386, 1979); Radkowsky et al. ("Bimanes. 17. (Ilaloalkyl)-1,5-diazabicyclo[3.3.O]octadienediones (halo-9,10-dioxabimanes): reactivity toward the tripeptide thiol, glutathione." *J. Am. Chem. Soc.* 108, 4527-4531, 1986);

(2) CALCEIN AM to measure cytoplasmic membrane integrity, as described in Ivnitski-Steele et al. ("High-throughput flow cytometry to detect selective inhibitors of ABCB1, ABCC1, and ABCG2 transporters." *Assay Drug Dev. Technol.* 6, 263-276, 2008). CALCEIN AM is a nonfluorescent compound that passes through the cytoplasmic membrane, and in living cells, the compound is converted into a strongly green fluorescent compound which cannot pass through the cytoplasmic membrane; if cells subsequently loose cytoplasmic membrane integrity, the fluorescent compound leaves the cell by passive diffusion;

(3) MITOSOX™ RED to measure intracellular reactive oxygen species, as described in Zielonka et al. ("Detection of 2-hydroxyethidium in cellular systems: a unique marker product of superoxide and hydroethidine." *Nat. Protoc.* 3, 8-21, 2008). MITOSOX™ RED is a compound that can diffuse into viable cells and reacts with superoxide anion species, particularly products of mitochondrial respiration; conditions such as cell stress can cause mitochondria to respond (sometimes rapidly) by increasing respiration and/or release superoxide anions; and (3) SYTOXRED™ to measure cell viability (loss of nuclear membrane integrity). SYTOXRED™ is a high-affinity DNA stain that can only pass through the cytoplasmic and nuclear membranes of cells which have lost the integrity of both membranes; thus, brightly fluorescent cells are dead.

Based on the specific perturbation, cells can lose (or in some cases gain) intracellular GSH, resulting in a loss (or gain) of fluorescence signal.

Figure 1B:
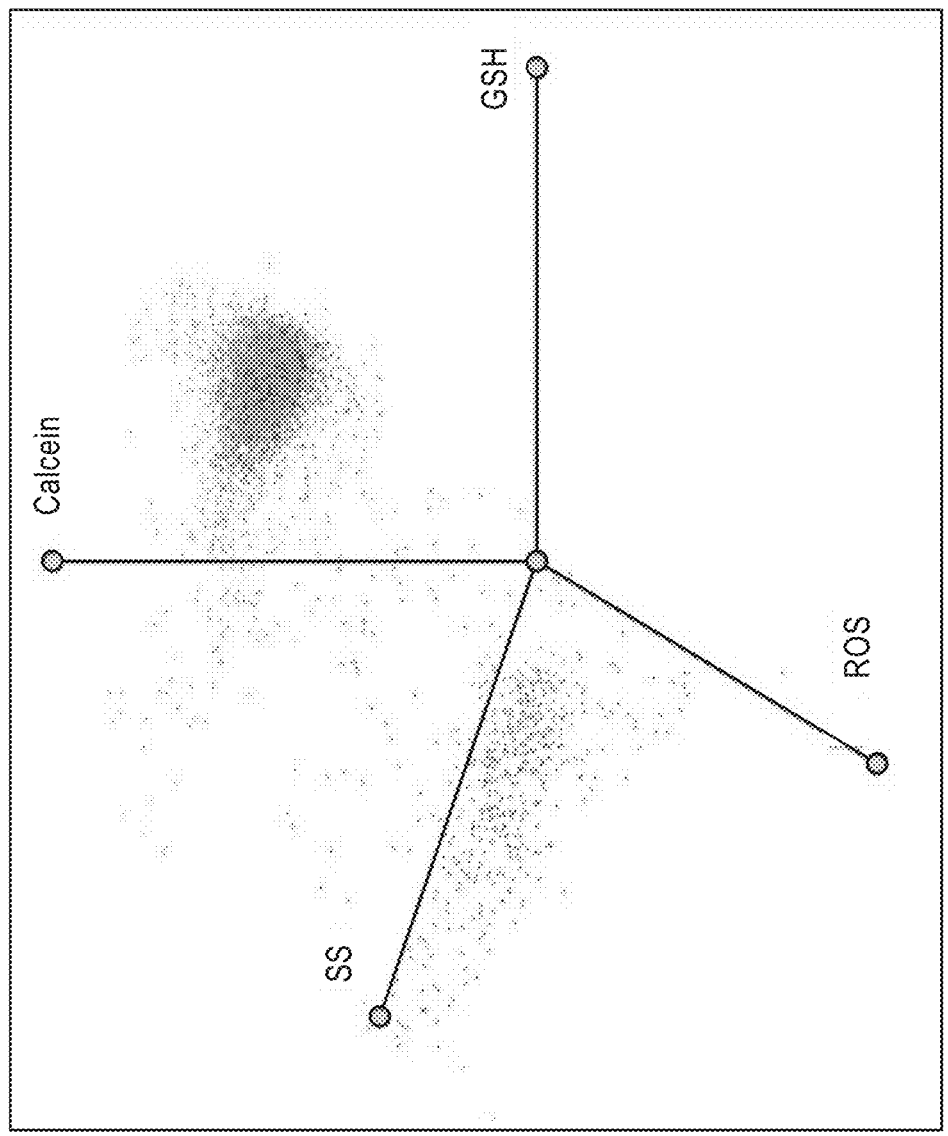
FIG. 1B shows the data of FIG. 1A in the form of a "radar" plot.

The parameter tensors for the cloud plot population of normal cells were calculated and are depicted or described graphically in FIG. 1B.

Example 2: Cells Treated with Myxothiazol, FCCP and Fluoxetine

Cells were treated with a perturbant (e.g., myxothiazol, FCCP and fluoxetine) and analyzed as described in Example 1.

Figure 2:
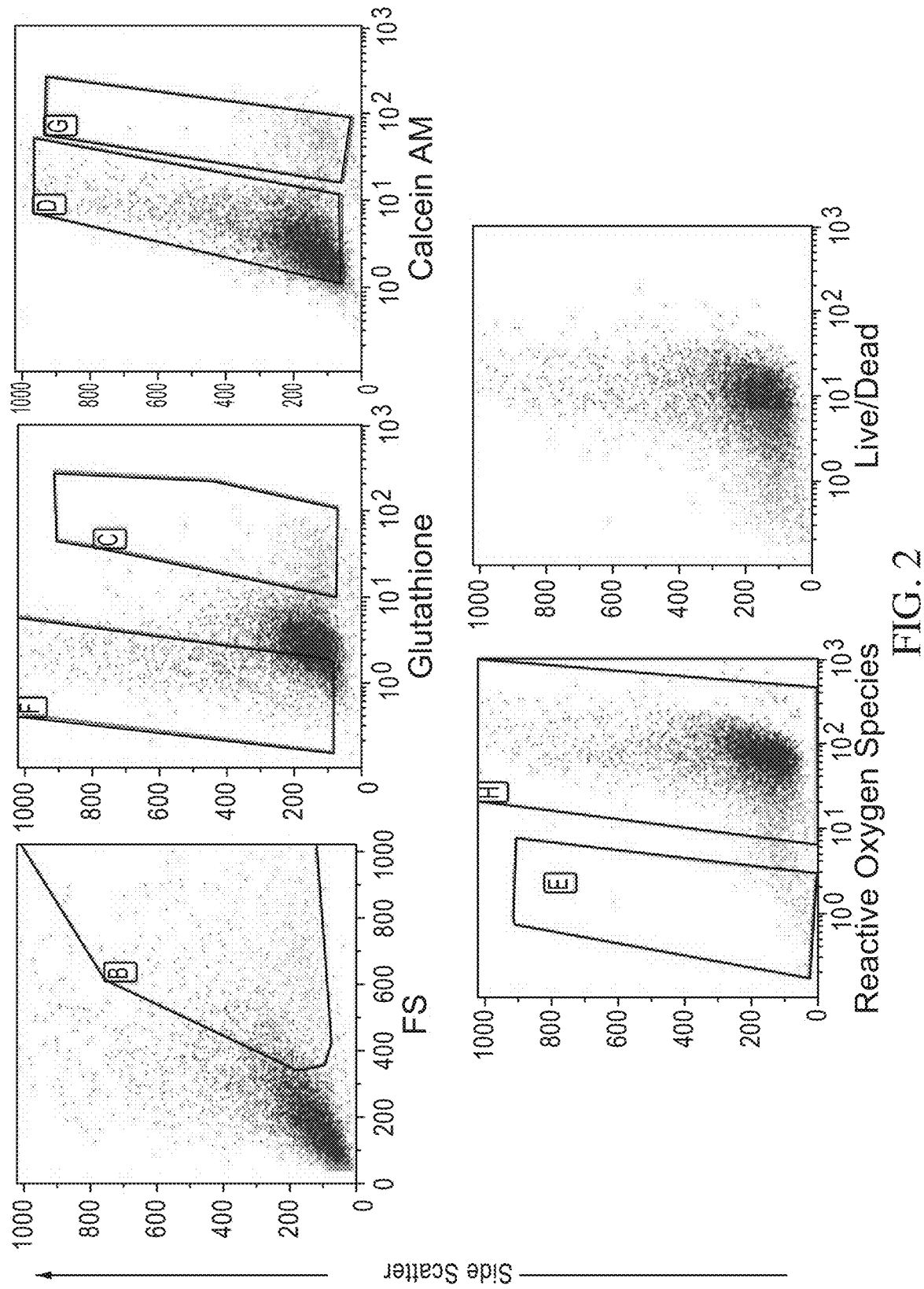
FIG. 2 is a set of plots of cells treated with 100 µM myxothiozol (an inhibitor of the mitochondrial cytochrome bc1 complex) analyzed as described in Example 2 for forward scatter (FS), glutathione, CALCEIN AM, ROS and cell viability. Comparing FIG. 1A to FIG. 2 shows that treatment with 100 µM myxothiozol perturbs cytoplasmic and nuclear membrane permeability (viability).

The effects of exposing cells to 100 μM myxothiazol are shown in FIG. 2. Treatment of the cells with myxothiazol resulted in a significant change in cell morphology (upper left panel), decrease in GSH and CALCEIN AM (upper middle and right panels), and an increase in ROS and SYTOXRED™ (lower panels) in the majority of cells (dark blue in all panels). Each of these responses is visually different from the pattern for each dye in "normal" cells, as shown in FIG. 1A.

Figure 3:
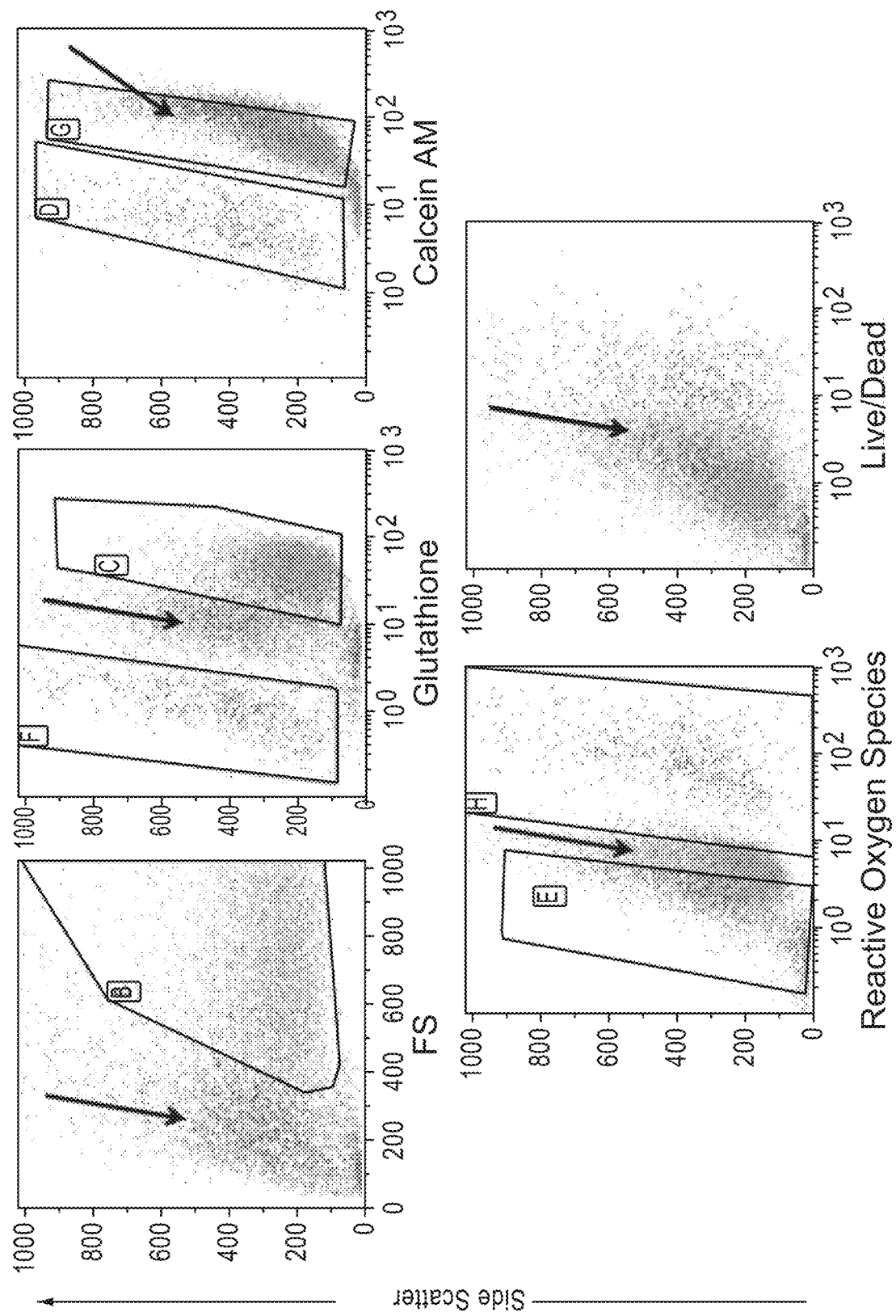
FIG. 3 is a scatter plot of cells treated with 33 µM carbonyl cyanide-4-(trifluoromethoxy)phenylhydrazone "FCCP", an ionophore mobile ion carrier that acts as an uncoupling agent in the mitochondria) analyzed as described in Example 2 for forward scatter, glutathione, CALCEIN AM, ROS and viability. Arrows indicate a shift in the cellular parameter compared to control population displayed in FIG. 1A.

Exposing cells to 33 μM FCCP elicited a different response curve, which is shown in FIG. 3. The results demonstrate yet another pattern, distinct from the "normal" pattern and from the pattern for 100 μM myxothiazol. A distinct population of cells with "normal morphology" is present after treatment with FCCP (green cells in upper left panel); these same cells are colored green in all panels, and as shown, with normal GSH and CALCEIN AM levels (upper center and right panels), and intact nuclear and cytoplasmic membranes, as determined by lack of SYTOX™ Red uptake (lower right panel). However, the cells treated with FCCP have increased ROS (an indicator of mitochondrial stress; lower left panel). In addition, there is a distinct population of cells showing altered morphology, reduced GSH, increased CALCEIN, increased ROS and higher SYTOXRED™ (shown in all panels in FIG. 3 as cells colored light blue) compared to cells with "normal morphology."

Figure 4A:
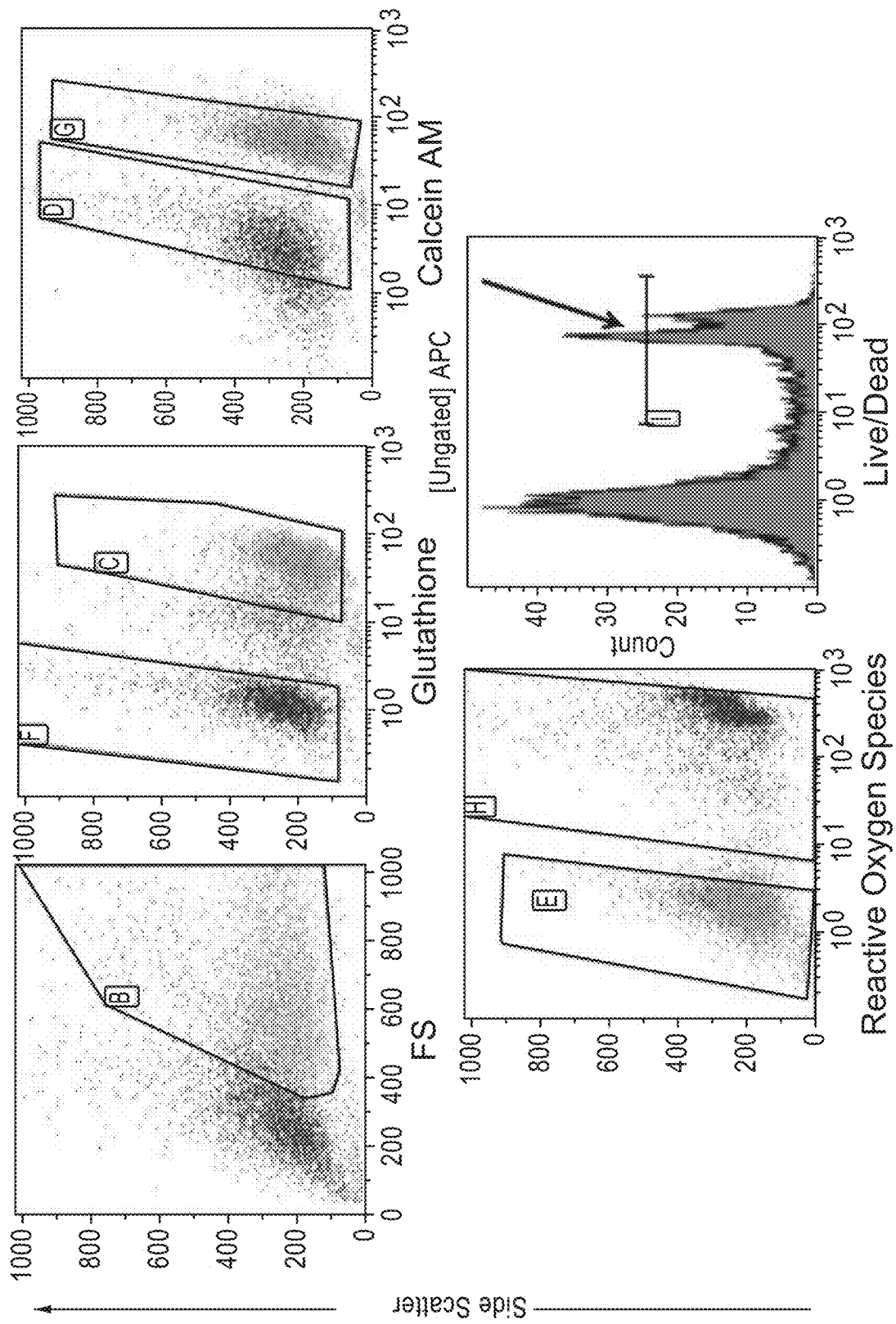
FIG. 4A is a scatter plot of cells treated with 100 µM fluoxetine (a selective serotonin reuptake inhibitor) analyzed as described in Example 2 for forward scatter, glutathione, CALCEIN AM, ROS and viability.

Yet another response pattern is shown in FIG. 4A for cells exposed to 100 μM fluoxetine. Approximately 30% of the cells have lost "normal morphology", show reduced GSH, reduced CALCEIN AM, increased ROS and significantly higher levels of SYTOXRED™ (dark blue cells in all panels in FIG. 4A). A distinct "signature" of this response is the pattern seen in the SYTOXRED™ histogram (lower right)—all the cells with high SYTOXRED™ content show a dye uptake that is reading out the DNA content (cell cycle) of the parent HL-60 cell line, indicating that within this treatment period, cells are dying throughout the cell cycle, and have not yet degraded their DNA (a normal hallmark of apoptotic cells).

Figure 4B:
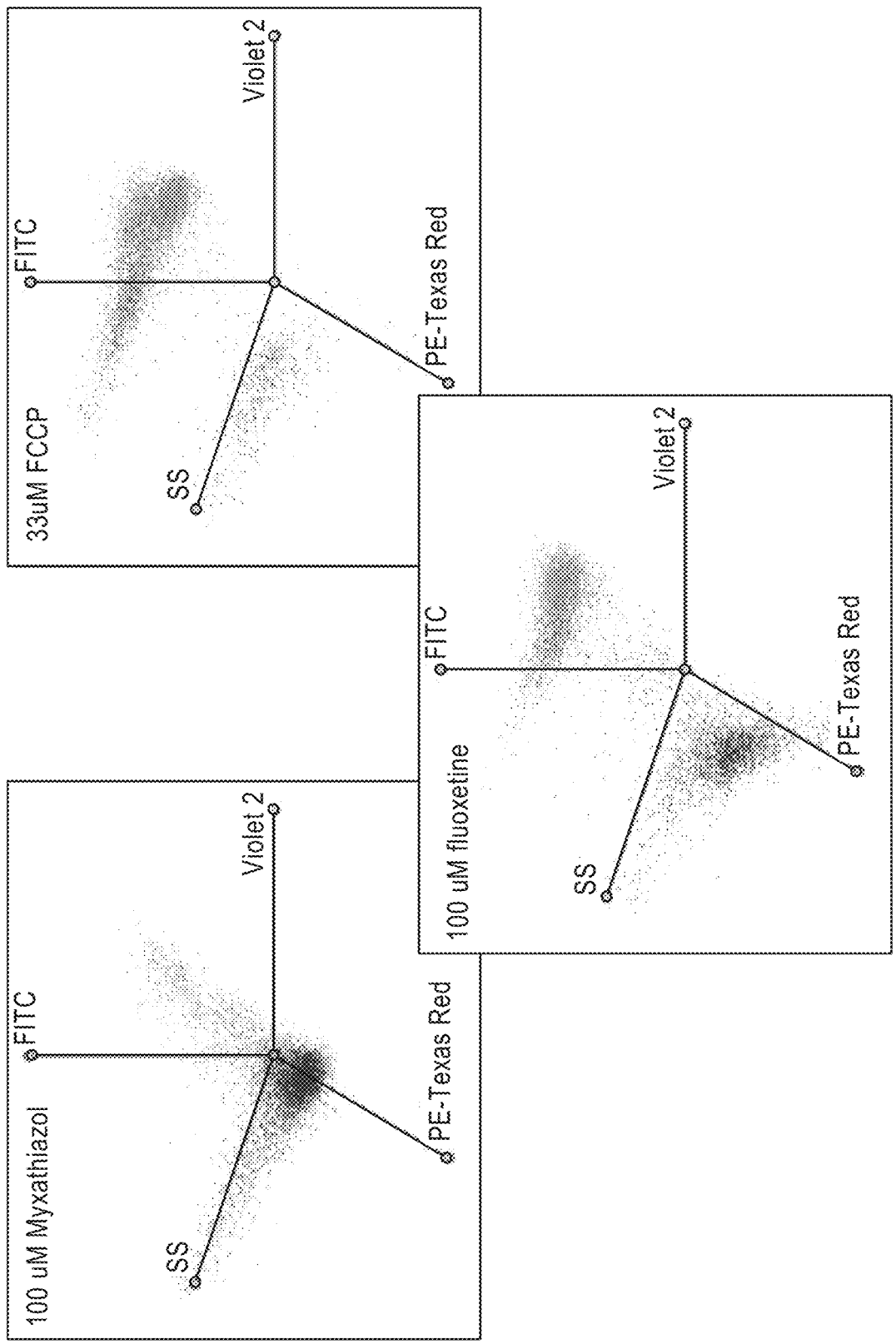
FIG. 4B is a set of multidimensional profiles of FIG. 2, FIG. 3, and FIG. 4A, plotted along four axes: one for the cells treated with 100 µM myxothiozol (top left), 33 µM FCCP (top right) or 100 µM fluoxetine (bottom center).

A set of multidimensional profiles of FIG. 2, FIG. 3, and FIG. 4A are plotted along four axes in FIG. 4B: one for the cells treated with 100 μM myxothiozol (top left), 33 μM FCCP (top right) or 100 μM fluoxetine (bottom center).

Example 3: Cell-Cycle

Measurements identical to those described in Example 2 above were made using a second combination of dyes:
(1) VYBRANVIOLET™ to measure cell cycle in live cells;
(2) JC-9 to measure mitochondrial membrane potential (MMP); and
(3) SYTOXRED™ (as described herein above).

Figure 5:
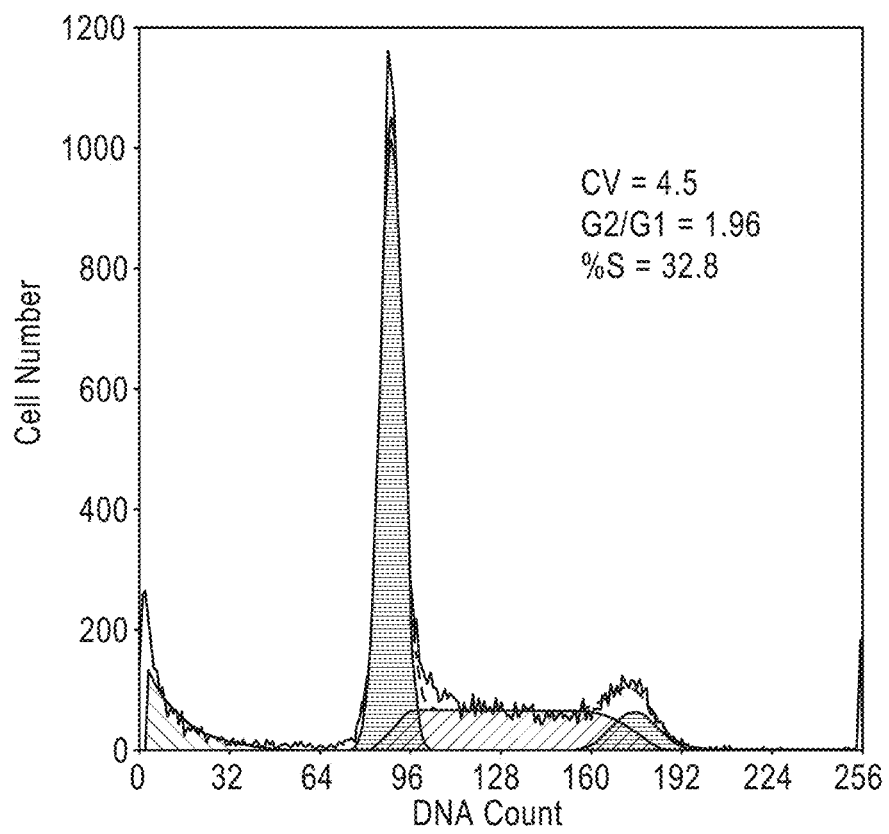
FIG. 5 shows the results of a control analysis of cell cycle stages in live HL-60 cells using VYBRANVIOLET™ dye as described in Example 3. Cell count is indicated on the vertical axis. DNA content is indicated on the horizontal axis. The purple spike on the left indicates cells in G1 phase. The broad pink area indicates cells in S-phase. The cross hatched purple peak on the right indicates cells in G2/M phase.

The cell cycle measurement of untreated cells, showing distinct populations of cells in G1, S, and G2M phases of the cell cycle, is depicted graphically in FIG. 5. A first population constituting the sharp, tall peak on the left of the graph is cells in G1. The flat middle portion of the graph arises from cells in S phase. The peak on the right of the graph is produced by cells in G2/M.

The cell cycle compartments shown here are identical to those measured in fixed HL-60 cells, demonstrating equivalency of live cell staining with "conventional" approaches using cell fixation to allow DNA binding dyes access to nuclear DNA, as described below.

Example 4A: Effect of Valinomycin

Figure 6A:
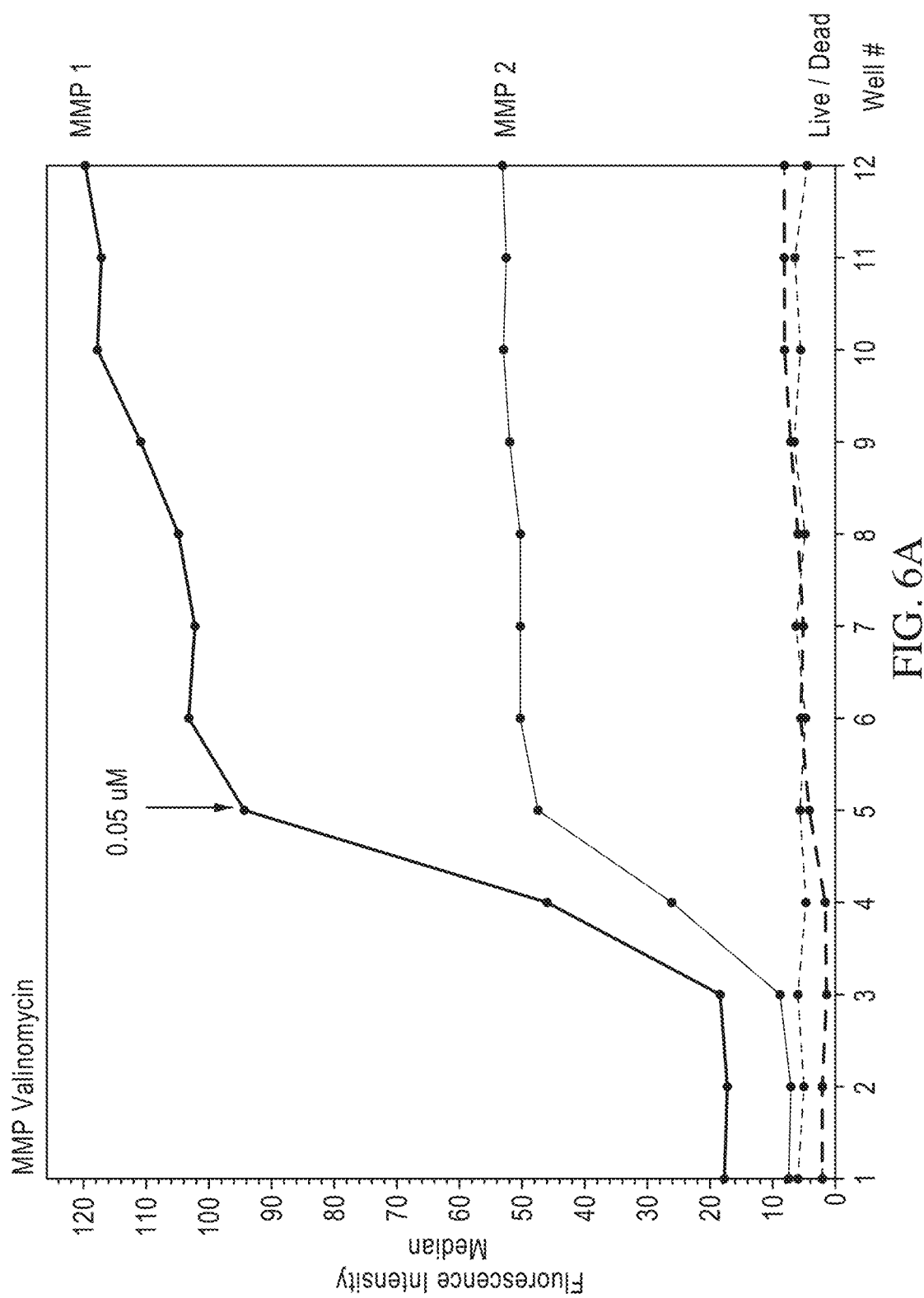
FIG. 6A is a graph showing mitochondrial membrane potential (MMP) of HL-60 cells exposed to valinomycin, which causes rapid MMP de-polarization, as described in Example 4A. Depolarization increases green and red fluorescence signals of the dye JC-9. Both red and green fluroescence is significantly higher when the cells were exposed to the valinomycin, peaking at approximately ~ 0.045 µM.

The measurement of mitochondrial membrane potential (MMP) with JC-9 was performed with two independent fluorescence channels (green and red fluorescence signals), as changes in MMP cause aggregation of the dye, with different fluorescence emission by the aggregated versus non-aggregated dye molecules. As shown in FIG. 6A, both red and green fluorescence initially increase in response to increasing valinomycin concentration, with a peak green fluorescence at~0.05 μM valinomycin. At higher valinomycin concentrations, red fluorescence increases, with the red/green fluorescence ratio increasing. A unique aspect of this assay is that it correlates changes in MMP (JC-9) and cell death (SYTOXRED™) with the phases of the cell cycle (G1, S, and G2M).

Example 4B: Effect of Idarubicin

Figure 6B:
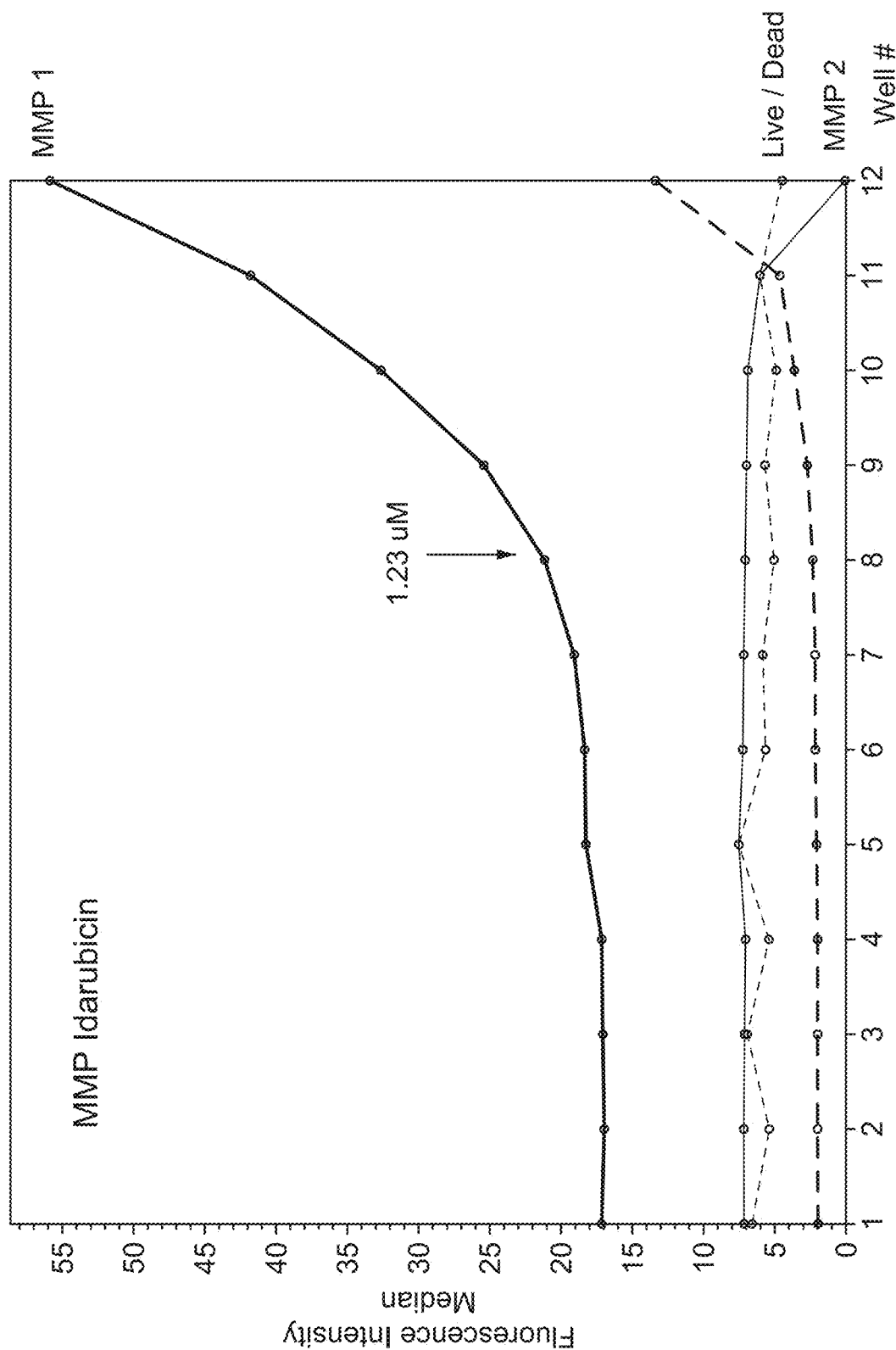
FIG. 6B is a graph showing JC-9 fluorescent in HL60 cells treated with the anthracycline antileukemic drug idarubicin, an analog of daunorubicin, as described in Example 4B. Idarubicin inserts into DNA and prevents unwinding during DNA replication. Red fluorescence of JC-9 dye begins to increase significantly at 1.23 µM idarubicin and continues to increase above that. Green fluorescence does not increase.

An identical study to the one described before was conducted with exposing HL60 cells exposed to 1.23 μM idarubicin, an analog of daunorubicin which inserts into DNA and prevents it from unwinding during DNA replication and arrests cell division. As shown in FIG. 6B, the red fluorescence of JC-9 dye is significantly higher in cells treated with idarubicin than untreated control cells (first two data points on the left indicate control cells).

Example 5: Analysis of Fixed Cells

Studies have established that mitochondria undergo significant structural changes during different phases of the normal cell cycle. See Barni et al. ("Static cytofluorometry and fluorescence morphology of mitochondria and DNA in proliferating fibroblasts." Biotech. Histochem. *Off Publ. Biol. Stain Comm.* 71, 66-70, 1996); Margineantu et al. ("Cell cycle dependent morphology changes and associated mitochondrial DNA." *Mitochondrion* 1, 425-435, 2002); Schieke et al. ("Coordination of mitochondrial bioenergetics with G1 phase cell cycle progression." *Cell Cycle* 7, 1782-1787, 2008) and Sweet et al. ("Changes in mitochondrial mass, membrane potential, and cellular adenosine triphosphate content during the cell cycle of human leukemic (HL-60) cells." *J. Cell. Physiol.* 180, 91-96, 1999), which are incorporated by reference herein in their entirety. Limited data suggests differences in mitochondrial potential ($\Delta\Psi$m) in G1 versus S+G2M populations (Schieke et al., *Cell Cycle* 7, 1782-1787, 2008); however, there are no published reports that correlate changes in MMP and cell cycle phases on the single-cell level. Moreover, there are no studies which investigate the differential effects of different chemical compounds, e.g., compounds known to change MMP, at different phases of the cell cycle. In the two illustrative embodiments described below, analysis of cell cycle (Example 5A) and signal transduction (Example 5B) was conducted using fixed cells.

Example 5A: Analysis of Cell Cycle Using Fixed Cells

Cell cycle phases can be measured in living cells using DNA binding dyes that can pass through the cytoplasmic and nuclear membranes (e.g., VYBRANVIOLET™, as shown in FIG. 5). However, this approach is sometimes problematic. Some DNA binding dyes are transported out of viable cells by cytoplasmic membrane "pumps" that remove potentially toxic compounds (e.g., P-glycoprotein transporters commonly found on cancer cells and stem-like cells). An additional problem is that the intact cytoplasmic and nuclear membranes block access to internal proteins by antibody-conjugates for fluorescence flow cytometry. To overcome these limitations, cells were fixed and permeabilized, using a combination of chemical fixatives, which prevent degradation of cellular proteins, lipids, carbohydrates as well as cellular structure. Following fixation, cytoplasmic and nuclear membranes are permeabilized using routine detergents, which process allows probe molecules (e.g. antibody-conjugates) to access intracellular compartments.

Human chronic myelogenous leukemia K-562 cells (derived from a CML line) were fixed and permeabilized using known techniques (e.g., formaldehyde fixation followed by permeabilization using methanol at minus 20° C.). These fixed cells are suitable for simultaneous measurement of DNA content (cell cycle) and intracellular and intranuclear proteins. See, for example, Pollice et al. ("Sequential paraformaldehyde and methanol fixation for simultaneous flow cytometric analysis of DNA, cell surface proteins, and intracellular proteins." *Cytometry* 13, 432-444, 1992), which is incorporated by reference in parts pertinent thereto. Following washing, fixed and permeabilized cells were incubated with one or more fluorophore-antibody conjugates, then washed to remove unbound antibodies, and analyzed by flow cytometry.

Figure 7:
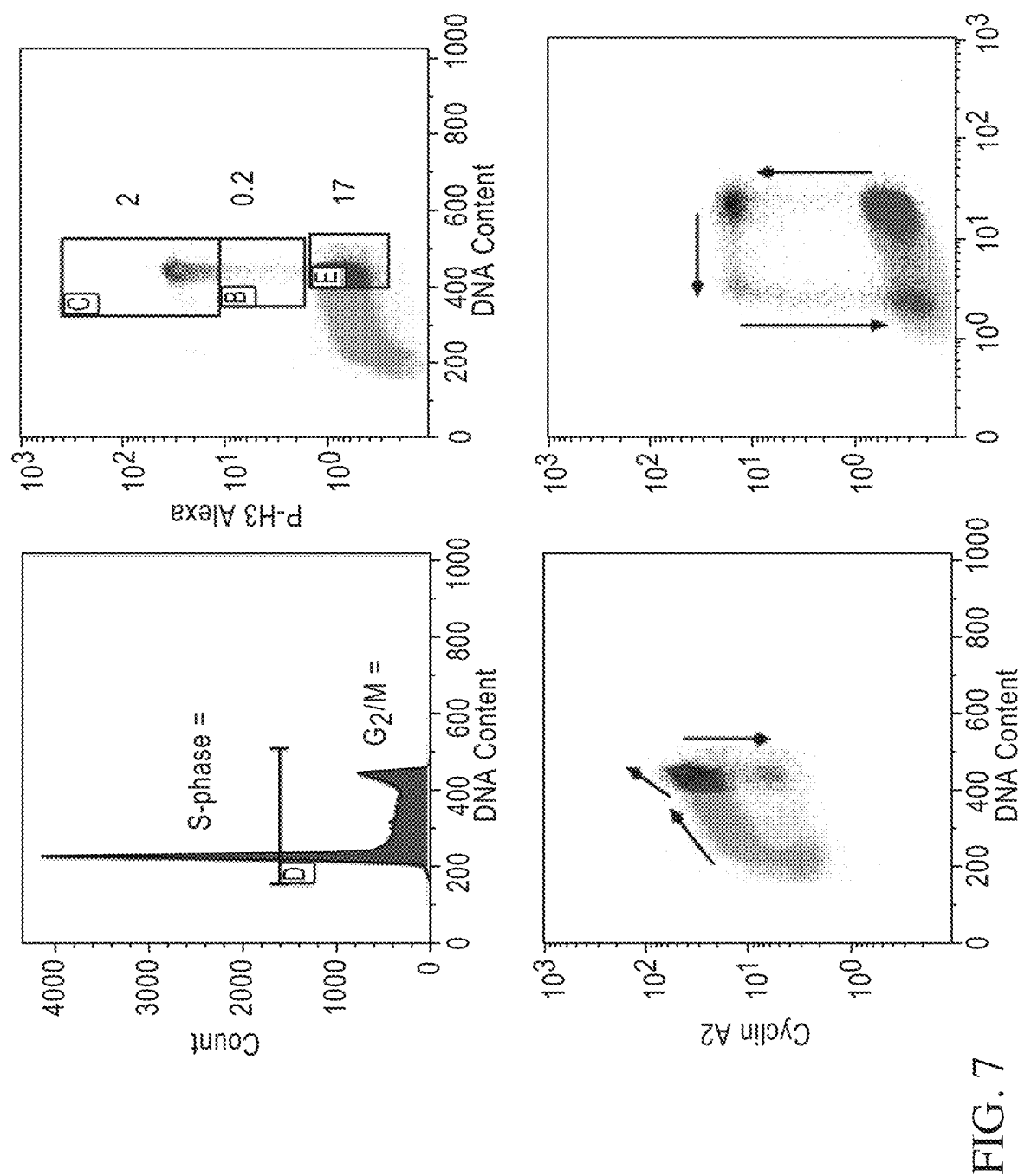
FIG. 7 shows the results of cell cycle analyses of fixed, permeabilized cells as described in Example 5A.

As shown in FIG. 7, cell cycle analysis, as indicated by DNA content, showed similar pattern of G1, S, and G2M populations (upper left panel) as shown for viable cell cycle staining in FIG. 5.

The same cells were also stained with an antibody to Cyclin A2 (conjugated to PE) and with an antibody to the phosphorylated form of histone H3 protein (P—H3), conjugated to ALEXA FLUOR® 647. Analysis of cell cycle versus P-H3 (upper right histogram) shows that the phosphorylated form of histone H3 protein is only expressed in the G2M population; analysis of cell cycle versus Cyclin A2 protein expression (lower left histogram) shows a more complex pattern of increasing levels of Cyclin A2 during the progression through S, and two populations of Cyclin A2 expression in G2M.

The biology of expression of Cyclin A2 in unperturbed cells is well characterized, and after reaching peak levels of expression during G2, Cyclin A2 is rapidly degraded on entry into mitosis (M). As shown in the lower right panel, analysis of the expression of Cyclin A2 versus P—H3 reveals a more complex pattern of the expression of these two proteins during progression through late S, to G2, to M. By "gating" the subsequent analysis on only these cell cycle populations (using DNA content), it is evident that P—H3 is first expressed in cells with the highest Cyclin A2 levels (G2 population), that P—H3 is maintained at high levels while Cyclin A2 is degraded, and that P—H3 is then "lost" (by de-phosphorylation of the specific Serine residue that was phosphorylated upon entry into G2) as cells progress from mitosis (M) back into G1. In traditional flow cytometric analysis, these sequences of changes in protein expression are established by careful manual "gating" (selecting) different cell populations (based on DNA content) and subsequently analyzing the expression of protein (or other targets defined by different antibody-conjugates).

Example 6: Signal Transduction

Signal Transduction pathways regulate multiple cell fate pathways, including cell division (proliferation), cell death (apoptosis, anoikis), and cell differentiation. In general, signaling acts through cytoplasmic receptors that activate downstream pathways after binding of a specific ligand recognized by the receptor. The hallmark of signaling pathways is a cascade of protein modifications (frequently phosphorylation of serine, or threonine, or tyrosine residues, though signaling can include other protein modifications, including methylation, acetylation, ubiquination, SUMOylation).

In phosphorylation, the most commonly studied signal transduction events at present, the activation of the cell surface receptor by its cognate ligand generates a kinase activity in the receptor. This active kinase then phosphorylates specific amino acid residues on its downstream partner, usually generating a kinase activity. This cascade generally continues until the terminal kinase translocates to the nucleus, where it binds to specific transcription activation sites on DNA. In addition, many signaling pathways act "laterally" to activate or inhibit other signaling pathways (e.g., activated β13 kinase can activate MAP kinase pathways, in addition to the downstream Akt>mTOR>ribosomal S6 kinase>S6>protein synthesis pathway).

An example of signal transduction pathways downstream of Toll-like receptor 4 (TLR4) found on peripheral blood monocytes is shown in FIG. 8. In contrast to most surface receptor-ligand interactions, in this highly unusual response, binding of the cognate ligand, lipopolysaccharide (LPS), to TLR4 activates multiple signal transduction pathways, including all three MAP (mitogen activated protein) kinases (ERK, p38 and SAP/JNK MAP kinases), β13 kinase, and the NF-xB pathway.

All of these pathways have been monitored using flow cytometry in peripheral blood monocytes. As above (for monitoring of proteins associated with cell cycle), cells can be fixed and permeabilized in order to allow intracellular (and nuclear) access for fluorophore-antibody conjugates.

Herein, specific dyes that monitor cell membrane permeability (marker for cell death), nuclear membrane permeability (marker for cell death), signal transduction pathways implicated in DNA damage (phospho-Histone H2A, phospho-ATM/ATR, phospho-p53), signal transduction pathways implicated in inflammation (e.g., NF-kB), signal transduction via the MAP kinase pathways (ERK, SAP/JNK, p38), signal transduction via the PI3 Kinase pathway (Akt, GSK3B, RS6K, $S_6$), early apoptotic pathways (e.g., annexin V), mid apoptotic pathways (e.g., cleaved caspase), late apoptotic pathways (e.g., PARP/DNA fragmentation), etc. may be employed. The results of a representative experiment measuring the kinetics of four signaling pathways simultaneously using flow cytometry are presented in FIG. 9. Here, human whole blood was treated with LPS in presence (experimental sample) or absence (control sample) of the PI3 kinase inhibitor GDC0941. The cells were fixed and permeabilized in accordance with the methods previously published in Shankey et al. ("Whole blood fixation and permeabilization protocol with red blood cell lysis for flow cytometry of intracellular phosphorylated epitopes in leukocyte subpopulations." Cytometry 67A;4-17, 2005) and stained with CD14-PECy7 (to identify monocytes in the cell mixture in normal White Blood Cells), plus antibodies to IκBα(conjugated to ALEXAFLUOR™ 488), P-ERK (conjugated to ALEXAFLUOR™647), P-Akt (conjugated to PE), and P-S6 (conjugated to Pacific Blue).

As shown in FIG. 9, LPS treatment activated the Iκ kinase, resulting in the proteasomal degradation of IκBα and loss of green/ALEXA FLUOR® 488 fluorescence signal. LPS treatment also activated ERK, Akt and S6 (as assayed by phosphorylation of downstream effectors). In the presence of the β13 kinase inhibitor GDC0941 (right panel), P-Akt was not phosphorylated, and the kinetics of ERK and S6 phosphorylation were delayed (compared to the cells treated with LPS alone). PI3K inhibition also had no impact on the proteasomal degradation of IκBα. The results shown here demonstrate:
 (1) Reproducible kinetics of responses in a normal cell population
 (2) Interactions within (horizontal) pathways (P-ERK activates P-S6 in monocytes—(3) S6 is not activated by Akt, as seen in other non-hematopoietic cells)
 (4) The use of well "mapped" inhibitors to study pathways.

Example 7: Tissue Culture Samples

In order to provide a more readily available and reproducible cell system (and to avoid the problems seen with existing methods), experimental systems based on tissue culture cell lines may be utilized to monitor the impact of drugs on signaling pathways.

Flow cytometric methods using tissue culture cells have been routinely used for investigating the effects of drugs, for example, inhibitors of Bcr/Abl kinase that are useful in the therapy of chronic myeloid leukemia (CML). CML is associated with the Philadelphia chromosome, a genetic translocation that fuses the Abl1 gene on chromosome 9 with part of the BCR gene on chromosome 22. The resulting fusion protein contains a receptor tyrosine kinase that constitutively activates several downstream signaling pathways, including P-STAT5, P-Crkl, P-mTOR, and P—HSF. The Abl kinase is the target of several therapeutics currently used clinically, including imatinib (GLEEVEC™), nilotinib, and dasatinib. These compounds act by inhibiting the tyrosine kinase activity at the receptor level, and also concomitantly inhibit all downstream signaling pathways.

As a representative model of CML, human K562 cell line, which expresses the Bcr/Abl fusion protein and constitutively phosphorylates the downstream STAT5 target (Cytometry 54A; 75-88, 2003), was used in the following experiment. As shown in FIG. 10, treatment of K562 cells for 30 min with 2 µM GLEEVEC™ (imatinib, or STI571) results in >95% inhibition of the phosphorylation of the downstream STAT5 target. Also, as shown in FIG. 10, although the phosphorylation of STAT5 is inhibited after 30 min imatinib exposure, there is no change in the cell cycle, as measured by DNA content.

Phosphorylated STAT5 (P-STAT5) acts as a transcriptional activator of several target proteins, including Cyclin D. Constitutive expression of Cyclin D (induced by P-STAT5) maintains K562 cells in cell cycle. It was found that exposure to imatinib for 24 hr decreases S-phase (as a marker of cell proliferation) by ~50%, and further exposure to imatinib for an additional 24 hr decreases S-phase by an additional 50-70% (data not shown).

Example 8: Effect of Troglitazone

Cells were treated with troglitazone, followed by incubation with the various fluorescence dyes (CALCEIN AM, MBBR, MITOSOX™ and CYTOSOX™). For each non-control well, the quadratic chi-distance distance to positive and negative control templates (for each fluorescence channel) was calculated and normalized with the scaling factor. The normalized data are reorganized into tensors, and the distance from positive and negative control templates are calculated. The similarities of the trioglitazone tensor to another compound tensor can be computed using known techniques by comparing the fiber columns of the tensors using dynamic time warping distance (see, Giorgino et al. "Computing and Visualizing Dynamic Time Warping Alignments in R: The dtw Package." *Journal of Statistical Software*, 31(7), 1-24, 2009). Dissimilarities or distances to all other compounds can be calculated this way.

Results are shown in FIG. 12.

Example 9: Automated Derivation of Cellular MMP Responses without Gating

Measurements of mitochondrial membrane potential are often performed in flow cytometry using mitochondrial sensors such as JC-1 and JC-9. These chemical species are dyes that exhibit potential-dependent accumulation in mitochondria, indicated by a fluorescence emission shift from green part of the visible light spectrum (~525 nm for JC-1) to red (~590 nm for JC-1). Therefore, physiological changes in mitochondria are indicated by shift in intensity ration between the two observed bands of fluorescence.

In cytometry, the detection of global (population-wide) change in MMP is typically measured by gating (selecting) the subpopulations of cells characterized by mostly low- and high-level of MMP. This requires manual data processing, or use of various clustering algorithms, which attempt to identify the relevant subpopulations of cells. When the subpopulations are identified, it is possible to create MMP response curves, which illustrate functions linking increasing compound concentrations and corresponding change in MMP.

These functions (curves) are typically created using percentage of cells in a specific gate (e.g. a gate delineating "high MMP" population) as a proxy providing information regarding response of a cell population to a compound exposure. Therefore, the response curves characterize the biochemical compounds of interest and can be used to further group the compounds into clusters, to mine the compound characteristics from databases of chemical compounds, or to predict the compounds functionality.

Although gating is typically used in the described applications, Bernas et al. demonstrated that it is feasible to determine differences between populations of cells in flow cytometry samples without it, by computing a robust dissimilarity metric (distance) between the distributions describing these populations (Bernas et al. (2008): Quadratic form: A robust metric for quantitative comparison of flow cytometric histograms; Cytometry A 73A, 715-726. doi: 10.1002/cyto.a.20586). The metric proposed by Bernas (quadratic-form distance) can operate in one- or higher number dimensions. Rajwa et al. teaches a method to compute these distances and use them in the context of quantifying differences between biological samples in flow cytometry (Rajwa et al. (2011): Quantification of differences between measured values and statistical validation based on the differences, US Patent Application Publication No. US20110066385 A1. Robinson et al. teaches a method to compute response curves and derive accompanying parameters of these curves, such as IC50, asymptotes, etc. by utilizing distance functions (Robinson et al. (2013): Gate-free flow cytometry data analysis, US Patent Application Publication No. US20130226469 A1). In this disclosure Robinson computes distances between a series of samples and a control. The used control could be a positive control, or a negative control. The disclosure demonstrates computing dissimilarities for individual channels of fluorescence.

An application of the methods disclosed by the references above would produce four complementary response curves: one encoding the dissimilarity between the series of samples and a positive control for the first measured band of fluorescence, a second one encoding the dissimilarity between the samples and the negative control in the same band, and two more curves constructed analogously for the second measured band. Although it is self-evident that the four response curves taken together contain the information similar to the information derived using the traditional approach utilizing percentages of cells in the identified cluster, it is not clear how the derived curves could be used in place of the single response curve, which has a well-established utility in biological compound analysis and medicinal chemistry.

Therefore, the disclosures cited above cannot be applied to the MMP case, even though they provide a practical solution to many other flow cytometry measurements.

In general, it can be said that the prior art does not include a method of computing a single response curve for samples in which information about biological response is encoded in more than one dimension, and the use of both positive control and negative control is required. Bernas et al. mentions the fact that the proposed distance function is scalable to multiparameter (multidimensional) cytometry, the authors do not disclose a practically applicable implementation or a demonstration of a multidimensional case. Robinson et al. teach that multiple comparisons between samples in a series and a control can be arranged in a series leading to a response curve similar to a response curve extracted from manual data gating. However, Robinson et a. are silent on the use of the disclosed method in two-dimensional case such as measurements of JC-, JC-9, JC-10 and other ratiometric dyes. This disclosure teaches the derivation of response curves using distance functions for the MMP measurements and other measurements in which two or more types of controls are used, and the biological samples are characterized by two or more measurements.

The method described below is capable of deriving a single response curve containing all the information necessary to determine the characteristics of the response exhibited by the biological compound of interest when acting on the population of cells.

The method involves the application of distance functions to marginal histograms (one-dimensional histograms) formed by flow cytometry measurements.

(A) In Silico Simulation

A method that uses an application of a distance function to marginal histograms (one-dimensional histograms) formed by flow cytometry measurements in accordance with embodiments herein disclosed in illustrated in the following in silico example.

FIG. 19 illustrates a computer simulation of ten flow cytometry samples exposed to an increasing concentration of an agent influencing mitochondrial membrane potential. FIG. 18 shows negative and positive controls. The change in the number and percentage of cells belonging to the cluster of cells defined by the negative control is illustrated in FIG. 20. Panel A shows response curves as a function of number of cells. B shows response curves as a function of percent of cells.

First, a pair of distances between the positive control ($C_p$) and the negative control ($C_n$) is computed. The two distances are defined for FL1 marginal histograms ($C^1$), and FL2 marginal histograms ($C^{11}$). These distances are references for further use and rescaling:

$$f_1 = D(C_p^I, C_i^I)$$

$$f_2 = D(C_p^{II}, C_i^{II})$$

where i is the number indicating the sample in a dilution series, and Roman numerals (I, II) indicate the channel number. The equation shows a two-dimensional case (two marginal histograms); therefore, only two Roman numerals are used. The distance function D can be a quadratic form distance, a Wasserstein distance, a quadratic-$\lambda^2$ distance, or any other distance operating on vectors representing histograms.

Following this operation, a series of distances for the biological samples are calculated in an analogous fashion. Distances are computed for every pair of the positive control and a biological sample in the series ($S_1, S_2, \ldots, S_i$), as well as the negative control samples (See FIG. 21):

$$d_{n,i}^I = D(C_n^I, S_i^I)$$

$$d_{p,i}^I = D(C_p^I, S_i^I)$$

$$d_{n,i}^{II} = D(C_n^{II}, S_i^{II})$$

$$d_{p,i}^{II} = D(C_p^{II}, S_i^{II})$$

The resultant values form an array. The size and the dimensionality of the array depend on the number of controls and the number of utilized one-dimensional histograms, as explained further. In the MMP case, two controls are used, and two fluorescence channels are measured.

$$A = \begin{bmatrix} \begin{bmatrix} d_{1,p}^1 = D(C_p^1, S_1^1) \\ d_{2,p}^1 = D(C_p^1, S_2^1) \\ d_{3,p}^1 = D(C_p^1, S_3^1) \\ \vdots \\ d_{1,p}^1 = D(C_p^1, S_i^1) \end{bmatrix}, \begin{bmatrix} d_{1,n}^1 = D(C_n^1, S_1^1) \\ d_{2,n}^1 = D(C_n^1, S_2^1) \\ d_{3,n}^1 = D(C_n^1, S_3^1) \\ \vdots \\ d_{1,n}^1 = D(C_n^1, S_i^1) \end{bmatrix} \end{bmatrix},$$

$$\begin{bmatrix} \begin{bmatrix} d_{1,p}^{11} = D(C_p^{11}, S_1^{11}) \\ d_{2,p}^{11} = D(C_p^{11}, S_2^{11}) \\ d_{3,p}^{11} = D(C_p^{11}, S_3^{11}) \\ \vdots \\ d_{1,p}^{11} = D(C_p^{11}, S_i^{11}) \end{bmatrix}, \begin{bmatrix} d_{1,n}^{11} = D(C_n^{11}, S_1^{11}) \\ d_{2,n}^{11} = D(C_n^{11}, S_2^{11}) \\ d_{3,n}^{11} = D(C_n^{11}, S_3^{11}) \\ \vdots \\ d_{1,n}^{11} = D(C_n^{11}, S_i^{11}) \end{bmatrix} \end{bmatrix}$$

The array of measurements (two matrices shown above) can be also viewed as a three-way tensor. The dimensionality of this three-way tensor is $I_1 \times I_2 \times I_3$, where $I_1$ is the number of tested concentrations (typically 10), $I_2$ is the number of measured responses (in the case of JC-like labels—two), and $I_3$ is the number of measured dissimilarities/distances (typically two: positive control distance measurement, and a negative control distance measurement). Therefore, for a tensor A representing the biological measurement, the element (i, j, k), denoted by $\alpha_{i,j,k}$ describes a distance between measurements of parameter j obtained from a cell population exposed to a compound at concentration i, and a control cell population k.

In the third step, following the arrangement of data in the tensor A, tensor decomposition is performed. The goal of tensor decomposition is formation low-rank tensors, which contain all or most information of the higher order tensor. In the demonstrated example, the utilized decomposition is the polyadic tensor decomposition (CP). The tensor A is decomposed into two decomposed in two tensors.

The objective of the CP decomposition is finding an approximation of tensor A denoted Á, which satisfies the following criteria:

$$\min_{\hat{A}} \|A - \hat{A}\|, \text{ where } \hat{A} = \hat{A}_1 + \hat{A}_1 = \lambda_1 a_1^{(1)} \circ a_1^{(2)} \circ a_1^{(3)} + \lambda_2 a_2^{(1)} \circ a_2^{(2)} \circ a_2^{(3)}$$

where ∘ denotes outer product.

The first vector building the first tensor $Á_1$ (henceforth denoted $A_1$ for simplification) $a_1^{(1)}$ (henceforth denoted $a_1$) describes the overall change in response exhibited by the series of the biological samples over the rested concentration of compounds FIG. 22A). The $a_1$ vector can be further characterized by fitting a pre-conceived model of response (such as log-logistic, Gompertz, Weibull, Cedergreen-Ritz-Streibig, Brain-Cousens, etc.) (Cedergreen et al., 2005; Meddings et al., 1989). The example of such fitting is shown in FIG. 22B.

In all the in silico simulated samples shown in FIG. 19 the total number of cells is 5000. The number of cells in the "positive control"-like cluster shown in Figures in FIG. 19A to FIG. 19J is 4909, 4753, 4409, 3650, 2478, 1370, 581, 234, 87, and 29, respectively. As mentioned before, the information about the change can be also visualized as a percentage of cells in the cluster, or as a difference between the percentage of cells in the cluster and the percentage of cells belonging to the cluster in the negative control. In the demonstrated example these percentages are 98.18, 95.06, 88.18, 73, 49.56, 27.4, 11.62, 4.68, 1.74, and 0.58 for the samples from A to J (FIG. 19), respectively. In all the case a sigmoidal shape characterizes the plotted function.

The response curve computed by polyadic tensor decomposition (curve described by vector $a_1$) is demonstrated in FIG. 22A. The curve retains the sigmoidal characteristics providing the same information about functional dependence between concentration (encoded by sample number) and a relative level of response. The curve can be re-scaled using distances between controls. Following the rescaling the dissimilarity of 1 is equal to the dissimilarity between negative and positive control. The plot presenting correspondence between the response curves derived using the traditional methodology, and the described method is provided in FIG. 23.

(B) Analysis of Cell Responses to Valinomycin and Two Other Agents

The procedure described above was performed on real flow cytometry data. Results are displayed in FIGS. 24 and 25. The data was obtained using the methods described herein above.

FIG. 24 shows a series of flow cytometry plots demonstrating the change in cell populations exposed to valinomycin. FIG. 25A provides response curves derived from the flow cytometry data. In addition to valinomycin in FIG. 24, additionally samples exposed to idarubicin and acetomiphen were used. The unit of dissimilarity in FIG. 25A is the difference between positive and negative control, where the positive control is a sample treated with FCCP at a concentration of 25 μm.

The computed response data can be also used to fit a defined sigmoidal-curve model. For instance, a log-logistic four-parameter model fitted into the provided examples, represent the approximated functional dependence between concentration and sample response in FIG. 25B.

From the careful consideration of the foregoing description in light of the references cited herein, one skilled in the art can ascertain the characteristics of inventions and embodiments herein describe and will be enabled thereby to undertake a wide a variety of changes and modifications thereof without departing from the spirit and scope thereof.

All publications and patents cited above are incorporated herein by reference. in their entireties, particularly as to parts pertinent to the foregoing discussion thereof.

What is claimed is:

1. A data storage and retrieval system for a non-transitory computer readable storage medium comprised of fingerprints that are multiparametric response tensors characteristic of the effects of agents on cells determined by cell cytometry, wherein the fingerprints are provided by a cell cytometry method for measuring the effect of an agent on cells, said method comprising:

contacting aliquots of a population of cells with K different control conditions, where κ is at least 1, and with i different concentrations of an agent, where i is at least 1;

measuring p different phenotypic parameters, ψ, in individual cells of each aliquot, where p is at least 3 and, where $\psi_p$ denotes a particular phenotypic parameter, thereby obtaining distributions $C_k$ of the measured values for each control condition K for each phenotypic parameter $\psi_p$ and distributions $S_i$ of the measured values for each concentration condition i for each phenotypic parameter $\psi_p$, wherein the phenotypic parameters are measured in the individual cells by cell cytometry using a cell cytometer, and wherein a multiparametric tensor fingerprint indicative of the response of the cells to the agent is produced from said measurements without gating by, calculating pairwise distances d between the distributions of each control condition $C_k$ and each concentration condition $S_i$ separately for each phenotypic parameter $\psi_p$, where $$d_{\kappa,i}^{(\psi)} = D(C_\kappa^{(\psi)}, S_i^{(\psi)})$$

and D is a distance function;

combining the calculated distances to form a multiparametric response tensor A $$A = \begin{bmatrix} a_{[\kappa_1,\psi_1]} & \cdots & a_{[\kappa_1,\psi_p]} \\ \vdots & \ddots & \vdots \\ a_{[\kappa_m,\psi_1]} & \cdots & a_{[\kappa_m,\psi_p]} \end{bmatrix}$$

wherein each of $a_{[\kappa,\ 104]}$ comprises all the pairwise distances calculated for one phenotypic parameter and one control:

$$a_{[\kappa,\psi]} = \begin{bmatrix} d_{\kappa,1}^{(\psi)} = D(C_\kappa^{(\psi)}, S_1^{(\psi)}) \\ d_{\kappa,1}^{(\psi)} = D(C_\kappa^{(\psi)}, S_2^{(\psi)}) \\ \vdots \\ d_{\kappa,1}^{(\psi)} = D(C_\kappa^{(\psi)}, S_n^{(\psi)}) \end{bmatrix}$$

wherein the multiparametric response tensor A is a fingerprint characteristic of the effects of the agent on the cells that can be compared directly to other such fingerprints generated in the same way, wherein the cytometry and the fingerprint are free of gating bias.

2. The data storage and retrieval system for a non-transitory computer readable storage medium of claim 1, wherein the fingerprints can be compared to one another to determine similarities and/or differences in effects of one or more agents on cells.

3. The data storage and retrieval system for a non-transitory computer readable storage medium of claim 1, wherein the fingerprints can be compared to fingerprints made by the same method in other databanks to determine similarities and/or differences in the effects of one or more agents on cells.

4. The data storage and retrieval system for a non-transitory computer readable storage medium of claim 1, wherein the fingerprints are useful to predict in vivo effects of agents.

5. The data storage and retrieval system for a non-transitory computer readable storage medium of claim 1, wherein the in vivo effect is one or more of toxicity, efficacy and off-target effects.

6. The data storage and retrieval system for a non-transitory computer readable storage medium of claim 1, wherein the phenotypic parameters for one or more of the fingerprints therein include any two or more of cell viability, cell cycle stage, mitochondrial membrane integrity, mitochondrial toxicity, glutathione concentration, reactive oxygen species, reducing species, cytoplasmic membrane permeability, DNA damage, a stress response marker, an inflammatory response marker, an apotosis marker and a lipid peroxidase.

7. The data storage and retrieval system for a non-transitory computer readable storage medium of claim 1, wherein the phenotypic parameters for one or more of the fingerprints therein include any one or more of NFκB, caspase, ERK, SAPK, β13K, AKT, a Bcl-1 family protein, p38, ATM GSk3B and ribosomal S6 kinase.

8. The data storage and retrieval system for a non-transitory computer readable storage medium of claim 1, wherein one of the phenotypic parameters for one or more of the fingerprints is cell cycle.

9. The data storage and retrieval system for a non-transitory computer readable storage medium of claim 1, wherein for one or fingerprints each population of cells is functionally labeled with a plurality of fluorescence dyes and the phenotypic parameters are detected and quantitated in terms of spectral emission signal(s) that are generated when said populations of labeled cells are subjected to cytometric analysis.

10. The data storage and retrieval system for a non-transitory computer readable storage medium of claim 1, wherein for one of more fingerprints a phenotypic parameter is cell cycle and it is quantitated in terms of any one or more of the HOECHST 33342, DRAQ5, YO—PRO-1 IODIDE, DAPI, CYTRAK ORANGE, cyclin or phosphorylated histone protein.

11. The data storage and retrieval system for a non-transitory computer readable storage medium of claim 1, wherein the fingerprints are stored in a computer readable medium such that they can be comparted one another and to fingerprints for other agents produced the same way.

12. The data storage and retrieval system for a non-transitory computer readable storage medium of claim 1, wherein the pairwise differences d are normalized to the pairwise difference between a "negative" control and a "positive" control.

13. The data storage and retrieval system for a non-transitory computer readable storage medium of claim 1, wherein separately for each phenotypic parameter marginal distributions $C_k$, are calculated for each of the distributions obtained for the control conditions, and marginal distributions $S_i$ are calculated for each of the distributions obtained for the concentration conditions and pairwise distances are calculated between the marginal distributions.

14. The data storage and retrieval system for a non-transitory computer readable storage mediume of claim 1, wherein the differences are calculated by a Wasserstein distance, a quadratic-form distance, a Kolmogorov distance, or a symmetrized Kullback-Leibler divergence dissimilarity measure.

15. The data storage and retrieval system for a non-transitory computer readable storage medium of claim 1, wherein the multiparametric tensor A is decomposed into either one or both of:

(a) a set of rank-one tensors $A^{(i)}$, wherein $$A = [[\lambda; A^{(1)}, A^{(2)}, ..., A^{(n)}]] = \sum_{r=1}^{R} \lambda_r a_r^{(1)} \circ a_r^{(2)} \circ \cdots \circ a_r^{(p)},$$

and (b) a core tensor G multiplied by a matrix $M^{(j)}$ along each mode:

$$A = [[G; M^{(1)}, M^{(2)}, ..., M^{(p)}]] = \sum_{r_1=1}^{R_1} \sum_{r_2=1}^{R_2} \cdots \sum_{r_p=1}^{R_p} g_{r_1 r_2 \cdots r_p} m_{r_1}^{(1)} \circ m_{r_2}^{(2)} \circ \cdots \circ m_{r_N}^{(p)}.$$

16. The data storage and retrieval system for a non-transitory computer readable storage medium of claim 1, wherein the dissimilarity between a first fingerprint multiparametric response tensor A first and a second fingerprint multiparametric response tensor B are calculated according to the following formula:

$$w_{A,B} = D(A,B) = d(a_{jk}, b_{jk}),$$

where D is the dissimilarity between tensors A and B, d is a distance function comparing the mode-1 fibers of each of the tensors, and w is a distance vector indicative of the dissimilarity between the first and second fingerprints.

17. The data storage and retrieval system for a non-transitory computer readable storage medium of claim 16, wherein w is the Frdchet distance or the dynamic time-warping distance.

18. The data storage and retrieval system for a non-transitory computer readable storage medium of claim 1, wherein:

the number of control conditions K is 2;

the number of concentration conditions i is any integer number 10 or above, and the number of phenotypic parameters p is any integer number 5 or above.

19. A cell cytometry system, comprising, in one or more combined or separate parts:

(A) a cell cytometry apparatus for measuring the phenotypic characteristics of individual cells in a sample processed by a method comprising:

contacting aliquots of a population of cells with K different control conditions, where κ is at least 1, and with i different concentrations of an agent, where i is at least 1;

measuring p different phenotypic parameters, ψ, in individual cells of each aliquot, where p is at least 3 and, where $\psi_p$ denotes a particular phenotypic parameter, thereby obtaining distributions $C_k$ of the measured values for each control condition K for each phenotypic parameter $\psi_p$ and distributions $S_i$ of the measured values for each concentration condition i for each phenotypic parameter $\psi_p$, and (B) a device for storing the measurements of the phenotypic characteristics of the individual cells and for analyzing the measurements by a gateless method that produces a multiparametric tensor fingerprint indicative of the response of the cells to the agent, said method comprising:

calculating pairwise distances d between the distributions of each control condition $C_k$ and each concentration condition $S_i$ separately for each phenotypic parameter $\psi_p$, where $$d_{\kappa,i}^{(\psi)} = D(C_\kappa^{(\psi)}, C_i^{(\psi)})$$

and D is a distance function;

combining the calculated distances to form a multiparametric response tensor A $$A = \begin{bmatrix} a_{[\kappa_1,\psi_1]} & \cdots & a_{[\kappa_1,\psi_p]} \\ \vdots & \ddots & \vdots \\ a_{[\kappa_m,\psi_1]} & \cdots & a_{[\kappa_m,\psi_p]} \end{bmatrix}$$

wherein each of $a_{[\kappa, \psi]}$ comprises all the pairwise distances calculated for one phenotypic parameter and one control:

$$a_{[\kappa,\psi]} = \begin{bmatrix} d_{\kappa,1}^{(\psi)} = D(C_\kappa^{(\psi)}, S_1^{(\psi)}) \\ d_{\kappa,1}^{(\psi)} = D(C_\kappa^{(\psi)}, S_2^{(\psi)}) \\ \vdots \\ d_{\kappa,1}^{(\psi)} = D(C_\kappa^{(\psi)}, S_n^{(\psi)}) \end{bmatrix}$$

wherein the multiparametric response tensor A is a fingerprint characteristic of the effects of the agent on the cells that can be compared directly to other such fingerprints generated in the same way wherein said fingerprints are free of gating bias, and (C) a device for storing a databank comprising a plurality of the fingerprints, wherein (A), (B) and (C) can be comprised in one or more than one instruments.

* * * * *